United States Patent
Rughani et al.

(10) Patent No.: US 12,268,767 B2
(45) Date of Patent: Apr. 8, 2025

(54) COMPOSITIONS AND METHODS FOR TREATING HAIR

(71) Applicant: L'Oreal, Paris (FR)

(72) Inventors: Ronak Rughani, Edison, NJ (US); Cho-Cho Khine, Scotch Plain, NJ (US); David Ladd, Kenilworth, NJ (US); Yamini Patel, East Brunswick, NJ (US)

(73) Assignee: L'OREAL, Paris (FR)

( * ) Notice: Subject to any disclaimer, the term of this patent is extended or adjusted under 35 U.S.C. 154(b) by 130 days.

(21) Appl. No.: 18/115,715

(22) Filed: Feb. 28, 2023

(65) Prior Publication Data
US 2023/0270641 A1    Aug. 31, 2023

Related U.S. Application Data

(60) Provisional application No. 63/315,075, filed on Feb. 28, 2022.

(30) Foreign Application Priority Data

Apr. 26, 2022  (FR) .................................. 2203846

(51) Int. Cl.
  *A61Q 5/10*   (2006.01)
  *A61K 8/365*  (2006.01)
  *A61K 8/42*   (2006.01)

(52) U.S. Cl.
  CPC ............... *A61K 8/365* (2013.01); *A61K 8/42* (2013.01); *A61Q 5/10* (2013.01);
  (Continued)

(58) Field of Classification Search
  CPC .. A61K 8/365; A61K 8/42; A61K 2800/4324; A61K 2800/592;
  (Continued)

(56) References Cited

U.S. PATENT DOCUMENTS

| | | |
|---|---|---|
| 4,003,699 A | 1/1977 | Rose et al. |
| RE30,199 E | 1/1980 | Rose et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

Copending U.S. Appl. No. 18/115,247, entitled "Compositions and Methods for Curly Hair," Inventors: Ronak Rughani et al., filed Feb. 28, 2023.

(Continued)

*Primary Examiner* — Eisa B Elhilo
(74) *Attorney, Agent, or Firm* — THE MARBURY LAW GROUP, PLLC

(57) ABSTRACT

The disclosure relates to compositions for use before, during, and/or after the hair is subject to a process for altering the color thereof. The compositions comprise a combination of citric acid and at least one urea compound. The compositions provide strength and other benefits to treated hair. The disclosure also relates to methods of using the compositions as well as kits comprising the compositions.

20 Claims, 12 Drawing Sheets

(52) U.S. Cl.
CPC ...... *A61K 2800/4324* (2013.01); *A61K 2800/592* (2013.01); *A61K 2800/805* (2013.01)

(58) Field of Classification Search
CPC .... A61K 2800/805; A61K 8/34; A61K 8/345; A61K 8/416; A61K 8/73; A61K 8/891; A61K 8/898; A61K 8/92; A61Q 5/10; A61Q 5/00; A61Q 5/002; A61Q 5/004; A61Q 5/06
USPC .............................................................. 8/405
See application file for complete search history.

(56) References Cited

U.S. PATENT DOCUMENTS

| | | | |
|---|---|---|---|
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A * | 6/1998 | Lowe | C07D 231/38 424/70.6 |
| 6,099,592 A | 8/2000 | Vidal et al. | |
| 6,284,003 B1 * | 9/2001 | Rose | A61K 8/411 8/408 |
| 6,730,789 B1 | 5/2004 | Birault et al. | |
| 7,857,865 B2 * | 12/2010 | Guerin | A61K 8/347 8/405 |
| 9,993,413 B2 * | 6/2018 | Consoli | A61Q 5/10 |
| 10,004,673 B1 * | 6/2018 | Elsen-Wahrer | A61K 8/41 |
| 10,105,301 B2 * | 10/2018 | Consoli | A61K 8/49 |
| 2017/0258695 A1 * | 9/2017 | Consoli | A61K 8/55 |

FOREIGN PATENT DOCUMENTS

| | | |
|---|---|---|
| DE | 4133957 A1 | 4/1993 |
| DE | 19543988 A1 | 5/1997 |
| EP | 0530974 A1 | 3/1993 |
| EP | 0714954 A2 | 6/1996 |
| EP | 0770375 A1 | 5/1997 |
| EP | 3589723 A1 | 1/2020 |
| FR | 2733749 A1 | 11/1996 |
| FR | 2801308 A1 | 5/2001 |
| FR | 2886136 A1 | 12/2006 |
| FR | 3115201 A1 | 4/2022 |
| FR | 3115203 A1 | 4/2022 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 2018/160809 A1 | 9/2018 |

OTHER PUBLICATIONS

French Search Report and Written Opinion for counterpart French Application No. FR 203845, dated Nov. 29, 2022.
French Search Report and Written Opinion for counterpart French Application No. FR 2203846, dated Nov. 30, 3 2022.
Mintel: "Coconut Hair Mask," RB Group, Record ID 8051545, XP093003590, Aug. 24, 2020.
Mintel: "Curl Activator," Plus Cosmetica, Record ID 4986931, XP093003273, Jul. 27, 2017.
Mintel: "Hydrating Shampoo for Curly Hair," L'Bel, Record ID 2073932, XP093003274, May 28, 2013.
Mintel: "Hydration Ultra Curls Concentrated Hair Mask," Devintex Cosmeticos, Record ID 6537213, XP093003271, May 13, 2019.
Mintel: "Permanent Colouration and Treatment," Plus Cosmetica, Record ID 3915517, XP093003589, Apr. 7, 2016.
Mintel: Post-Chemistry Shampoo, Beka Cosméticos, Record ID 3905061, XP093003588, Apr. 7, 2016.
International Preliminary Report on Patentability in PCT/US2023/014087, mailed Sep. 12, 2024, 9 pages.
International Preliminary Report on Patentability in PCT/US2023/014181, mailed Sep. 12, 2024, 9 pages.

* cited by examiner (a)   (b)

(a)  (b)

C4      3A

C5  4A

COMPOSITIONS AND METHODS FOR TREATING HAIR

CROSS REFERENCE TO RELATED APPLICATIONS

This application claims priority to U.S. Provisional Application No. 63/315,075, filed on Feb. 28, 2022, and French Application No. 2203846, filed on Apr. 26, 2022, both of which are incorporated by reference herein in their entireties.

TECHNICAL FIELD

The present disclosure relates to compositions for treating hair before, during, and/or after the hair is subjected to a process for altering the color thereof, as well as methods of using the compositions and kits comprising the compositions.

BACKGROUND

Changing or enhancing the appearance of hair is very popular with consumers, including for example changing hair color or tone and/or imparting various properties, for example, shine, and conditioning of the hair.

Hair coloring typically involves bleaching, lightening, and/or changing the hair color through oxidative dyes, direct dyes, and/or pigments providing a different shade or color, and/or lifting the color of the hair. Hair lightening processes, or lifting the color of hair, generally require the use of compositions that comprise at least one oxidizing agent to lighten the color of dark hair to lighter shades. When colorants or dye compounds such as oxidation dye precursors and/or direct dyes are present in these compositions, such compositions can change or deposit color while lightening the color of hair at the same time.

Imparting a color change or color effect on hair can be done using permanent, semi-permanent, or temporary hair coloring products. Conventional permanent dye compositions comprising oxidation dye precursors, which are also known as primary intermediates or couplers. These oxidation dye precursors are colorless or weakly colored compounds which, when combined with oxidizing agents, give rise to colored complexes by a process of oxidative condensation. Semi-permanent dyeing uses direct dyes, which are nonionic or ionic dyes and colored compounds capable of producing a more or less pronounced change of the natural color of the hair. These dyes may or may not be used in the presence of an oxidizing agent. In contrast with oxidation dye precursors, a direct dye is a relatively large molecule that does not penetrate easily into the core of the fiber.

Variation in tone height before and after the application of a hair color-altering composition is typically evaluated when lightening or lifting the color of the hair. The degree or level of lightening or lift is determined by the variation. "Tone" refers to the "finish" of a shade, including is degree of warmth or coolness and is based on the classification of natural shades, one tone separating each shade from the shade immediately following or preceding it. Tone heights or levels typically range from 1 (black) to 10 (light blonde), one unit generally corresponding to one tone. Accordingly, the higher the tone number, the lighter the shade and the greater the degree of lift.

Hair dyeing or color lifting compositions may require one or more alkalizing agents, such as ammonia and/or ammonium-based compounds, which cause the hair shaft to swell, thus allowing small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While such hair dyeing and/or color lifting compositions can effectively alter the color of hair, these compositions can damage the hair fibers and/or irritate the scalp due to excessively high levels of alkalinity.

Thus, in order to reduce or avoid damage to hair, as well as to improve the cosmetic performance of the compositions, different types of hair coloring products have been developed by manufacturers that are aimed to help consumers achieve a desired look, including one or more attributes such as fuller hair, thicker hair, sleek and straight hair, and frizz-controlled hair. These products are typically provided in forms that are applied after completion of coloring, shampooing, and conditioning processes. There is still a need for new and improved products and methods for treating keratin fibers, in particular human hair, during a process of bleaching and/or coloring hair, or during a conditioning process before and/or after the hair is bleached and/or colored.

The present disclosure addresses these concerns and needs, and relates to new compositions and methods that can reduce the damage to hair and impart improved attributes such as manageability, smoothness, and frizz-control, during or after a bleaching and/or coloring process.

SUMMARY

The disclosure relates to compositions for treating and caring for hair before, during, and/or after bleaching and/or coloring the hair, as well as methods of using the compositions and kits comprising the compositions. The compositions according to the disclosure include a synergistic combination of citric acid and at least one urea compound.

It has surprisingly been found that a synergistic combination of citric acid and urea compounds, when incorporated into compositions such as a composition for caring for or treating bleached and/or colored hair, or incorporated into compositions for altering the color of hair, surprisingly imparts unexpected strength to the hair as well as various cosmetic properties such as improved curl or wave definition, improved curl or wave retention, improved softness, better smoothness, better discipline, better alignment, greater ease of detangling, and/or better frizz control. In addition, in some embodiments, the compositions surprisingly impart unexpected color uniformity and/or have improved ease of application to hair. Even more surprisingly, these benefits have been found to last through several hair care and styling cycles. Further, it has also been discovered that including a synergistic combination of citric acid and urea compounds in hair color altering compositions provides the surprising benefit of extending the color imparted to the hair through several shampoo cycles.

In various embodiments, compositions according to the disclosure provide one or more benefits to processed hair that has been bleached and/or colored, such as strength, frizz control, smoothness, and/or soft feel, and comprise (a) a combination of (i) citric acid and (ii) at least one urea compound chosen from urea and/or derivatives thereof; (b) at least one additional component for conditioning, caring for, and/or treating the hair; and (c) at least one solvent. In certain embodiments, components for conditioning, caring for, and/or treating for the hair may be chosen from silicone compounds, fatty compounds other than silicone compounds, cationic surfactants, or mixtures thereof. The compositions may optionally include one or more other components useful in compositions for treating and/or conditioning hair, such as, for example, polyols, thickening agents, pH adjustors, direct dyes, preservatives, fragrances, or mixtures thereof.

In some embodiments, the disclosure relates to compositions for conditioning, caring for, and/or treating bleached and/or colored hair. The compositions typically comprise (a) a combination of (i) citric acid and (ii) at least one urea compound chosen from urea and/or derivatives thereof; (b) at least one silicone compound; (c) at least one fatty compound other than silicone compounds; and (d) at least one aqueous solvent. The compositions may optionally further comprise additional components, such as, (e) at least one vegetable oil; (f) at least one polyol; (g) at least one cationic surfactant; and/or (h) at least one thickening agent. In various embodiments, the pH of the composition is less than about 10, for example less than about 7.

In yet further embodiments, the disclosure relates to hair color altering compositions comprising (a) a combination of (i) citric acid and (ii) at least one urea compound chosen from urea and/or derivatives thereof; and (b) at least one hair color altering agent. In certain embodiments, the hair color altering agent may be a compound for temporarily altering the color of the hair, such as a pigment or direct dye, and in other embodiments the hair color altering agent may be an agent for permanently altering the color of the hair, such as an oxidizing agent and/or an oxidation dye. In certain embodiments, the pH of the hair color altering composition is greater than about 7, such as greater than about 9, or greater than about 10.

In various embodiments, the mole ratio of citric acid to urea compounds in the compositions described herein ranges from about 0.3 to about 2.5, for example from about 0.3 to about 2.0, from about 0.4 to about 1.5, or from about 0.5 to about 1.4, or is about 0.45, about 0.5, about 0.55, about 0.6, about 0.65, about 0.7, about 0.75, about 0.8, about 0.85, or about 0.9, or is chosen from a range using any of the foregoing as upper and lower limits.

In various embodiments, the weight ratio of the total amount of citric acid to the total amount of urea compounds ranges from about 1:1 to about 1:0.05, for example from about 1:0.95 to about 1:0.1, from about 1:0.9 to about 1:0.3, from about 1:0.85 to about 1:0.5, or from about 1:0.8 to about 1:0.6, or is about 1:0.8, about 1:0.75, about 1:0.7, about 1:0.65, or about 1:0.6, or is chosen from a range using any of the foregoing as upper and lower limits.

In further embodiments, the combination of the total amounts of citric acid and urea compounds ranges from about 0.5% to about 50%, for example from about 0.75% to about 20%, from about 1% to about 15%, from about 1.25% to about 10%, or from about 1.5% to about 5% by weight, relative to the total weight of the composition. Citric acid (including salts) may be present in a total amount ranging from about 0.25% to about 40%, for example from about 0.5% to about 20%, from about 1% to about 10%, from about 1.1% to about 5%, or from about 1.2% to about 3% by weight, relative to the total weight of the composition.

In various embodiments, the at least one urea compound comprises, consists essentially of, or consists of urea, dimethyl urea, hydroxyethyl urea, or mixtures thereof.

In various embodiments, the compositions comprise a combination of citric acid and hydroxylethyl urea in a total amount ranging from about 1.25% to about 5%, and the weight ratio of citric acid to hydroxylethy urea ranges from about 1:0.85 to about 1:0.5, for example from about 1:0.8 to about 1:0.6, or is about 1:0.8, about 1:0.75, or about 1:0.7, or is chosen from a range using any of the foregoing as upper and lower limits.

The disclosure also relates to methods of treating hair before, during, and/or after a process for altering the color of hair, methods of caring for hair before, during, and/or after a process for altering the color of hair, methods of altering the color of hair, methods of imparting strength to hair, and/or methods of imparting one or more benefits such as smoothness, shine, curl definition, curl retention, softness, manageability, reduced frizziness, or the like to hair. In various embodiments, the methods comprise applying a composition according to the disclosure before, during, and/or after a process for altering the color of the hair, optionally leaving the composition on the hair for a leave-in period, and optionally rinsing the hair.

The disclosure further relates to kits. For example, in some embodiments the kits comprise a first compartment or container containing a pre-phase mixture of citric acid and urea compounds as described herein, and a second compartment or container containing one or more of a hair care/treatment composition, a temporary hair color altering composition, a hair (color) base composition, a bleach composition and/or a developer composition. In other embodiments, the kits comprise at least two compartments or containers, wherein a first compartment or container comprises a pre-phase mixture of citric acid and urea compounds as described herein and a second compartment or container comprises a treatment, care, or conditioning composition according to the disclosure. In still further embodiments, the kits comprise at least two compartments or containers, wherein a first compartment or container comprises a composition for altering the color of the hair according to the disclosure, and a second compartment or container comprises a treatment, care, or conditioning composition according to the disclosure.

BRIEF DESCRIPTION OF FIGURES

The accompanying drawings, which are incorporated herein and constitute part of this specification, illustrate exemplary embodiments of the disclosure, and, together with the general description given above and the description provided herein, serve to explain features of the disclosure.

Figure 1A:
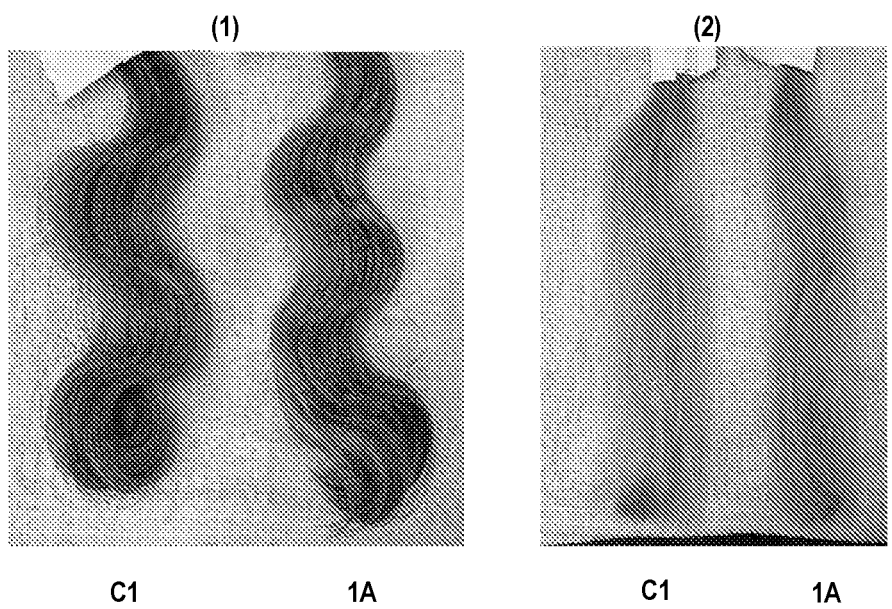
FIGS. 1A-1B are images showing hair swatches treated after undergoing a bleaching process, with an exemplary hair care/treatment composition according to the disclosure in comparison with a comparative composition outside the disclosure.

It is to be understood that the foregoing and following descriptions are exemplary and explanatory only and are not intended to be restrictive of any subject matter claimed.

DETAILED DESCRIPTION

It has been surprisingly discovered that the synergistic combination of citric acid and urea compounds can be used before, during, and/or after a process for altering the color of the hair, in order to improve the strength and/or condition of the hair relative to processes that do not include the combination. Therefore, the disclosure relates to compositions for treating and/or caring for hair in conjunction with a process for altering the color of the hair, hair-color altering compositions, kits comprising the compositions, and methods of using the compositions.

I. Compositions

In various embodiments, the compositions according to the disclosure are compositions for conditioning, treating, and/or caring for hair before, during, and/or after a hair-color altering process. In other embodiments, the compositions according to the disclosure are compositions for altering the color of the hair. Such hair color altering compositions can be, in various embodiments, bleach compositions, temporary, demi- or semi-permanent hair color compositions, or permanent hair color compositions. In each case, the compositions comprise a synergistic combination of citric acid and urea compounds.

A. Synergistic Combination of Citric Acid and Urea Compounds

Compositions according to the disclosure comprise a surprisingly synergistic combination of citric acid and at least one urea compound chosen from urea and/or derivatives thereof. The synergistic combination of citric acid and urea compounds can be included in a hair conditioning, care, or treatment composition, can be included in a bleach composition, a developer composition, or a hair (color) base composition, or may be in a separate composition, without limitation on the form thereof, that may be added to any of the aforementioned compositions or any mixture thereof.

As used herein, a "urea compound" refers to urea or a urea derivative chosen from compounds of the following formula (I):

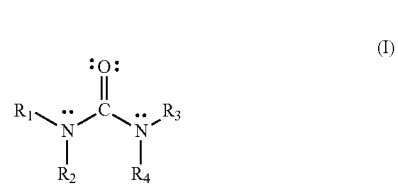

wherein $R_1$, $R_2$, $R_3$, and $R_4$ are independently chosen from hydrogen, $C_4$ to $C_{10}$ substituted or unsubstituted aryl groups, $C_2$ to $C_{10}$ substituted or unsubstituted heterocycle groups, $C_1$ to $C_{10}$ substituted or unsubstituted alkyl groups, and $C_3$ to $C_{10}$ substituted or unsubstituted cycloalkyl groups.

Non-limiting examples of suitable urea derivatives include imidazolidinyl urea, diazolidinyl urea, m-dimethylaminophenyl urea, dimethyl urea, a hydroxyethyl urea, urea, urea derivatives, imidazolidinyl urea, diazolidinyl urea, m-dimethylaminophenyl urea, dimethyl urea, a hydroxyethyl urea, N-(2-hydroxyethyl) urea; N-(2-hydroxypropyl) urea; N-(3-hydroxypropyl) urea; N-(2,3-dihydroxypropyl) urea; N-(2,3,4,5,6-pentahydroxyhexyl)-urea; N-methyl-N-(1,3,4,5,6-pentahydroxy-2-hexyl) urea; N-methyl-N'-(1-hydroxy-2-methyl-2-propyl) urea; N-(1-hydroxy-2-methyl-2-propyl) urea; N-(1,3-dihydroxy-2-propyl) urea; N-(trishydroxymethylmethyl) urea; N-ethyl-N'-(2-hydroxyethyl) urea; N,N-bis(2-hydroxyethyl) urea; N,N'-bis(2-hydroxyethyl) urea; N,N-bis(2-hydroxypropyl) urea; N,N'-bis(2-hydroxypropyl) urea; N,N-bis(2-hydroxyethyl)-N'-propylurea; N,N-bis(2-hydroxypropyl)-N'-(2-hydroxyethyl) urea; N-tert-butyl-N'-(2-hydroxyethyl)-N'-(2-hydroxy-propyl) urea; N-(1,3-dihydroxy-2-propyl)-N'-(2-hydroxyethyl) urea; N,N-bis(2-hydroxy-ethyl)-N',N'-dimethylurea; N,N,N',N'-tetrakis(2-hydroxyethyl) urea; N',N'-bis(2-hydroxy-ethyl)-N', and N'-bis(2-hydroxypropyl) urea.

In some embodiments, the at least one urea compound in the combination with citric acid is chosen from urea, dimethyl urea, hydroxyethyl urea, or mixtures thereof. In certain preferred embodiments, the at least one urea compound comprises, consists essentially of, or consists of hydroxyethyl urea.

As used herein, the term "citric acid" includes salts of citric acid, whether or not expressly stated. In various exemplary embodiments, the total amount of citric acid, salts thereof, or mixtures thereof (referred to herein collectively as "citric acid") that may be included in the compositions disclosed herein may range from about 0.1% to about 50%, including all subranges therebetween, such as from about 0.5% to about 40%, about 0.5% to about 35%, about 0.5% to about 30%, about 0.5% to about 35%, about 0.5% to about 30%, about 0.5% to about 25%, about 0.5% to about 20%, about 0.5% to about 15%, about 0.5% to about 12%, about 0.5% to about 10%, about 0.5% to about 8%, about 0.5% to about 6%, about 0.5% to about 5%, about 0.5% to about 4%, about 0.5% to about 3%, about 0.5% to about 2%, about 0.8% to about 40%, about 0.8% to about 35%, about 0.8% to about 30%, about 0.8% to about 35%, about 0.8% to about 30%, about 0.8% to about 25%, about 0.8% to about 20%, about 0.8% to about 15%, about 0.8% to about 12%, about 0.8% to about 10%, about 0.8% to about 8%, about 0.8% to about 6%, about 0.8% to about 5%, about 0.8% to about 4%, about 0.8% to about 3%, about 0.8% to about 2%, about 0.5% to about 40%, about 0.5% to about 35%, about 0.5% to about 30%, about 0.5% to about 20%, about 0.5% to about 10%, about 0.5% to about 8%, about 1% to about 25%, about 1% to about 20%, about 1% to about 15%, about 1% to about 12%, about 1% to about 15%, about 1% to about 10%, about 1% to about 8%, about 1% to about 6%, about 1% to about 5%, about 1% to about 4%, about 1% to about 3%, about 1% to about 2%, about 1.2% to about 15%, about 1.2% to about 12%, about 1.2% to about 10%, about 1.2% to about 8%, about 1.2% to about 6%, about 1.2% to about 5%, about 1.2% to about 4%, about 1.2% to about 3%, or about 1.2% to about 2% based on the total weight of the composition. In some embodiments, the amount of citric acid is greater than about 0.5%, such as greater than about 1%, for example ranges from about 1% to about 10%, and for example ranges from about 1% to about 5%, from about 1% to about 4%, or from about 1% to about 3.5% by weight, or ranges from greater than 1% to about 10%, for example from greater than 1% to about 5%, from greater than 1% to about 4%, or from greater than 1% to about 3.5% by weight, relative to the total weight of the composition. In further embodiments, the amount of citric acid present in the composition is about 1%, about 1.2%, about 1.4%, about 1.6%, about 1.8%, about 2%, about 2.25%, or about 2.5% by weight, relative to the total weight of the composition, or is chosen from a range using any of the foregoing as upper and lower limits.

In various exemplary embodiments, the total amount of urea, urea derivatives, and mixtures thereof (referred to herein collectively as "urea compounds") that may be included in the compositions disclosed herein may range from about 0.01% to about 25%, including all subranges therebetween, such as from about 0.1% to about 20%, from about 0.1% to about 18%, from about 0.1% to about 15%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, about 0.2% to about 20%, from about 0.2% to about 18%, from about 0.2% to about 15%, from about 0.05% to about 10%, from about 0.05% to about 9%, from about 0.05% to about 8%, from about 0.05% to about 7%, from about 0.05% to about 6%, from about 0.05% to about 5%, from about 0.05% to about 4%, from about 0.05% to about 3%, from about 0.05% to about 2%, from about 0.1% to about 15%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.2% to about 15%, from about 0.2% to about 10%, from about 0.2% to about 9%, from about 0.2% to about 8%, from about 0.2% to about 7%, from about 0.2% to about 6%, from about 0.2% to about 5%, from about 0.2% to about 4%, from about 0.2% to about 3%, from about 0.2% to about 2%, from about 0.4% to about 20%, from about 0.4% to about 18%, from about 0.4% to about 15%, from about 0.4% to about 10%, from about 0.4% to about 9%, from about 0.4% to about 8%, from about 0.4% to about 7%, from about 0.4% to about 6%, from about 0.4% to about 5%, from about 0.4% to about 4%, from about 0.4% to about 3%, from about 0.4% to about 2%, or from about 0.4% to about 1.5% by weight, or is about 0.5%, about 0.8%, about 1%, about 1.2%, about 1.4%, about 1.6%, about 1.8%, or about 2% by weight, relative to the total weight of the composition, or is chosen from a range using any of the foregoing as upper and lower limits.

In some embodiments, the compositions comprise a total amount of citric acid ranging from about 1% to about 10%, for example from about 1% to about 7%, from about 1% to about 5%, or from about 1% to about 3.5% by weight, and a total amount of urea compounds ranging from about 0.05% to about 5%, for example from about 0.1% to about 4%, from about 0.2% to about 3%, or from about 0.3% to about 2% by weight, relative to the total weight of the composition.

In various embodiments, the amounts of citric acid and urea compounds may be chosen so that the weight ratio of the total amount of citric acid to the total amount of urea compounds allows the combination thereof to provide optimal benefits. In various embodiments, citric acid may be included in an amount of at least about the same or greater than the amount of urea compounds. For instance, in certain embodiments, the weight ratio of the total amount of citric acid to the total amount of urea compounds may range from about 1:1 to about 1:0.05, including all subranges therebetween, such as from about 1:0.95 to about 1:0.1, from about 1:0.95 to about 1:0.2, from about 1:0.95 to about 1:0.4, from about 1:0.95 to about 1:0.6, from about 1:0.95 to about 1:0.8, from about 1:0.9 to about 1:0.1, from about 1:0.9 to about 1:0.2, from about 1:0.9 to about 1:0.4, from about 1:0.9 to about 1:0.6, from about 1:0.85 to about 1:0.05, from about 1:0.85 to about 1:0.1, from about 1:0.85 to about 1:0.3, from about 1:0.85 to about 1:0.4, from about 1:0.85 to about 1:0.6, from about 1:0.8 to about 1:0.05, from about 1:0.8 to about 1:0.1, from about 1:0.8 to about 1:0.2, from about 1:0.8 to about 1:0.3, from about 1:0.8 to about 1:0.4, from about 1:0.8 to about 1:0.5, or from about 1:0.8 to about 1:0.6. In some embodiments, the weight ratio of the total amount of citric acid to the total amount of urea compounds is about 1:0.25, about 1:0.3, about 1:0.35, about 1:0.4, about 1:0.45, about 1:0.5, about 1:0.55, about 1:0.6, about 1:0.65, about 1:0.7, about 1:0.75, or about 1:0.8, or may be chosen from a range using any of the foregoing as upper and lower limits.

In some embodiments, the composition may be formulated to have a weight ratio of the total amount of citric acid to the total amount of urea compounds ranging from about 10:1 to about 1:10. In some instances, the composition may be formulated to have a weight ratio of the total amount of citric acid to the total amount of urea compounds ranging from about 10:1 to about 0.5:10, about 9:1 to about 0.5:10, about 8:1 to about 0.5:10, about 7:1 to about 0.5:10, about 6:1 to about 0.5:10, about 5:1 to about 0.5:10, about 4:1 to about 0.5:10, about 3:1 to about 0.5:10; 10:1 to about 1:10, about 9:1 to about 1:10, about 8:1 to about 1:10, about 7:1 to about 1:10, about 6:1 to about 1:10, about 5:1 to about 1:10, about 4:1 to about 1:10, about 3:1 to about 1:10; 10:1 to about 2:10, about 9:1 to about 2:10, about 8:1 to about 2:10, about 7:1 to about 2:10, about 6:1 to about 2:10, about 5:1 to about 2:10, about 4:1 to about 2:10, about 3:1 to about 2:10; about 10:1 to about 2:8, about 9:1 to about 2:8, about 8:1 to about 2:8, about 7:1 to about 2:8, about 6:1 to about 2:8, about 5:1 to about 2:8, about 4:1 to about 2:8, about 3:1 to about 2:8; about 10:1 to about 2:6, about 9:1 to about 2:6, about 8:1 to about 2:6, about 7:1 to about 2:6, about 6:1 to about 2:6, about 5:1 to about 2:6, about 4:1 to about 2:6, about 3:1 to about 2:6; about 3:1 to about 1:10, about 3:1 to about 1:9, about 3:1 to about 1:8, about 3:1 to about 1:7, about 3:1 to about 1:6, about 3:1 to about 2:10, about 3:1 to about 2:9, about 3:1 to about 2:8, about 3:1 to about 2:7, about 3:1 to about 2:6, about 3:1 to about 2:5, about 3:1 to about 2:4, or about 3:1 to about 2:3, about 2:1 to about 2:10, about 1:1 to about 2:10, about 3:1 to about 2:9, about 3:1 to about 2:8, about 3:1 to about 2:7, about 3:1 to about 2:6, about 3:1 to about 2:5, about 3:1 to about 2:4, or about 3:1 to about 2:3 including ranges and sub-ranges there between (e.g., about 3:1 to about 2:5, about 2:1 to about 2:5, about 1:1 to about 2:5, about 1:1 to about 2:4, etc.).

The composition may be formulated to have a mole ratio of the citric acid to the urea compound that may range from about 10:1 to about 0.5:10. In some instances, the composition may be formulated to have a weight ratio of citric acid to urea compound(s) of 10:1 to about 0.5:10, about 9:1 to about 0.5:10, about 8:1 to about 0.5:10, about 7:1 to about 0.5:10, about 6:1 to about 0.5:10, about 5:1 to about 0.5:10, about 4:1 to about 0.5:10, about 3:1 to about 0.5:10; 10:1 to about 1:10, about 9:1 to about 1:10, about 8:1 to about 1:10, about 7:1 to about 1:10, about 6:1 to about 1:10, about 5:1 to about 1:10, about 4:1 to about 1:10, about 3:1 to about 1:10; about 10:1 to about 2:10, about 9:1 to about 2:10, about 8:1 to about 2:10, about 7:1 to about 2:10, about 6:1 to about 2:10, about 5:1 to about 2:10, about 4:1 to about 2:10, about 3:1 to about 2:10; about 10:1 to about 2:8, about 9:1 to about 2:8, about 8:1 to about 2:8, about 7:1 to about 2:8, about 6:1 to about 2:8, about 5:1 to about 2:8, about 4:1 to about 2:8, about 3:1 to about 2:8; about 10:1 to about 2:6, about 9:1 to about 2:6, about 8:1 to about 2:6, about 7:1 to about 2:6, about 6:1 to about 2:6, about 5:1 to about 2:6, about 4:1 to about 2:6, about 3:2 to about 2:6; about 2:1 to about 2:10, about 1:1 to about 2:10, about 3:2 to about 2:9, about 3:2 to about 2:8, about 3:2 to about 2:7, about 3:2 to about 2:6, about 3:2 to about 2:5, about 3:2 to about 2:4, about 3:2 to about 2:3, about 1:1 to about 1:4, about 1:1 to about 1:3, about 1:1 to about 1:2, or about 1:1.3 to about 1:1.6, including ranges and sub-ranges therebetween (e.g., about 3:2 to about 2:5, about 2:1 to about 2:5, about 1:1 to about 2:5, about 1:1 to about 2:4, etc.).

In some other embodiments, the mole ratio of citric acid to urea compounds may range from about 0.3 to about 2.5, for example from 0.3 to about 2.0, from about 0.4 to about 1.5, or from 0.5 to about 1.4, or may be about 0.45, about 0.6, about 0.7, about 0.75, about 0.8, or about 0.9.

In some embodiments, the combination of citric acid and the at least one urea compound may be in the form of a pre-phase mixture (pre-mix). For example, the combination of citric acid and at least one urea compound may be produced by combining and mixing particular amounts of citric acid and urea compounds with specific mole and/or weight ratios as described herein to form a mixture. The pre-phase mixture can be added to a base composition comprising other cosmetic ingredients to produce compositions according to the disclosure for caring for, conditioning, and/or treating hair, such as curly hair. In some embodiments, however, the citric acid and at least one urea compound are not prepared as a pre-phase mixture.

In various exemplary embodiments, the total amount of the pre-phase mixture of citric acid and at least one urea compound may be included in a composition according to the disclosure in an amount ranging from about 0.5% to about 50%, including all ranges and subranges therebetween, such as from about 0.5% to about 40%, from about 0.5% to about 30%, from about 0.5% to about 20%, from about 0.5% to about 15%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3.5%, from about 1% to about 50%, from about 1% to about 40%, from about 1% to about 30%, from about 1% to about 20%, from about 1% to about 15%, from about 1% to about 10%, from about 1% to about 9%, from about 1% to about 8%, from about 1% to about 7%, from about 1% to about 6%, from about 1% to about 5%, from about 1% to about 4%, from about 1% to about 3.5%, from about 1.5% to about 50%, from about 1.5% to about 40%, from about 1.5% to about 30%, from about 1.5% to about 20%, from about 1.5% to about 15%, from about 1.5% to about 10%, about 1.5% to about 9%, about 1.5% to about 8%, about 1.5% to about 7%, about 1.5% to about 6%, from about 1.5% to about 5%, from about 1.5% to about 4%, from about 1.5% to about 3.5%, from about 2% to about 50%, from about 2% to about 40%, from about 2% to about 30%, from about 2% to about 20%, from about 2% to about 15%, from about 2% to about 10%, from about 2% to about 9%, from about 2% to about 8%, from about 2% to about 7%, from about 2% to about 6%, from about 2% to about 5%, from about 2% to about 4%, from about 2% to about 3.5%, from about 2.5% to about 50%, from about 2.5% to about 40%, from about 2.5% to about 30%, from about 2.5% to about 20%, from about 2.5% to about 15%, from about 2.5% to about 10%, about 2.5% to about 9%, about 2.5% to about 8%, about 2.5% to about 7%, about 2.5% to about 6%, from about 2.5% to about 5%, from about 2.5% to about 4%, from about 2.5% to about 3.5%, from about 3% to about 50%, from about 3% to about 40%, from about 3% to about 30%, from about 3% to about 20%, from about 3% to about 15%, from about 3% to about 10%, from about 3% to about 9%, from about 3% to about 8%, from about 3% to about 7%, from about 3% to about 6%, from about 3% to about 5%, from about 3% to about 4%, from about 3% to about 3.5%, from about 3.5% to about 50%, from about 3.5% to about 40%, from about 3.5% to about 30%, from about 3.5% to about 20%, from about 3.5% to about 15%, from about 3.5% to about 10%, about 3.5% to about 9%, about 3.5% to about 8%, about 3.5% to about 7%, about 3.5% to about 6%, from about 3.5% to about 5%, from about 4% to about 50%, from about 4% to about 40%, from about 4% to about 30%, from about 4% to about 20%, from about 4% to about 15%, from about 4% to about 10%, from about 4% to about 9%, from about 4% to about 8%, from about 4% to about 7%, from about 4% to about 6%, or from about 4% to about 5%, or is about 1%, about 2%, about 3%, about 4%, or about 5% by weight, relative to the total weight of the composition. In some embodiments, the total amount of the pre-phase mixture of citric acid and at least one urea compound included in a composition disclosed herein is about 3.1%, about 3.2%, about 3.3%, about 3.4%, or about 3.5% by weight, relative to the total weight of the composition, including all ranges and subranges thereof, and in other embodiments the total amount of the combination of citric acid and at least one urea compound included in a composition disclosed herein is about 4.8%, about 4.9%, about 5.0%, about 5.1%, or about 5.2% by weight, relative to the total weight of the composition, including all ranges and subranges thereof.

In some embodiments, an exemplary composition disclosed herein comprises any of the above ranges, for example from about 0.5% to about 10%, from about 1% to about 7%, from about 2% to about 6%, or from about 3% to about 5.5%, for example is about 3.3% or about 5%, of a pre-phase mixture of citric acid and hydroxyethyl urea, where a weight ratio of citric acid to hydroxyethyl urea in the pre-phase mixture ranges from about 1:1 to about 1:0.05, such as about 1:1 to about 1:0.5, or is about 1:0.75, corresponding to a mole ratio of citric acid to hydroxyethyl urea that is about 1:1.4.

Without limitation, the combination of citric acid and urea compounds may be included in a hair care/treatment composition, a temporary hair color altering composition, or a permanent hair color altering composition, in order to provide strength and sensorial benefits to hair that is subjected to a process for altering the color thereof. In some embodiments, the combination of citric acid and urea compounds may be added to the hair care/treatment composition, temporary hair color altering composition, or permanent hair color altering composition at or near the time of use.

For example, in some embodiments, the combination of citric acid and the at least one urea compound may be in the form of a pre-phase mixture as described above. The pre-phase mixture can subsequently be added to a hair care/treatment composition, temporary hair color altering composition, or permanent hair color altering composition to produce the compositions according to the disclosure for use before, during, and/or after altering the color of the hair. In some embodiments, however, the citric acid and at least one urea compound are not prepared as a pre-phase mixture, but are included in the composition, e.g. upon manufacture.

B. Hair Conditioning/Care/Treatment Compositions

Hair conditioning, care, or treatment compositions comprise, in addition to a synergistic combination of citric acid and urea compounds, one or more components that are beneficial for conditioning, caring for, and/or treating hair. Such components include, but are not limited to, silicone compounds, fatty compounds, cationic polymers, cationic surfactants, and the like. Such compositions may be useful to treat the hair before, during, and/or after a process for altering the color of the hair, in order to reduce or repair damage typically caused by hair color altering compositions and processes. The hair care/treatment compositions described herein have been found to impart strength as well as smoothness, softness, shine, reduced frizz, curl retention, and/or curl definition to the hair when used before, during, and/or after a process for altering the color of hair.

The citric acid and urea compounds may be included in the hair conditioning, care, or treatment compositions in amounts and ratios as described above.

Silicone Compounds

Compositions according to the disclosure may optionally comprise at least one silicone compound. Without intending to be limited by theory, the silicone compounds may provide treatment or care benefits such as flexibility, manageability, discipline, an overall softer end feel, etc., to the hair. Thus, in some embodiments, the compositions comprise at least one silicone compound, particularly compositions for providing conditioning, treatment, or care benefits to the hair. By way of example only, the at least one silicone compound may be chosen from dimethicone, dimethicone copolyols, dimethicone copolymers, amino functional silicones, or mixtures thereof.

In some embodiments, the at least one silicone compound is chosen from dimethicone copolyols. Dimethicone copolyol is a general term used for a group of polymers made from dimethicone and polyoxyethylene and/or polyoxypropylene. Suitable examples of dimethicone copolyols include Dimethicone PEG-8 Adipate, Dimethicone PEG-8 Benzoate, Dimethicone PEG-7 Phosphate, Dimethicone PEG-8 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and mixtures thereof.

In some embodiments, the at least one silicone compound may be an amino functional silicone. In an embodiment, the at least one silicone compound of the disclosure is amino functional silicone comprising at least one functionalized amodimethicone. The term "amino functional silicone" as used herein can mean any silicone comprising at least one primary, secondary or tertiary amine or a quaternary ammonium group (i.e., a quaternized group).

Non-limiting examples of amino functional silicone that may be used include:

a) polysiloxanes corresponding to formula (A):

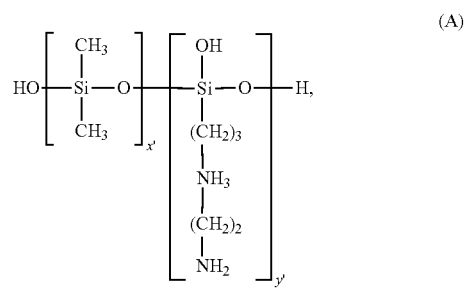

wherein x' and y' are integers such that the weight-average molecular weight (Mw) ranges from about 5000 to about 500 000;

b) amino silicones corresponding to formula (B):

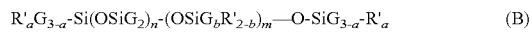

wherein:
G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10; and R', which may be identical or different, denote a monovalent radical having formula —$C_qH_{2q}L$, in which q is a number ranging from 2 to 8 and L is an optionally quaternized amino group chosen from the following groups:

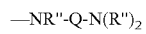

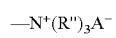

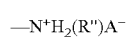

in which:
- R", which may be identical or different, denotes hydrogen, phenyl, benzyl, or a saturated monovalent hydrocarbon-based radical, for example a $C_1$-$C_{20}$ alkyl radical;
- Q denotes a linear or branched $C_rH_{2r}$ group, r being an integer ranging from 2 to 6, for example from 2 to 4; and
- $A^-$ represents a cosmetically acceptable ion, in particular a halide such as fluoride, chloride, bromide or iodide.

A group of amino silicones corresponding to formula (B) is represented by the silicones called "trimethylsilylamodimethicone" having formula (C):

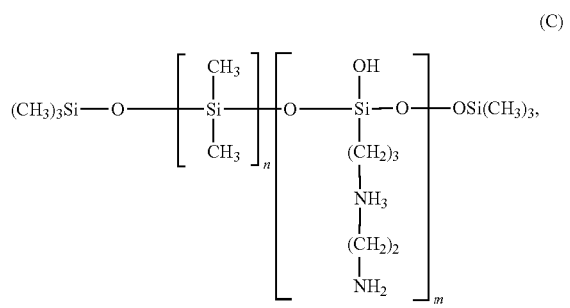

in which n and m have the meanings as in formula B.

Another group of amino silicones corresponding to formula (B) is represented by silicones of formula (D):

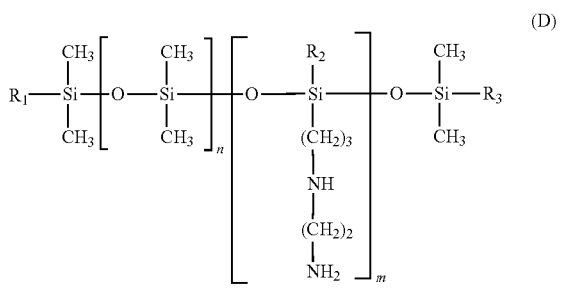

wherein:
- m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5; and
- R1, R2, and R3, which may be identical or different, represent a hydroxy or C1-C4 alkoxy radical, where at least one of the radicals R1 to R3 denotes an alkoxy radical.

In one embodiment, the alkoxy radical a methoxy radical. In further embodiments, the hydroxy/alkoxy mole ratio ranges from 0.2:1 to 0.4:1 or from 0.25:1 to 0.35:1 or is 0.3:1. In various embodiments, the weight-average molecular weight (Mw) of the silicone ranges from 2000 to 1,000,000, such as from 3500 to 200,000.

Another group of amino silicones corresponding to formula (B) is represented by silicones of formula (E):

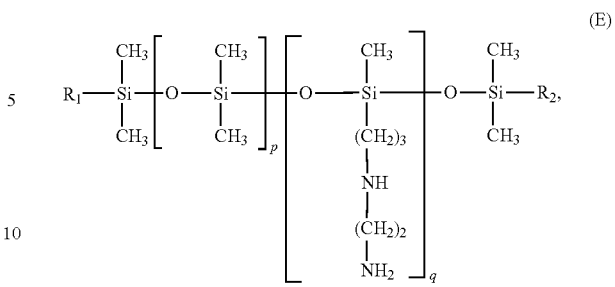

wherein:
- p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5; and
- $R_1$ and $R_2$, which are different, represent a hydroxy or $C_1$-$C_4$ alkoxy radical, where at least one of the radicals $R_1$ or $R_2$ denotes an alkoxy radical.

In one embodiment, the alkoxy radical is a methoxy radical. In further embodiments, the hydroxy/alkoxy mole ratio ranges generally from 1:0.8 to 1:1.1 or from 1:0.9 to 1:1, or is 1:0.95. In various embodiments, the weight-average molecular weight (Mw) of the silicone ranges from 2000 to 200,000, even more particularly 5000 to 100,000 and more particularly from 10,000 to 50,000.

Commercial products corresponding to these silicones having structure (D) or (E) may include in their composition one or more other amino silicones whose structure is different than formulae (D) or (E). For example, a product containing amino silicones having structure (D) is sold by Wacker under the name Belsil® ADM 652, and products containing amino silicones having structure (E) include those sold by Wacker under the names Fluid WR 1300® or Finish CT 96 ER or SLM 28020®.

Another group of amino silicones corresponding to formula (B) is represented by the following formula (F), which is optionally linear:

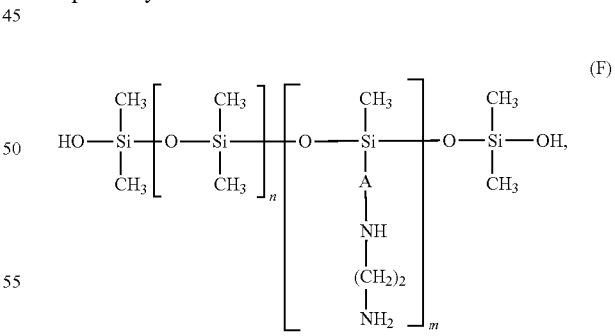

wherein:
- m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10; and
- A denotes a linear or branched alkylene radical containing from 4 to 8 carbon atoms, for example 4 carbon atoms.

The weight-average molecular weight (Mw) of these amino silicones may range from 2000 to 1,000,000 such as from 3500 to 200,000. A preferred silicone of formula (F) is amodimethicone (INCI name) sold under the tradename XIAMETER® MEM-8299 Cationic Emulsion by Dow Corning or sold under the tradename SILSOFT 253, by Momentive Performance Materials.

Another group of amino silicones corresponding to formula (B) is represented by the following formula (G), which is optionally branched:

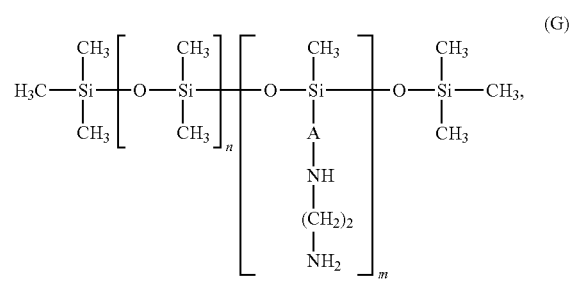

wherein:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10; and
A denotes a linear or branched alkylene radical containing from 4 to 8 carbon atoms, for example 4 carbon atoms.

The weight-average molecular weight (Mw) of these amino silicones may range from 500 to 1,000,000 such as from 1000 to 200,000. Commercially available silicones having this formula include DC2-8566 Amino Fluid by Dow Corning.

c) amino silicones corresponding to formula (H):

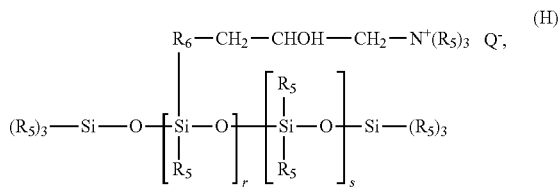

wherein:
R5 represents a monovalent hydrocarbon-based radical containing from 1 to 18 carbon atoms, and in particular a $C_1$-$C_{18}$ alkyl or $C_2$-$C_{18}$ alkenyl radical, for example methyl;
R6 represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an Si—C bond;

$Q^-$ is an anion such as a halide ion, in particular chloride, or an organic acid salt (for example acetate);
r represents a mean statistical value from 2 to 20 and in particular from 2 to 8; and
s represents a mean statistical value from 20 to 200 and in particular from 20 to 50.

d) quaternary ammonium silicones having formula (I):

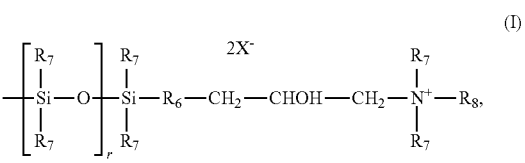

wherein:
$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;
$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an Si—C bond;
$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;
$X^-$ is an anion such as a halide ion, in particular chloride, or an organic acid salt (for example acetate); and
r represents a mean statistical value from 2 to 200 and in particular from 5 to 100.

Examples of such silicones are described, for example, in EP-A 0 530 974.

e) amino silicones having formula (J):

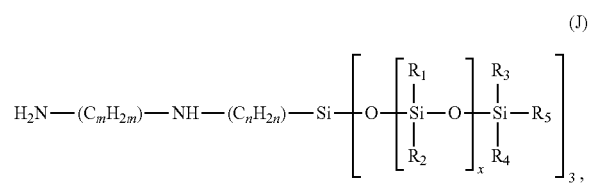

wherein:
$R_1$, $R_2$, $R_3$ and $R_4$, which may be identical or different, denote a $C_1$-$C_4$ alkyl radical or a phenyl group;
$R_5$ denotes a $C_1$-$C_4$ alkyl radical or a hydroxyl group;
n is an integer ranging from 1 to 5;
m is an integer ranging from 1 to 5; and
x is chosen such that the amine number is between 0.01 and 1 meq/g.

f) multiblock polyoxyalkylenated amino silicones of type $(AB)_n$, A being a polysiloxane block and B being a polyoxyalkylenated block containing at least one amine group. In various embodiments, such silicones may comprise repeating units having one of the following general formulae:

[—(SiMe$_2$O)$_x$SiMe$_2$-R—N(R'')—R'—O(C$_2$H$_{40}$)$_a$
(C$_3$H$_6$O)b-R'—N(H)—R—]

[—(SiMe$_2$O)$_x$SiMe$_2$-R—N(R'')—R'—O(C$_2$H$_{40}$)$_a$
(C3H$_6$O)b-]

wherein:
   a is an integer greater than or equal to 1, for example ranging from 5 to 200, more particularly ranging from 10 to 100;
   b is an integer comprised between 0 and 200, for example ranging from 4 to 100, more particularly between from 5 and 30;
   x is an integer ranging from 1 to 10,000, more particularly from 10 to 5000;
   R'' is a hydrogen atom or a methyl;
   R, which may be identical or different, represent a divalent linear or branched C$_2$-C$_{12}$ hydrocarbon-based radical, optionally including one or more heteroatoms such as oxygen; for example, R may denote an ethylene radical, a linear or branched propylene radical, a linear or branched butylene radical, or a —CH$_2$CH$_2$CH$_2$OCH(OH)CH$_2$— radical; | preferentially R denotes a —CH$_2$CH$_2$CH$_2$OCH(OH)CH$_2$— radical; and
   R', which may be identical or different, represent a divalent linear or branched C$_2$-C$_{12}$ hydrocarbon-based radical, optionally including one or more heteroatoms such as oxygen; for example, R' may denote an ethylene radical, a linear or branched propylene radical, a linear or branched butylene radical, or a —CH$_2$CH$_2$CH$_2$OCH(OH)CH$_2$— radical; preferentially R' denotes —CH(CH$_3$)—CH$_2$—.

The siloxane blocks may, for example, represent from 50-95 mol % of the total weight of the silicone, more particularly from 70-85 mol %. The amine content may range from 0.02 to 0.5 meq/g of copolymer in a 30% solution in dipropylene glycol, more particularly from 0.05 to 0.2. The weight-average molecular weight (Mw) of the silicone may, for example, range from 5000 to 1,000,000, more particularly from 10,000 to 200,000. Non-limiting examples include bis-amino PEG/PPG-41/3 aminoethyl PG-propyl dimethicone and PEG-40/PPG-8 methylaminopropyl hydroxypropyl dimethicone copolymer. Commercially available products include the silicones sold under the names SILSOFT A-843 or SILSOFT A+ by Momentive.
   g) the alkylamino silicones corresponding to formula (K) below:

$$R_1-Si(CH_3)_2-[O-Si(CH_3)_2]_x-[O-Si(CH_3)(A-NH-(CH_2)_2-NH_2)]_y-O-Si(CH_3)_2-R_2 \quad (K)$$

wherein:
   x and y are numbers ranging from 1 to 5000; for example, x ranges from 10 to 2000 and especially from 100 to 1000; for example, y ranges from 1 to 100;
   R$_1$ and R$_2$, which may be identical or different, preferably identical, are linear or branched, saturated or unsaturated alkyl radicals, comprising 6 to 30 carbon atoms, for example 8 to 24 carbon atoms and especially 12 to 20 carbon atoms; and
   A denotes a linear or branched alkylene radical containing from 2 to 8 carbon atoms.

In various exemplary embodiments, A comprises from 3 to 6 carbon atoms, especially 4 carbon atoms, and in certain embodiments, A is branched. Mention may be made of the following divalent radicals: —CH$_2$CH$_2$CH$_2$— and —CH$_2$CH(CH$_3$)CH$_2$—.

Optionally, R$_1$ and R$_2$, which may be identical or different, are saturated linear alkyl radicals comprising 6 to 30 carbon atoms, for example 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R$_1$ and R$_2$, which may be identical or different, are chosen from hexadecyl (cetyl) and octadecyl (stearyl) radicals.

In various exemplary embodiments, the silicone of formula (K) is chosen such that:
   x ranges from 10 to 2000 and especially from 100 to 1000;
   y ranges from 1 to 100;
   A comprises 3 to 6 carbon atoms and especially 4 carbon atoms; optionally, A is branched; and more particularly A is chosen from the following divalent radicals: CH$_2$CH$_2$CH$_2$ and —CH$_2$CH(CH$_3$)CH$_2$—; and
   R$_1$ and R$_2$, which may be identical or different, are linear, saturated alkyl radicals comprising 6 to 30 carbon atoms, for example 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, R$_1$ and R$_2$, which may be identical or different, being chosen from hexadecyl (cetyl) and octadecyl (stearyl) radicals.

An exemplary amino silicone of formula (K) is bis-cetearylamodimethicone (INCI name), such as the silicone sold under the name SILSOFT AX by Momentive.

Additional useful amino silicones include h) silicone compounds with at least one quaternary ammonium group. Suitable non-limiting examples are quaternium-80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium-80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. For example, quaternium-80, silicone quaternium-16, silicone quaternium-18, silicone quaternium-15, or mixtures thereof may be chosen.

The amount of the at least one silicone compound that may be included in various embodiments can vary, but typically ranges from about 0.01% to about 10%, based on the total weight of the composition, including all ranges and subranges therebetween. For example, the total amount of silicone compounds may range from about 0.01% to about 8%, from about 0.01% to about 5%, from about 0.01% to about 4%, from about 0.01% to about 3%, from about 0.01% to about 2%, from about 0.1% to about 10%, from about 0.1% to about 8%, from about 0.1% to about 5%, from about 0.1% to about 4%, from about 0.1% to about 3%, from about 0.1% to about 2%, from about 0.5% to about 10%, from about 0.5% to about 8%, from about 0.5% to about 5%, from about 0.5% to about 4%, from about 0.5% to about 3%, from about 0.5% to about 2%, from about 1% to about 10%, from about 1% to about 8%, from about 1% to about 5%, from about 1% to about 4%, from about 1% to about 3%, or from about 1% to about 2%, by weight, relative to the total weight of the composition. In some preferred embodiments, the total amount of silicones may range from about 0.1% to about 5%, or about 0.3% to about 4% by weight, relative to the total weight of the composition.

In one embodiment, the amount of silicone compounds is about 10% or less, such as about 5% or less, such as about 0.2%, about 0.3%, about 0.5%, about 1%, about 1.5%, about 2%, about 2.5%, about 3%, about 3.5%, about 4%, about 4.5%, or about 5%, by weight, relative to the total weight of the composition.

Fatty Compounds

Compositions according to the disclosure may optionally comprise at least one fatty compound other than silicone compounds (referred to simply as "fatty compound" or "fatty compounds" herein). Non-limiting examples of suitable fatty compounds include fatty alcohols, fatty esters, fatty ethers, fatty acids, wax, oils, and derivatives thereof.

Fatty Alcohols

Suitable fatty alcohols, if present, include those having a fatty group with a carbon chain of greater than 8 carbon atoms, such as, for example, from 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is optionally hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, or mixtures thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, or mixtures thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bonds), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or about 15 to about 35 mores, including all ranges and subranges therebetween, of alkylene oxide per mole of alkoxylated fatty alcohol.

As non-limiting examples of alkoxylated fatty alcohols, steareth (for example, steareth-2, steareth-20, steareth-21, and steareth-100), laureth (for example, laureth-4, laureth-7, and laureth-12), ceteth (for example, ceteth-10 and ceteth-20) and ceteareth (for example, ceteareth-2, ceteareth-7, ceteareth-10, ceteareth-20, and ceteareth-25) are mentioned.

Fatty Acids

Suitable fatty acids that can be included in the compositions disclosed herein may be include those having from about 10 to about 30 carbon atoms, from about 12 to about 22 carbon atoms, or from about 16 to about 22 carbon atoms. These fatty acids can be straight or branched chain acids and can be saturated or unsaturated. Also included are diacids, triacids, and other multiple acids which meet the carbon number requirement herein. Further included herein are salts of these fatty acids. Nonlimiting examples of fatty acids include myristic acid, lauric acid, palmitic acid, stearic acid, behenic acid, arichidonic acid, oleic acid, isostearic acid, sebacic acid, or mixtures thereof. In some embodiments, the fatty acids may comprise myristic acid, palmitic acid, stearic acid, or mixtures thereof.

Fatty Esters

The cosmetic compositions may include one or more fatty compound(s) that is a fatty ester. For example, the fatty compound(s) may be chosen from saturated or unsaturated, linear or branched C1-C26 aliphatic mono- or polyacids and of saturated or unsaturated, linear or branched C1-C26 aliphatic mono- or polyalcohols, the total carbon number of the esters more particularly being greater than or equal to 10.

In an embodiment, a fatty ester may be chosen from cetyl esters, isopropyl esters, glyceryl (glycerol) esters, dialkyl esters, diesters with octanoic acid and propylene glycol (for example, mixture of the propylene glycol diesters of caprylic and capric acids, propylene glycol dicaprylate/dicaprate, or mixtures thereof, and in some embodiments is chosen from cetyl esters, isopropyl esters, glyceryl esters, or mixtures thereof.

Additionally or alternatively, a fatty ester may be chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, diisostearyl fumarate, or mixtures thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

In some embodiments, a fatty ester may be chosen from dialkyl carbonates of formula $R_1O(C=O) R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, for example one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, or mixtures thereof.

Fatty Ethers

The fatty compounds may be chosen from fatty ethers. For example, the cosmetic composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Derivatives

When fatty compounds are mentioned, derivatives of fatty compounds are intended to be included whether or not so stated, unless expressly indicated otherwise.

Fatty alcohol derivatives include alkyl ethers of fatty alcohols, alkoxylated fatty alcohols, alkyl ethers of alkoxylated fatty alcohols, esters of fatty alcohols or mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohols, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; or mixtures thereof.

Non-limiting examples of polyglycerol esters of fatty acids include those of the following formula (III):

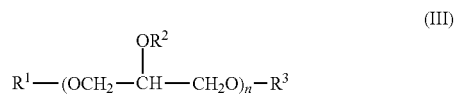

$$R^1-(OCH_2-CH-CH_2O)_n-R^3$$
$$\quad\quad\quad\quad\quad\;\; |$$
$$\quad\quad\quad\quad\quad OR^2$$

(III)

wherein:
the average value of n is about 3; and
$R^1$, $R^2$, and $R^3$, which may be identical or different, are independently chosen from a fatty acid moiety or hydrogen, provided that at least one of $R^1$, $R^2$, and $R^3$ is a fatty acid moiety.

For instance, $R^1$, $R^2$, and $R^3$ may be saturated or unsaturated, linear or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, or mixtures thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, or mixtures thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, or mixtures thereof. Preferred for use herein are glycerol monostearate, 12-hydroxy stearic acid, or mixtures thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, or 50° C. or higher. The high melting point fatty compound may be selected from fatty acids, fatty alcohol derivatives, fatty acid derivatives, or mixtures thereof. Nonlimiting examples of the high melting point compounds are found in the International Cosmetic Ingredient Dictionary, Sixteenth Edition, 2016, which is incorporated by reference herein in its entirety.

Non-Silicone Oils

In some embodiments, the fatty compounds may be chosen from non-silicone oils. The term "oil" as used herein describes any material which is substantially insoluble in water. Suitable non-silicone oils include, but are not limited to, natural oils; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C. and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity oils generally have a viscosity of 200-1,000,000, or 100,000-250,000, mPas at 25° C. Such oils include lanolin and lanolin derivatives, triisocetyl citrate, sorbitan sesquioleate, $C_{10}$-$C_{18}$ triglycerides, caprylic/capric/triglycerides, glyceryl triacetyl hydroxystearate, glyceryl triacetyl ricinoleate, glyceryl trioctanoate, mink oil, illipe butter, tallow, tricaprin, trihydroxystearin, triisostearin, trilaurin, trilinolein, trimyristin, triolein, tripalmitin, tristearin, cholesterol, or combinations thereof.

Vegetable oils that may be used according to the disclosure include, but are not limited to, coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, walnut oil, and mixtures thereof. In various embodiments, compositions according to the disclosure comprise coconut oil. In further embodiments, compositions according to the disclosure are substantially free of vegetable oils other than coconut oil. Thus, in various embodiments, the at least one vegetable oil may comprise, consist essentially of, or consist of coconut oil.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

In various embodiments, the total amount of fatty compounds in compositions disclosed herein may range from about 0.01% to about 30%, including all subranges therebetween, such as from about 0.1% to about 30%, about 0.1% to about 25%, about 0.1% to about 20%, about 0.1% to about 15%, about 0.1% to about 10%, about 0.1% to about 5%, about 0.5% to about 30%, about 0.5% to about 25%, about 0.5% to about 20%, about 0.5% to about 15%, about 0.5% to about 10%, about 0.5% to about 5%, about 1% to about 30%, about 1% to about 25%, about 1% to about 20%, about 1% to about 15%, about 1% to about 10%, about 1% to about 8%, about 1% to about 6%, about 1% to about 5%, about 2% to about 30%, about 2% to about 25%, about 2% to about 20%, about 2% to about 15%, about 2% to about 10%, about 2% to about 8%, about 2% to about 6%, about 2% to about 5%, about 3% to about 30%, about 3% to about 25%, about 3% to about 20%, about 3% to about 15%, about 3% to about 10%, about 3% to about 8%, about 3% to about 6%, about 3% to about 5%, about 4% to about 30%, about 4% to about 25%, about 4% to about 20%, about 4% to about 15%, about 4% to about 10%, about 4% to about 8%, about 4% to about 6%, about 4% to about 5%, about 5% to about 30%, about 5% to about 25%, about 5% to about 20%, about 5% to about 15%, about 5% to about 10%, about 5% to about 8%, or about 5% to about 6% by weight, relative to the total weight of the composition.

Cationic Surfactants

Compositions according to the disclosure may optionally include at least one cationic surfactant.

In certain embodiments, compositions disclosed herein may include at least one cationic surfactant chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyl-diethylamine, behenamidoethyldimethylamine, arachidamidopropyldimethylamine, arachidamidopropyidiethylamine, arachidamidoethyidiethylamine, arachidamidoethyl-dimethylamine, or mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylamino-ethylchloride hydrochloride, cysteine hydrochloride, diethanolammonium POE (10) oletyl ether phosphate, diethanolammonium POE (3) oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procaine-hydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

In some embodiment, the composition may optionally comprise at least one cationic surfactant chosen from polyoxyalkylenated, primary, secondary or tertiary fatty amines, or salts thereof, and quaternary ammonium salts, or mixtures thereof. In some cases, it is useful to use salts such as chloride salts of the quaternary ammonium compounds.

The fatty amines generally comprise at least one $C_8$-$C_{30}$ hydrocarbon-based chain. For example, quaternary ammonium salts, which may be incorporated in certain instances, include those corresponding to the following general formula (VIII):

(VIII)

wherein the groups $R_8$ to $R_{11}$, which may be identical or different, independently represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms such as from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (VIII), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltri-methylammonium salts, stearamidopropyltrimethylammonium salts, and stearamidopropyldimethyl-cetearylammonium salts.

Examples of quaternary ammonium salt of imidazoline, which may be incorporated in certain instances, include those having a structure according to the general formula (IX) provided below:

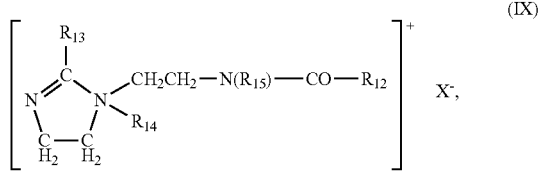
(IX)

in which R12 represents an alkenyl or alkyl group comprising from 8 to 30 carbon atoms, derived, for example, from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups optionally comprise, respectively, from 1 to 20 carbon atoms and from 6 to 30 carbon atoms. $R_{12}$ and $R_{13}$ may denote a mixture of alkenyl or alkyl groups containing from 12 to 21 carbon atoms, derived, for example, from tallow fatty acids, $R_{14}$ optionally denotes a methyl group, and $R_{15}$ optionally denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula (X):

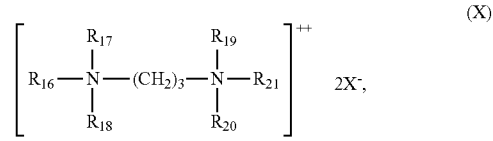
(X)

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group ($R_{16a}$) ($R_{17a}$)($R_{18a}$)N—($CH_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75).

Examples of cationic/cationizable surfactants, which may be incorporated in certain instances, include those having a structure in accordance with the general formula (XI) provided below:

R4-A-R5-B (XI)

wherein R4 is a saturated or unsaturated, straight, or branched alkyl chain with 8 to 24 carbon atoms, R5 is a straight or branched alkyl chain with 1 to 4 carbon atoms, A is selected from:

and B is selected from:

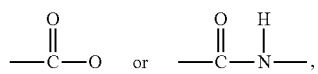

wherein $R_6$ and $R_7$, which are the same or different, are chosen from hydrogen or alkyl chains with 1 to 4 carbon atoms, hydroxyl alkyl chains with 1 to 4 carbon atoms, or di-hydroxyl alkyl chain with 2 to 4 carbon atoms,

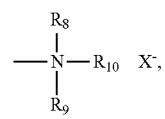

wherein $R_8$ and $R_9$, which are the same or different, are chosen from alkyl chains with 1 to 4 carbon atoms, hydroxyl alkyl chains with 1 to 4 carbon atoms, or di-hydroxyl alkyl chains with 2 to 4 carbon atoms; $R_{10}$ is chosen from alkyl chains with 1 to 4 carbon atoms, hydroxyl alkyl chains with 1 to 4 carbon atoms, or di-hydroxyl alkyl chains with 2 to 4 carbon atoms.

In some instances, $R_4$ in formula (XI) is a saturated or unsaturated, straight or branched alkyl chain with 10 to 24 carbon atoms, such as 12 to 22 carbon atoms, and $R_5$ is a straight or branched alkyl group with 1 to 4 carbon atoms, and A, B, and $R_6$ to $R_{10}$ are same as above.

Non-limiting suitable examples of cationic surfactants are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, for example, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyl-diethylamine, behenamidoethyl-dimethylamine, arachidamidopropyldimethylamine, arachidamidopropyidiethylamine, arachidamidoethyidiethylamine, arachidamidoethyl-dimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, or mixtures thereof. In particular, lactic acid or tartaric acid or mixtures thereof are useful, especially in combination with fatty dimethylamines such as, for example, stearamidopropyl dimethylamine.

In an embodiment, a composition disclosed herein may be formulated with a cationic surfactant chosen from behentrimonium chloride, cetrimonium chloride, behentrimonium methosulfate, or mixtures thereof.

The compositions disclosed herein may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

In yet another instance, the at least one cationic surfactant, when present, is chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium tricetylmonium chloride, chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamidopropyidiethylamine, arachidamidoethyidiethylamine, arachidamidoethyldimethylamine, or mixtures thereof.

In various embodiments, the total amount of cationic surfactants, when present in the compositions, may range from about 0.1% to about 10% by weight, including all subranges therebetween, such as from about 0.1% to about 10%, from about 0.1% to about 8%, from about 0.1% to about 6%, from about 0.1% to about 4%, from about 0.1% to about 3%, from about 0.1% to about 2.5%, from about 0.1% to about 2%, from about 0.1% to about 1.5%, from about 0.1% to about 1%, from about 0.5% to about 10%, from about 0.5% to about 8%, from about 0.5% to about 6%, from about 0.5% to about 4%, from about 0.5% to about 3%, from about 0.5% to about 2.5%, from about 0.5% to about 2%, from about 0.5% to about 1.5%, from about 0.5% to about 1%, from about 1% to about 10%, from about 1% to about 8%, from about 1% to about 6%, from about 1% to about 4%, from about 1% to about 3%, from about 1% to about 2.5%, or from about 1% to about 2% by weight, based on the total weight of the composition.

Solvents

Compositions according to the disclosure comprise a cosmetically acceptable solvent. The solvent may comprise water, non-aqueous solvents, or mixtures thereof.

In some embodiments, the solvent comprises, consists essentially of, or consists of water. The total amount of water in the compositions may vary depending on the type of composition and the desired consistency, viscosity, etc.

In certain embodiments, the composition comprises one or more non-aqueous solvents, other than or in addition to ingredients discussed above. For example, $C_1$-4 alcohols, organic solvents, fatty alcohols, fatty ethers, fatty esters, polyols other than those described above, glycols, vegetable oils, mineral oils, liposomes, laminar lipid materials, or any a mixture thereof. Non-limiting examples of solvents which may be used include alkane polyols such as 1,2,6-hexanetriol, trimethylolpropane, ethylene glycol, propylene glycol, diethylene glycol, hexylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol (isopropyl alcohol); glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbitol, sorbitan, acetine, diacetine, triacetine, sulfolane, or mixtures thereof. At least in some embodiments, the compositions contain water and at least one, for example two or more, additional solvent chosen from caprylyl glycol, hexylene glycol, ethylhexylglycerin, glycerin, or mixtures thereof.

The solvent may be present in the composition in an amount ranging from about 20% to about 90% by weight, relative to the total weight of the composition, including all ranges and subranges therebetween. For example, in one embodiment, the total amount of solvent may be about 20% to about 85%, about 25% to about 85%, about 30% to about 85%, about 40% to about 85%, about 45% to 85%, or about 50% to 80% by weight, relative to the total weight of the composition.

In certain embodiments, the solvent is primarily comprised of water, such as from about 20% to about 85%, about 20% to about 80%, about 20% to about 75%, about 20% to about 70%, about 20% to about 60%, about 20% to about 50%, about 20% to about 40%; from about 25% to about 90% %, about 25% to about 85%, about 25% to about 80%, about 25% to about 75%, about 25% to about 70%, about 25% to about 60%, about 25% to about 50%, about 25% to about 40%; form about 30% to about 90% %, about 30% to about 85%, about 30% to about 80%, about 30% to about 75%, about 30% to about 70%, about 30% to about 60%, about 30% to about 50%; from about 35% to about 90% %, about 35% to about 85%, about 35% to about 80%, about 35% to about 75%, about 35% to about 70%, about 35% to about 60%, about 35% to about 50%; from 40% to about 90% %, about 40% to about 85%, about 40% to about 80%, about 40% to about 75%, about 40% to about 70%, or about 40% to about 60% by weight, relative to the total weight of the composition.

Thickening Agents

The compositions described herein may, optionally, include at least one thickening agent. "Thickening agents" as used here may be referred to as "thickeners" or "viscosity modifying agents."

In some embodiments, thickening agents are water-soluble, and increase the viscosity of water or form an aqueous gel when ingredients according to the disclosure are dispersed/dissolved in water to formulate the compositions. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

As non-limiting examples, thickening agents may be chosen from xanthan gum, guar gum, biosaccharide gum, cellulose, acacia seneca gum, sclerotium gum, agarose, pechtin, gellan gum, hyaluronic acid, or mixtures thereof. Additionally, the at least one thickening agent may include polymeric thickening agents chosen from ammonium polyacryloyldimethyl taurate, ammonium acryloyldimethyltaurate/VP copolymer, sodium polyacrylate, acrylates copolymers, polyacrylamide, carbomer, acrylates/$C_{10}$-30 alkyl acrylate crosspolymer, or mixtures thereof. In some cases, the composition may optionally include ammonium polyacryloyldimethyl taurate and/or sodium polyacrylate. Suitable thickening agents may be found in U.S. patent application Ser. No. 16/731,654, which is incorporated herein, in its entirety for all purposes.

According to some embodiments, non-limiting examples of thickening agents may include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, or mixtures thereof. Particular types of thickening agents that may be mentioned include the following:

(1) Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/$C_{10}$-$C_{30}$ alkyl acrylate crosspolymers, polyacrylate crosspolymer-6, acrylamidopropyltrimonium chloride/acrylates copolymer, or mixtures thereof.

(2) Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, or mixtures thereof.

(3) Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, or mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instances, the cellulose is hydroxypropylcellulose (HPC).

(4) Polyvinylpyrrolidone (PVP) and Co-Polymers:

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

(5) Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

(6) Polyglyceryl Esters:

Non-limiting polyglycerol esters of fatty acids (polygylceryl esters) include those of the following formula:

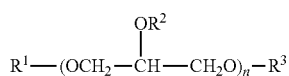

wherein n is from 2 to 20 or from 2 to 10 or from 2 to 5, or is 2, 3, 4, 5, 6, 7, 8, 9, or 10, and $R_1$, $R_2$ and $R_3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, linear or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

(7) Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

In various embodiments, the total amount of thickening agents, when present in the compositions, may range from about 0.01% to about 10% by weight, including all sub-ranges therebetween, such as from about 0.01% to about 9%, from about 0.01% to about 8%, from about 0.01% to about 6%, from about 0.01% to about 4%, from about 0.01% to about 3%, from about 0.01% to about 2.5%, from about 0.01% to about 2%, from about 0.01% to about 1.5%, from about 0.01% to about 1%, from about 0.05% to about 10%, from about 0.05% to about 8%, from about 0.05% to about 6%, from about 0.05% to about 4%, from about 0.05% to about 3%, from about 0.05% to about 2.5%, from about 0.05% to about 2%, from about 0.05% to about 1.5%, from about 0.05% to about 1%, from about 0.1% to about 10%, from about 0.1% to about 8%, from about 0.1% to about 6%, from about 0.1% to about 4%, from about 0.1% to about 3%, from about 0.1% to about 2.5%, from about 0.1% to about 2%, from about 0.1% to about 1.5%, or from about 0.1% to about 1% by weight, based on the total weight of the composition. For example, compositions according to the disclosure may comprise a total amount of thickener ranging from about 0.1% to about 0.9%, about 0.2% to about 0.8%, about 0.3% to about 0.7%, or about 0.4% to about 0.6% by weight, based on the total weight of the composition.

Additional Components

Compositions according to the disclosure may optionally comprise one or more additional components suitable for use in such compositions. Non-limiting examples of such additional components are provided below.

Monoalcohols

The compositions may further optionally include at least one monoalcohol, such as those having 1 to 10 carbons, for example, from 2 to 6 carbons.

The one or more monoalcohols of the cosmetic composition may be chosen from ethanol, propanol, butanol, pentanol, hexanol, isopropyl alcohol, cyclohexanol, isobutyl alcohol, 2-methyl-2-butanol (2-methylbutan-2-ol), and a mixture thereof. In some instances, the monoalcohols comprise or are chosen from ethanol, propanol, butanol, pentanol, an isomer thereof, or a combination thereof. In further instances, the one or more monoalcohol(s) includes or consists of ethanol.

The amount of monoalcohols present in the composition may range from about 5% to about 50%, based on the total weight of the cosmetic composition. For example, the cosmetic composition may have monoalcohol in an amount of about 5% to about 50%, about 5% to about 45%, about 5% to about 40%, about 5% to about 35%, about 5% to about 30%, about 5% to about 25%; about 10% to about 50%, about 10% to about 45%, about 10% to about 40%, about 10% to about 35%, about 10% to about 30%, about 10% to about 25%; about 15% to about 50%, about 15% to about 45%, about 15% to about 40%, about 15% to about 35%, about 15% to about 30%, or about 15% to about 25% including all ranges and sub-ranges therebetween, based on the total weight of the cosmetic composition.

pH Adjusters

The compositions may include one or more pH adjusters to increase or decrease the overall pH of the composition. For example, one or more acids may be included to decrease the pH of the cosmetic composition. Examples that may be mentioned include mineral acids, for instance hydrochloric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

The cosmetic composition may include one or more bases, such as sodium hydroxide, potassium hydroxide and the like, to increase the pH of the cosmetic composition. The basifying agent(s) may be mineral, organic or hybrid. The mineral alkaline agent(s) are optionally chosen from aqueous ammonia, alkali metal carbonates or bicarbonates such as sodium or potassium carbonates and sodium or potassium bicarbonates, sodium hydroxide or potassium hydroxide, or mixtures thereof. The organic alkaline agent(s) are optionally chosen from organic amines with a pKb at 25° C. of less than 12, for example less than 10 and even more advantageously less than 6. It should be noted that it is the pKb corresponding to the function of highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds having formula (XII) below:

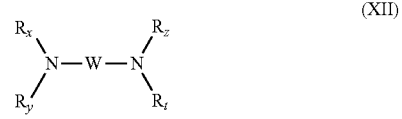

(XII)

in which W is a divalent C1 to $C_6$ alkylene radical optionally substituted with one or more hydroxyl groups or a C1 to $C_6$ alkyl radical, and/or optionally interrupted with one or more heteroatoms such as O, or Nru; Rx, Ry, Rz, Rt and Ru, which may be identical or different, represent a hydrogen atom or a C1 to C6 alkyl, C1 to C6 hydroxyalkyl or C1 to C6 aminoalkyl radical.

Additional or alternative acids and bases that are suitable for adjusting the pH of the compositions are readily known to one of ordinary skill in the art.

The amount of the pH adjuster in the compositions may be based on the desired pH of the final composition and/or product for improving curl definition, curl regularity, and/or curl elongation. For example, the total amount of the pH adjuster may range from about 0.05% to about 15%, based on the total weight of the cosmetic composition. In some instances, the total amount of pH adjuster is from about 0.05% to about 10%, about 0.1% to about 15%, about 0.1% to about 10%, or about 0.1% to about 5% by weight, including ranges and sub-ranges therebetween, based on the total weight of the cosmetic composition. For instance, in one embodiment, the pH adjuster is about 0.1M of sodium hydrate (NaOH).

In various exemplary embodiments, the conditioning agents may be chosen from cationic polymers, although in certain embodiments the compositions are free or essentially free of cationic polymers. The term "cationic polymer" means any polymer comprising at least one cationic group and/or at least one group that may be ionized into a cationic group.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), and a mixture thereof. In some cases, the hair-treatment compositions may include one or more preservatives selected from the group consisting of sodium benzoate, benzoic acid, chlorhexidine digluconate, chlorhexidine dihydrochloride, salicylic acid, phenoxyethanol, methyl paraben, and a mixture thereof.

The total amount of the one or more preservatives, when present, may vary. In some cases, the total amount of the one or more preservatives is about 0.01% to about 5%, about 0.01% to about 4%, about 0.15% to about 1%, or about 1% to about 3%, by weight, relative to the total weight of the composition.

Auxiliary Components

Compositions according to the disclosure may optionally comprise any auxiliary component suitable for use in such compositions. Such components may include, but are not limited to, dyes/pigments for adding color to the composition, moisturizing agents, fatty substances, thickeners other than those previously described, fillers, structuring agents, shine agents, antioxidants or reducing agents, penetrants, sequestrants, fragrances, buffers, dispersants, plant extracts, opacifiers, sunscreen agents, vitamins, and antistatic agents.

Optional auxiliary components may be present in an amount ranging up to about 15%, such as from about 0.001% to about 10%, from about 0.01% to about 5%, or from about 0.1% to about 3% by weight, relative to the total weight of the composition.

In various embodiments, the hair care/treatment compositions have a pH less than about 10, such as less than about 7, for example a pH ranging from about 1.5 to about 6.8, including all ranges, such as from about 2 to about 6.5, from about 2.5 to about 6, from about 3 to about 6.5, from about 3 to about 6, from about 3 to about 5.5, from about 3 to about 5, from about 3 to about 4, from about 3.5 to about 6.5, from about 3.5 to about 6, from about 3.5 to about 5.5, from about 3.5 to about 5, from about 3.5 to about 4.5, or from about 3.5 to about 4, and subranges therebetween. In one embodiment, the pH of the composition ranges from about 3 to about 6.5. In one embodiment, the pH of the composition ranges from about 3 to about 4.

Such hair care treatment compositions according to the disclosure are typically rinse-off compositions, although may be formulated as leave-in compositions. The compositions are typically in the form of a cream, paste, or lotion, but may also be in the form of a serum, a gel, a gel cream, or the like. In some embodiments, the compositions may be a hair treatment or conditioner product.

C. Temporary Hair Color Altering Compositions

Compositions for temporarily altering the color of hair according to the disclosure include a synergistic combination of citric acid and urea compounds as described above, as well as one or more agents for temporarily altering the color of hair. The temporary hair color altering compositions may also include any of the components described above in (B) for hair care/treatment compositions, as well as any other component typically used in such hair color altering compositions. The citric acid and urea compounds may be included in the temporary hair color altering compositions in amounts and ratios as described above.

In various embodiments, the temporary hair color altering composition comprises one or more hair color altering agents chosen from pigments, liposoluble dyes, or direct dyes chosen from acidic (anionic), basic (cationic), or neutral direct dyes.

Non-limiting examples of direct dyes may include azo direct dyes; (poly) methine dyes such as cyanins, hemicyanins and styryls; carbonyl dyes; azine dyes; nitro (hetero) aryl dyes; tri (hetero) arylmethane dyes; porphyrin dyes; phthalocyanin dyes, or natural direct dyes, alone or as mixtures.

Non-limiting examples of useful dyes include nitro dyes (nitro aromatic amines or aromatic amino nitroanthroquinones) which may be chosen from HC Blue No. 1, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol, 2-nitro-p-phenylenediamine, 4-nitro-o-phenylenediamine, 2-hydroxy-ethylpicramic acid, or mixtures thereof.

Non-limiting examples of hydrophobic direct dyes that can be used include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, and mixtures thereof.

Direct dyes may also be chosen from cationic direct dyes. The term "cationic direct dye" is commonly intended to mean dyes referred to as "basic direct dyes" or "basic dyes" owing to their affinity with acidic substances. The term "cationic direct dyes" is intended to mean any direct dye comprising in particular in its structure at least one endocyclic or exocyclic, cationic or cationizable group. In particular, the charge may be borne by an aryl or heteroaryl group.

Mention may be made of the hydrazono cationic dyes of formulas (Va) and (V'a), the azo cationic dyes (VIa) and (VI'a) and the diazo cationic dyes (VIIa) below:

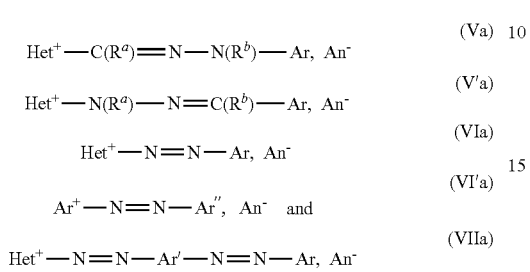

in which:
- Het⁺ represents a cationic heteroaryl radical, optionally bearing an endocyclic cationic charge, such as imidazolium, indolium or pyridinium, optionally substituted preferentially with one or more $(C_1-C_8)$alkyl groups such as methyl;
- Ar⁺ representing an aryl radical, such as phenyl or naphthyl, bearing an exocyclic cationic charge, preferentially ammonium, particularly tri $(C_1-C_8)$alkylammonium such as trimethylammonium;
- Ar represents an aryl group, especially phenyl, which is optionally substituted, preferentially with one or more electron-donating groups such as i) optionally substituted $(C_1-C_5)$alkyl, ii) optionally substituted $(C_1-C_8)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;
- Ar' is an optionally substituted divalent (hetero) arylene group such as phenylene, particularly para-phenylene, or naphthalene, which are optionally substituted, preferentially with one or more groups $(C_1-C_8)$alkyl, hydroxyl or $(C_1-C_8)$alkoxy;
- Ar'' is an optionally substituted (hetero) aryl group such as phenyl or pyrazolyl, which are optionally substituted, preferentially with one or more groups $(C_1-C_5)$alkyl, hydroxyl, (di)$(C_1-C_8)$(alkyl)amino, $(C_1-C_8)$alkoxy or phenyl;
- $R^a$ and $R^b$, which may be identical or different, represent a hydrogen atom or a group $(C_1-C_8)$alkyl, which is optionally substituted, preferentially with a hydroxyl group;
- or alternatively the substituent $R^a$ with a substituent of Het⁺ and/or $R_b$ with a substituent of Ar and/or $R^a$ with $R_b$ form, together with the atoms that bear them, a (hetero)cycloalkyl;
- particularly, $R^a$ and $R_b$ represent a hydrogen atom or a group $(C_1-C_4)$alkyl, which is optionally substituted with a hydroxyl group; and
- An⁻ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

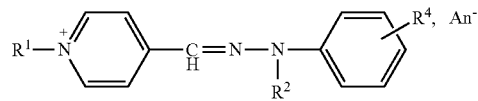

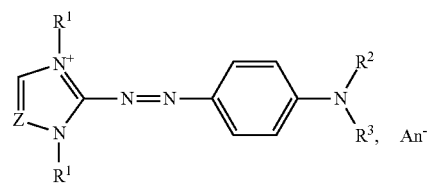

wherein in formulae (Va-1) and (VIa-1):
- $R^1$ representing a $(C_1-C_4)$alkyl group such as methyl;
- $R^2$ and $R^3$, which are identical or different, represent a hydrogen atom or a $(C_1-C_4)$alkyl group, such as methyl;
- $R^4$ represents a hydrogen atom or an electron-donating group such as optionally substituted $(C_1-C_8)$alkyl, optionally substituted $(C_1-C_5)$alkoxy, or (di)$(C_1-C_8)$(alkyl)amino optionally substituted on the alkyl group(s) with a hydroxyl group; particularly, $R_4$ is a hydrogen atom;
- Z represents a CH group or a nitrogen atom, preferentially CH; and
- An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

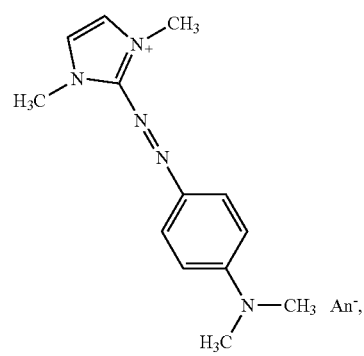

Basic Red 51

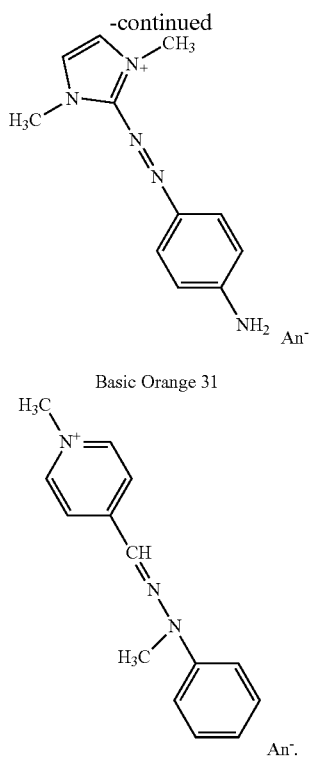

Basic Orange 31

Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic direct dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

In various embodiments, the direct dyes used to color or dye the hair according to the disclosure are chosen from non-ionic direct dyes, including hydrophobic direct dyes, ionic direct dyes, including cationic direct dyes and anionic direct dyes, or mixtures thereof.

In various embodiments, the direct dyes used to color or dye the hair according to the disclosure are chosen from non-ionic direct dyes, including hydrophobic direct dyes.

In various embodiments, the direct dyes used to color or dye the hair according to the disclosure are chosen from ionic direct dyes, including cationic direct dyes and anionic direct dyes, or mixtures thereof. In further embodiments, the direct dyes used to color or dye the hair according to the disclosure are hydrophilic direct dyes.

In various embodiments, the direct dyes used to color or dye the hair according to the disclosure are selected from hydrophobic direct dyes. In other embodiments, the direct dye used to color or dye the hair according to the disclosure is selected from cationic direct dyes. In yet further embodiments, the direct dye used to color or dye the hair according to the disclosure comprises a mixture of hydrophobic direct dyes and cationic direct dyes.

In various embodiments, the direct dye used to color or dye the hair according to the disclosure is selected from the group consisting of HC blue 15, hydroxyanthraquinoneaminopropyl methyl morpholinium methosulfate, Basic violet 2, Disperse violet 1, Disperse red 15, Basic Red 51, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylaminophenol, Acid red 33, HC violet no. 1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no. 7, Acid red 92, Acid violet 43, Ext violet 2, Acid green 25, Acid black 1, and combinations thereof.

In some exemplary embodiment, at least direct dye is chosen from triarylmethane dyes of formula (IV):

or the organic or mineral, acid or base addition salts thereof, the geometrical isomers, optical isomers, or tautomers thereof, the mesomeric forms thereof, or the solvates or hydrates thereof, wherein:

A, B, and C are identical or different, and each represents a (hetero) aryl group which is optionally substituted, and

- - - - represents a single bond or a double bond.

The direct dyes of formula (IV) can be cationic, anionic, non-ionic or zwitterionic. According to one particularly preferred embodiment of the invention, the triarylmethane dye(s) are cationic.

In some embodiments, the dyes of triarylmethane structure are chosen from Basic Violet 2, Basic Blue 1 and/or Basic Blue 77 (also known as HC Blue 15), and mixtures thereof, better from Basic Violet 2 and/or Basic Blue 77 (also known as HC Blue 15), and mixtures thereof.

In various exemplary embodiments, the total amount of dyes in the compositions for temporarily altering the color of hair may range from about 0.0001% to about 10% by weight, including all subranges therebetween, such as from about 0.0001% to about 8%, from about 0.0001% to about 6%, from about 0.0001% to about 4%, from about 0.0001% to about 2%, from about 0.0001% to about 1%, from about 0.0001% to about 0.8%, from about 0.0001% to about 0.5%, from about 0.0005% to about 8%, from about 0.0005% to about 6%, from about 0.0005% to about 4%, from about 0.0005% to about 2%, from about 0.0005% to about 1%, from about 0.001% to about 8%, from about 0.001% to about 6%, from about 0.001% to about 4%, from about 0.001% to about 2%, from about 0.001% to about 1%, from about 0.001% to about 0.8%, from about 0.001% to about 0.5%, from about 0.005% to about 6%, from about 0.005% to about 4%, from about 0.005% to about 2%, from about 0.005% to about 1%, from about 0.005% to about 0.8%, from about 0.005% to about 0.5% by weight, relative to the total weight of the composition.

In various embodiments, the total amount of dyes in the composition for temporarily altering the color of the hair ranges from about 0.0005% to about 5%, for example from about 0.001% to about 5% by weight, relative to the total weight of the composition.

The temporary hair color altering compositions according to the disclosure may optionally comprise at least one pigment. These pigments may be in the form of powder or pigmentary paste, and may be coated or uncoated. The pigments may be chosen, for example, from mineral pigments, organic pigments, lakes, pigments with special effects such as nacres or glitter flakes, or mixtures thereof.

Exemplary and non-limiting mineral pigments include iron oxides, chromium oxides, manganese violet, ultramarine blue, chromium hydrate, ferric blue and titanium oxide.

Exemplary and non-limiting organic pigments include nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds. For example, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470.

Composite pigments, which are pigment particles comprising a mineral core, at least one binder, and at least one organic pigment at least partially covering the core, may also be used.

Exemplary and non-limiting lakes include those which have dyes chosen from cochineal carmine, D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), and/or D&C Blue 1 (CI 42 090) adsorbed onto insoluble particles, e.g. inorganic substrates such as alumina, silica, calcium sodium borosilicate, calcium aluminium borosilicate, or aluminium. An example of a lake that may be used is D&C Red 7 (CI 15 850:1).

Useful pigments with special effects include any pigment that generally creates a non-uniform colored appearance (characterized by a certain shade, a certain vivacity, and/or a certain lightness) that changes as a function of the conditions of observation (e.g. light, temperature, observation angles, etc.). This may include, for example, pigments with a low refractive index, such as fluorescent, photochromic, or thermochromic pigments, and those with a higher refractive index, such as nacres or glitter flakes.

The size of the pigments is not limited, but may generally range from about 10 nm to about 200 nm, for example from about 20 nm to about 80 µm, or from about 30 nm to about 50 µm.

If present, the total amount of pigments may range from about 0.05% to about 20%, for example from about 0.1% to about 15% by weight, relative to the total weight of the composition.

D. Permanent Hair Color Altering Compositions

The disclosure also relates to compositions for permanently altering the color of hair which are prepared at or near or at the time of use by mixing a permanent hair (color) base or bleach composition with a developer composition, wherein the mixture further includes a synergistic combination of citric acid and urea compounds as described above.

Hair (Color) Base Compositions

Typical hair color base compositions (also referred to as hair color bases) can be used in compositions and methods for coloring the hair according to the disclosure. The hair color base compositions may, for example, comprise (a) at least one hair color agent, (b) an alkaline component, and (c) a solvent system.

Other hair base compositions that can be used include clear hair base compositions. These compositions may be referred to as hair toner compositions, and should be understood for purposes of the disclosure as being included with the description of hair color base compositions, with the understanding that the hair base compositions may be free or substantially free of hair color agents but otherwise typically comprise the same or similar components as those described for hair color base compositions.

Hair Color Agent

The hair color base compositions typically include one or more oxidation dyes for permanently altering the color of hair. The oxidation dyes are generally chosen from one or more oxidation bases or precursors, optionally combined with one or more couplers. By way of example, the oxidation bases are chosen from para-phenylenediamines, bis (phenyl)alkylenediamines, para-aminophenols, ortho-aminophenols, meta-aminophenols, and heterocyclic bases, and the addition salts thereof.

Among the para-phenylenediamines that may be mentioned, for example, are para-phenylenediamine, para-toluenediamine (toluene-2,5-diamine), 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, hydroxypropyl bis(n-hydroxyethyl-p-phenylenediamine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be chosen.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl) phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the meta-aminophenols, 3-aminophenol and salts thereof, may be mentioned.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in compositions according to the disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl) methanol, 2-(3-aminopyrazolo[1,5-a]pyrid-5-yl) ethanol, 2-(3-aminopyrazolo[1,5-a]pyrid-7-yl) ethanol, (3-aminopyrazolo[1,5-a]pyrid-2-yl) methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-α-hydroxyethoxy-3-amino-pyrazolo[1,5-a]pyridine; 2-(4-dimethylpyperazinium-1-yl)-3-amino-pyrazolo[1,5-a]pyridine; hydroxyethoxy aminopryazolopyridine, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl) pyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl) pyrazole may also be used. According to some embodiments, 2,3-diaminodihydropyrazolo pyrazolone dimethosulfonate may also be used. Optionally, a 4,5-diaminopyrazole may be used, for example 4,5-diamino-1-(β-hydroxyethyl) pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H, 5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one. For example, 2,3-diamino-6,7-dihydro-1H,5H-pyrazolo[1,2-a]pyrazol-1-one and/or a salt thereof may be used.

According to some embodiments, 2,3-diaminodihydropyrazolo pyrazolone dimethosulfonate may be used. 4,5-diamino-1-(β-hydroxyethyl) pyrazole and/or 2,3-diamino-6,7- dihydro-1H,5H-pyrazolo[1,2-a]pyrazol-1-one and/or a salt thereof may be used as heterocyclic bases.

Hair color base compositions according to the disclosure may optionally comprise one or more couplers advantageously chosen from those conventionally used in the dyeing or coloring of hair. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N—(ß-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(ß-hydroxyethyloxy) benzene (2,4 diaminophenoxyethanol HCL), 2-amino-4-(ß-hydroxyethylamino)-1-methoxy-benzene (2-methyl-5-hydroxyethylaminophenol), 1,3-diaminobenzene, 1,3-bis(2, 4-diaminophenoxy) propane, 3-ureidoaniline, 3-ureido-1-dimethylaminobenzene, sesamol, 1-ß-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N—(ß-hydroxyethyl)amino-3,4-methylenedioxybenzene, 2,6-bis(ß-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 4-amino-2-hydroxytoluene, 2-methylresorcinol, 4-chlororesorcinol, and 6-methylpyrazolo[1,5-a]benzimidazole, the addition salts thereof with an acid, or mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may, for example, represent from about 0.0001% to about 15% by weight relative to the total weight of the composition, such as from about 0.0001% to about 12%, about 0.0001% to about 10%, about 0.0001% to about 8%, about 0.0001% to about 5%, about 0.001% to about 12%, about 0.001% to about 10%, about 0.001% to about 8%, about 0.001% to about 5%, about 0.005% to about 10%, about 0.005% to about 8%, about 0.005% to about 6%, or about 0.005% to 5% by weight, relative to the total weight of the hair color base composition.

The coupler(s), if they are present, may individually from about 0.0001% to about 15% by weight relative to the total weight of the composition, such as from about 0.0001% to about 12%, about 0.0001% to about 10%, about 0.0001% to about 8%, about 0.0001% to about 5%, about 0.001% to about 12%, about 0.001% to about 10%, about 0.001% to about 8%, about 0.001% to about 5%, about 0.005% to about 10%, about 0.005% to about 8%, about 0.005% to about 6%, or about 0.005% to 5% by weight, relative to the total weight of the hair color base composition.

Alkaline Component

Hair (color) base compositions typically include an alkaline component. According to various embodiments, the alkaline component may comprise at least one organic alkalizing agent and/or at least one mineral alkalizing agent.

In certain embodiments, the alkaline component comprises at least one organic alkalizing agent chosen from monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1, 2-propanediol, 3-dimethylamino-1,2-propanediol, tris (hydroxymethyl)amino-methane, or mixtures thereof.

In further embodiments, the alkaline component comprises at least one mineral alkalizing agent chosen from ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures thereof. In some embodiments, the alkaline component comprises ammonia and/or ammonium hydroxide.

In some embodiments, the alkaline component comprises at least one organic alkalizing agent and is free or substantially free of mineral alkalizing agents. For example, the alkaline component may comprise less than about 0.5%, less than about 0.4%, less than about 0.3%, less than about 0.2%, less than about 0.1%, or less than about 0.05% of mineral alkalizing agents. In certain embodiments, the alkaline component comprises at least one organic alkalizing agent and is free or substantially free of ammonia and/or ammonium-based compounds. In various embodiments, the alkaline component comprises monoethanolamine. In further embodiments, the alkaline component comprises monoethanolamine and is free or substantially free of ammonia and/or ammonium-based compounds.

In certain embodiments, the alkaline component comprises at least one organic alkalizing agent and is present in an amount of at least about 5% by weight, relative to the total weight of the hair color base. For example, the at least one organic alkalizing agent may be present in an amount ranging from about 5% to about 20%, for example from about 6% to about 18%, from about 7% to about 15%, or from about 8% to about 12% by weight, relative to the total weight of the hair color base. In further embodiments, the at least one organic alkalizing agent may be present in an amount ranging from about 5% to about 18%, from about 5% to about 15%, from about 5% to about 12%, from about 6% to about 20%, from about 6% to about 15%, from about 6% to about 12%, from about 7% to about 20%, from about 7% to about 18%, from about 7% to about 12%, from about 8% to about 20%, from about 8% to about 18%, or from about 8% to about 15% by weight, relative to the total weight of the hair color base.

In some embodiments, the alkaline component may comprise at least one organic alkalizing agent and be free or substantially free of mineral alkalizing agents, wherein the organic alkalizing agent is present in an amount of at least about 5% by weight, relative to the total weight of the hair color base. For example, the alkaline component may comprise at least one organic alkalizing agent and be free or substantially free of mineral alkalizing agents, wherein the organic alkalizing agent is present in an amount ranging from about 5% to about 20%, for example from about 6% to about 18%, from about 7% to about 15%, or from about 8% to about 12% by weight, relative to the total weight of the hair color base, such as from about 5% to about 18%, from about 5% to about 15%, from about 5% to about 12%, from about 6% to about 20%, from about 6% to about 15%, from about 6% to about 12%, from about 7% to about 20%, from about 7% to about 18%, from about 7% to about 12%, from about 8% to about 20%, from about 8% to about 18%, or from about 8% to about 15%.

In further embodiments, the alkaline component comprises at least one mineral alkalizing agent and is optionally free or substantially free of organic alkalizing agents. For example, in various embodiments the at least one mineral alkalizing agent may be present in an amount of at least 0.5% by weight, relative to the total weight of the hair color base, such as, for example, an amount ranging from about 1% to about 15%, for example from about 1.5% to about 12%, from about 2% to about 10% or from about 2.5% to about 8%, or from about 3% to about 6% by weight, relative to the total weight of the hair color base. In some embodiments, the alkaline component may comprise at least one mineral alkalizing agent, present in an amount ranging from about 0.01% to about 12%, for example from about 0.1% to about 11%, from about 0.5% to about 10%, or from about 1% to about 8% by weight, relative to the total weight of the hair color base. In some embodiments, the at least one mineral alkalizing agent is present in an amount ranging from about 0.1% to about 15%, from about 0.1% to about 13%, from about 0.1% to about 11%, from about 0.1% to about 10%, from about 0.1% to about 9%, from about 0.1% to about 8%, from about 0.1% to about 7%, from about 0.1% to about 6%, from about 0.1% to about 5%, from about 0.25% to about 15%, from about 0.25% to about 13%, from about 0.25% to about 11%, from about 0.25% to about 10%, from about 0.25% to about 9%, from about 0.25% to about 8%, from about 0.25% to about 7%, from about 0.25% to about 6%, from about 0.25% to about 5%, from about 0.5% to about 15%, from about 0.5% to about 13%, from about 0.5% to about 11%, from about 0.5% to about 10%, from about 0.5% to about 9%, from about 0.5% to about 8%, from about 0.5% to about 7%, from about 0.5% to about 6%, from about 0.5% to about 5%, from about 1% to about 15%, from about 1% to about 13%, from about 1% to about 11%, from about 1% to about 10%, from about 1% to about 9%, from about 1% to about 8%, from about 1% to about 7%, from about 1% to about 6%, or from about 1% to about 5% by weight, relative to the total weight of the hair color base.

In other embodiments, the alkaline component may comprise at least one organic alkalizing agent and at least one mineral alkalizing agent. For example, in various embodiments the at least one organic alkalizing agent may be present in an amount of at least 0.5% by weight, relative to the total weight of the hair color base, such as, for example, an amount ranging from about 1% to about 20%, for example from about 1.5% to about 18%, from about 2% to about 16% or from about 2.5% to about 14%, or from about 3% to about 12% by weight, relative to the total weight of the hair color base, and the at least one mineral alkalizing agent may be present in an amount of at least 0.001% by weight, relative to the total weight of the hair color base, such as, for example, an amount ranging from about 0.01% to about 10%, for example from about 0.05% to about 8%, from about 0.1% to about 7% or from about 0.2% to about 6%, or from about 0.3% to about 5% by weight, relative to the total weight of the hair color base. As further examples, in some embodiments, the alkaline component may comprise at least one organic alkalizing agent and at least one mineral alkalizing agent, wherein the at least one organic alkalizing agent is present in an amount of at least 0.5%, such as from about 0.5% to about 10%, for example from about 1% to about 8%, from about 2% to about 7%, or from about 3% to about 6% by weight, and the at least one mineral alkalizing agent is present in an amount ranging from about 0.001% to about 15%, such as from about 0.01% to about 10%, for example from about 0.1% to about 8%, from about 0.5% to about 5%, or from about 1% to about 3% by weight, relative to the total weight of the hair color base. In certain embodiments, the alkaline component comprises monoethanolamine in combination with ammonia and/or ammonium hydroxide.

In some non-limiting embodiments where the alkaline component comprises at least one organic alkalizing agent and at least one mineral alkalizing agent, the total amount of the alkaline component may range from about 1% to about 20%, for example from about 1.5% to about 18%, from about 2% to about 16%, from about 2.5% to about 15%, or from about 3% to about 14%, or from about 4% to about 13% by weight, relative to the total weight of the hair color base, for example from about 1% to about 18%, from about 1% to about 16%, from about 1% to about 15%, from about 1% to about 14%, from about 1% to about 13%, from about 1% to about 12%, from about 1.5% to about 20%, from about 1.5% to about 16%, from about 1.5% to about 15%, from about 1.5% to about 14%, from about 1.5% to about 13%, from about 1.5% to about 12%, from about 2% to about 20%, from about 2% to about 18%, from about 2% to about 15%, from about 2% to about 14%, from about 2% to about 13%, from about 2% to about 12%, from about 2.5% to about 20%, from about 2.5% to about 18%, from about 2.5% to about 16%, from about 2.5% to about 14%, from about 2.5% to about 13%, from about 2.5% to about 12%, from about 3% to about 20%, from about 3% to about 18%, from about 3% to about 16%, from about 3% to about 15%, from about 3% to about 13%, from about 3% to about 12%, from about 4% to about 20%, from about 4% to about 18%, from about 4% to about 16%, from about 4% to about 15%, from about 4% to about 14%, or from about 4% to about 12% by weight, relative to the total weight of the hair color base.

Solvent

The hair (color) base compositions according to the disclosure generally comprise a solvent comprising water, optionally at least one organic solvent, or mixtures thereof.

The hair (color) base according to the disclosure optionally comprises water in at least certain embodiments. In various embodiments, the hair color base comprises water in an amount ranging up to about 60%, such as up to about 55%, up to about 50%, up to about 45%, up to about 40%, up to about 35%, up to about 30%, or up to about 25% by weight, relative to the total weight of the hair color base. In various embodiments, the hair color base comprises water in an amount greater than about 20%, such as, for example, greater than about 25%, or greater than about 30%. For example, the hair color base may comprise water in an amount ranging from about 20% to about 60%, from about 20% to about 55%, from about 25% to about 50%, from about 25% to about 45%, from about 25% to about 40%, from about 30% to about 45%, or from about 30% to about 40% by weight, relative to the total weight of the hair color base.

In various embodiments, the hair (color) base comprises at least one organic solvent. Examples of organic solvents that may be mentioned include linear or branched C2-C4 alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof. If present, the hair color base may comprise a total amount of organic solvents ranging from about 1% to about 40%, such as about 5% to about 30% by weight.

In certain embodiments, the hair (color) base comprises a mixture of water and at least one organic solvent.

Additional Components

The hair (color) base compositions may further optionally comprise any additional components typically used in such compositions, such as, for example, chelating agents, oils, thickening agents, direct dyes or pigments, and/or auxiliary components.

Hair (color) base compositions according to the disclosure optionally comprise at least one chelating agent. In some embodiments, the chelating agent may be chosen from organic acids and salts, thereof including carboxylic acids such as gluconic, citric, and tartaric acids. The salts of the organic acids of the present invention may contain an organic or inorganic cation. In some embodiments, the chelating agent is chosen from mono-, di-, or poly-, amino-, or hydroxy-carboxylic acids, mono-, di-, or poly-, amino-, or hydroxy-sulfonic acids, mono-, di-, or poly-, amino-, or hydroxy-phosphonic acids, or mixtures thereof.

In certain embodiments, useful chelating agents include those based on aminocarboxylic acids, iminodisuccinic acid, ethanoldiglycine acid, phosphonobutane tricarboxylic acid, tetrasodium glutamate diacetate, monophosphonic acid, polyphosphonic acid, polyphosphoric acid, or mixtures thereof. Non-limiting examples of useful chelating agents that may be chosen include ethylenediaminetetraacetic acid (EDTA), tripotassium phosphate, trisodium phosphate, disodium silicate, dipotassium silicate, sodium phytate, tetrasodium etidronate, tetrasodium pyrophosphate, pentasodium ethylenediamine tetramethylene phosphonate, sodium staminate, tetrasodium glutamate diacetate, or mixtures of two or more of any of the foregoing. In some embodiments, the chelating agent comprises EDTA, tetrasodium glutamate diacetate, or mixtures thereof. In preferred embodiments, the chelating agent comprises tetrasodium glutamate diacetate. In some embodiments, the chelating agent comprises tetrasodium glutamate diacetate and the hair color base is free or substantially free of other chelating agents.

According to various embodiments, the at least one chelating agent may be present in an amount ranging up to about 3%, such as from about 0.001% to about 2.5%, for example from about 0.05% to about 2%, from about 0.05% to about 1.5% or from about 0.1% to about 1%, or from about 0.1% to about 0.5% by weight, relative to the total weight of the hair color base. For example, the at least one chelating agent may be present in an amount ranging from about 0.01% to about 3%, from about 0.01% to about 2%, from about 0.01% to about 1.5%, from about 0.01% to about 1%, from about 0.01% to about 0.5%, from about 0.05% to about 3%, from about 0.05% to about 2.5%, from about 0.05% to about 1.5%, from about 0.05% to about 1%, from about 0.05% to about 0.5%, from about 0.1% to about 3%, from about 0.1% to about 2.5%, from about 0.1% to about 2%, or from about 0.1% to about 1.5% by weight, relative to the total weight of the hair color base.

Hair (color) base compositions according to the disclosure optionally comprise at least one oil, in particular chosen from natural oils. In various embodiments, the at least one oil is present in the hair color base in an amount of at least about 0.1% by weight, relative to the total weight of the hair color base. For example, in some embodiments the at least one oil may be present in an amount ranging from about 0.1% to about 8%, for example from about 0.1% to about 6%, from about 0.2% to about 5%, or from about 0.2% to about 2% by weight, relative to the total weight of the hair color base, such as, for example, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 0.2% to about 8%, from about 0.2% to about 7%, from about 0.2% to about 6%, from about 0.2% to about 4%, from about 0.2% to about 3%, from about 0.2% to about 1%, from about 0.3% to about 8%, from about 0.3% to about 7%, from about 0.3% to about 6%, from about 0.3% to about 5%, from about 0.3% to about 4%, from about 0.3% to about 3%, from about 0.3% to about 2%, from about 0.3% to about 1%, from about 0.4% to about 8%, from about 0.4% to about 7%, from about 0.4% to about 6%, from about 0.4% to about 5%, from about 0.4% to about 4%, from about 0.4% to about 3%, from about 0.4% to about 2%, or from about 0.4% to about 1% by weight, relative to the total weight of the hair color base.

By "natural oil," it is meant that the oil is derived from a plant, animal, or mineral. Non-limiting examples of oils derived from plants that can be used include olive oil, sweet almond oil, coconut oil, avocado oil, wheat germ oil, sunflower oil, grape seed oil, sesame oil, corn oil, apricot oil, castor oil, shea oil, soybean oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, camelina sativa seed oil, tamanu oil, babassu oil, pracaxi oil, and musk rose oil. A non-limiting example of oils of animal origin includes perhydrosqualene. As non-limiting examples of mineral oils, liquid paraffin and liquid petroleum jelly may be chosen.

Mixtures of two or more natural oils may also be chosen, such as, for example, mixtures of two or more oils of plant origin, two or more oils of animal origin, two or more oils of mineral origin, one or more oils of plant origin in combination with one or more oils of animal origin, one or more oils of plant origin in combination with one or more oils of mineral origin, one or more oils of animal origin in combination with one or more oils of mineral origin, two or more oils of plant origin in combination with one or more oils of animal origin, two or more oils of plant origin in combination with one or more oils of mineral origin, two or more oils of animal origin in combination with one or more oils of mineral origin, etc.

In some embodiments, the at least one natural oil comprises at least one plant oil, and the hair color base is free or substantially free of animal and/or mineral oils. In some embodiments, the hair color bases may comprise less than about 25%, such as less than about 20%, less than about 15%, or less than about 10% of animal and/or mineral oils, such as about 9% or less, about 8% or less, about 7% or less, about 6% or less, about 5% or less, about 4% or less, about 3% or less, about 2% or less, or about 1% or less. In preferred embodiments, the hair color bases comprise from about 0.001% to about 10% of animal and/or mineral oils, such as from about 0.01% to about 8%, or from about 0.1% to about 6% by weight, relative to the total weight of the composition. In another preferred embodiment, the hair color base comprises no animal and/or mineral oils.

Hair (color) base compositions according to the disclosure optionally comprise at least one thickening agent. For instance, useful and non-limiting thickening agents include polymeric thickeners and non-polymeric thickeners. The at least one polymeric thickener can be chosen from ionic or non-ionic, associative or non-associative polymers. Exemplary thickeners include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, biosacharide gum, pullulan, hydroxypropylmethyl cellulose, hydroxyethyl cellulose, hydroxypropyl cellulose, polyvinyl pyrrolidone, carboxymethyl cellulose, polyacrylic acid, methylmethacrylate copolymer, carboxyvinyl polymer, dextrin, polyvinyl alcohol, carboxylated polyvinylalcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, poloxamer polymers, or mixtures thereof.

In various embodiments, the at least one thickening agent may be chosen from cellulose derivatives, acrylic acid and/or acrylate based polymers, poloxamer polymers, acacia, tragacanth, alginates, carrageenan, xanthan gum, petroleum jelly, waxes, starches, starch derivatives, clays colloidal silicon dioxide, microcrystalline cellulose, or mixtures thereof. In at least certain embodiments, the at least one thickening agent is chosen from polymeric thickening agents. By way of example, the at least one thickening agent may be chosen from poloxamer polymers. In preferred embodiments, the hair color base compositions comprise at least one thickening agent chosen from poloxamer polymers.

Hair (color) base compositions according to the invention may optionally comprise one or more pigments and/or direct dyes, as described above in (C), in addition to the oxidation dye(s).

When present, the pigment and/or direct dye(s) may, for example, be present in an amount ranging from 0.001% to 10% by weight, such as from 0.005% to 5% by weight, relative to the total weight of the composition.

The hair color base may comprise one or more auxiliary components, such as, for example, pH adjusters; vitamins; amino acids, for example wheat amino acids; anionic, cationic, nonionic, amphoteric or zwitterionic polymers or mixtures thereof; antioxidants, for example erythorbic acid, sodium metabisulfite, and/or ammonium thiolactate; penetrants; fragrances; dispersants; film-forming agents; ceramides; preserving agents, for example phenoxyethanol; opacifiers; emulsifiers; conditioning agents; and/or auxiliary components. In at least certain embodiments, the composition is free or substantially free of ammonium thiolactate.

The additional components, individually or in total, may be present in an amount ranging from about 0.0001% to about 20%, such as from about 0.0001% to about 15%, from about 0.0001% to about 10%, from about 0.0001% to about 5%, from about 0.0001% to about 3%, from about 0.0001% to about 2%, or from about 0.0001% to about 1% by weight, relative to the total weight of the hair (color) base composition.

The pH of the hair (color) base composition may, in at least certain embodiments, be the same or substantially the same as the pH of the hair color base, for example prior to mixing the hair color base and oxidizing component. In some embodiments, the pH of the hair color altering composition may range from about 8 to about 12, such as, for example, from about 8 to about 11, from about 8.5 to about 10, or about 9.0 to about 9.5.

Bleaching Compositions

Hair bleaching compositions typically include at least one oxidizing agent, which may be chosen from peroxides, persulfates, perborates, percarbonates, peracids, bromates, their salts or mixtures thereof. In various embodiments, the at least one oxidizing agent is chosen from alkali metal salts of perborates, percarbonates, bromates, and persulfates, such as, for example, ammonium, sodium, potassium salts, or mixtures thereof. By way of example, non-limiting persulfates include potassium persulfate, sodium persulfate, and ammonium persulfate.

By way of example only, the amount of oxidizing agent(s) in the bleach composition may range from about 10% by weight to about 100% by weight, such as from about 20% to about 90% by weight, from about 30% to about 80% by weight, or from about 40% to about 75% by weight, based on the total weight of the bleach composition. In further embodiments, the amount of oxidizing agent(s) in the bleach composition may range from about 5% to about 50%, such as about 10% to about 45%, or about 15% to about 40%. In some embodiments, the amount of oxidizing agent(s) in the bleach composition is at least about 30%, such as at least about 40% by weight, based on the total weight of the bleach composition.

The bleaching compositions may also optionally include at least one silicate compound. Non-limiting examples of silicates include lithium, sodium, and potassium silicates, metasilicates and disilicates, and combinations thereof, including mixed lithium, sodium, and potassium salts thereof. Specific non-limiting examples include aluminum silicate, magnesium silicate, aluminum magnesium silicate, calcium silicate, barium silicate, strontium silicate, potassium silicate, potassium metasilicate, sodium silicate, sodium metasilicate, or any mixture thereof. In one embodiment, the at least one silicate compound is chosen from sodium silicate, sodium metasilicate, or mixtures thereof.

The total amount of silicates in the hair bleaching composition may vary, but is typically about 1% to about 40% by weight, based on the total weight of the hair bleaching composition. In some embodiments, the total amount of the one or more silicates is about 1% to about 35%, about 1% to about 30%, about 1% to about 25%, about 1% to about 20%, about 5% to about 40%, about 5% to about 35%, about 5% to about 30%, about 5% to about 25%, about 5% to about 20%, about 10% to about 40%, about 10% to about 35%, about 10% to about 30%, about 10% to about 25%, about 10% to about 20%, about 15% to about 40%, about 15% to about 35%, about 15% to about 30%, about 15% to about 25%, or about 15% to about 20% by weight, based on the total weight of the hair bleaching composition. In some embodiments, the total amount of silicates ranges from about 12% to about 20% or about 14% to about 18% by weight, based on the total weight of the hair bleaching composition.

In preferred embodiments, the compositions comprise ammonium, sodium, and/or potassium persulfate and at least one silicate, for example sodium silicate and/or sodium metasilicate.

Optionally, the hair bleaching compositions may include one or more alkaline agents other than the at least one silicate compound. By way of example, alkanolamines, organic amines, basic amino acids, salts thereof, or mixtures thereof may be chosen. Non-limiting examples of alkanolamines include monoethanolamine and triethanolamine. Non-limiting examples of organic amines include 2-amino-2-methyl-1-propanol (AMP), 2-amino-2-methyl-1,3-propanediol, and guanidine. Non-limiting examples of basic amino acids include arginine, glycine, and lysine. In other embodiments, additional alkaline agents may be chosen from inorganic alkaline agents such as sodium hydroxide, potassium hydroxide, calcium hydroxide, magnesium hydroxide, magnesium carbonate hydroxide, barium hydroxide, sodium phosphate, potassium phosphate, ammonium carbonate, potassium carbonate, or magnesium carbonate. Mixtures of any of the above additional alkaline agents may be used, for example glycine and magnesium carbonate hydroxide.

The total amount of the one or more additional alkaline agents other than the silicate compounds may vary, but may range from about 0.1% to about 20% by weight, based on the total weight of the hair bleaching composition. In some embodiments, the total amount of the one or more alkaline agents other than the silicate compounds ranges from about 0.1% to about 15%, about 0.1% to about 13%, about 0.1% to about 11%, about 1% to about 15%, about 1% to about 13%, about 1% to about 11%, about 3% to about 15%, about 3% to about 13%, about 3% to about 11%, about 5% to about 15%, about 5% to about 13%, or about 5% to about 11% by weight, based on the total weight of the hair bleaching composition.

The hair bleaching composition may optionally include one or more thickening agents. Non-limiting examples of thickening agents include carboxylic acid/carboxylate copolymers, hydrophobically-modified cross-linked copolymers of carboxylic acid and alkyl carboxylate vinyl polymers, methyl cellulose, ethyl cellulose, hydroxyethyl cellulose, hydroxylpropyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, polyethyleneimine, bentonite, aluminum magnesium silicate, laponite, hectonite, anhydrous silicic acid, or mixtures thereof. In some embodiments, guar gum is particularly useful.

The total amount of thickening agents may vary, but typically ranges from about 0.1% to about 10% by weight, based on the total weight of the hair bleaching composition. In some embodiments, the total amount of thickening agents may range from about 0.1% to about 8%, such as about 0.1% to about 6%, about 0.1% to about 4%, about 0.5% to about 10%, about 0.5% to about 8%, about 0.5% to about 6%, about 0.5% to about 12%, about 0.5% to about 10%, about 0.5% to about 8%, about 0.5% to about 6%, about 0.5% to about 4%, about 1% to about 10%, about 1% to about 8%, about 1% to about 6%, about 1% to about 4%, or about 1% to about 3% by weight, based on the total weight of the hair bleaching composition.

In some embodiments, the hair bleaching composition includes one or more oils. The oils may include those generally used in cosmetics and particularly oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organofluorinated oils, volatile or non-volatile silicone oils, fluorosilicone oils and their mixtures. Mention is made, as an example of linear or branched hydrocarbons, of oils of mineral or synthetic origin, such as liquid paraffins and their derivatives, petrolatum, mineral oils, polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

If present, the total amount of the one or more oils in the hair bleaching composition may vary but is typically less than about 5%, such as about 0.1% to about 5% by weight, based on the total weight of the hair bleaching composition. In some embodiments, the total amount of the one or more oils may be about 0.1% to about 4%, about 0.1% to about 3%, about 0.1% to about 2%, or about 0.1% to about 1% by weight, based on the total weight of the hair bleaching composition.

Auxiliary components may also optionally be included in the hair bleaching compositions such as, for example, preservatives, cationic conditioning compounds including cationic conditioning polymers, rheology-modifying agents, chelating agents, fatty substances, fragrances, colorants (e.g. direct dyes and/or pigments), fillers, amino acids (e.g. glycine or taurine), surfactants (cationic, anionic, nonionic, and/or amphoteric), dessicants, de-dusting agents, ceramides, pH adjusting agents, etc. Such auxiliary components may be present in an amount ranging from about 0.001% to about 5%, such as about 0.01% to about 3%, or about 0.1% to about 2%.

The bleach composition may be in any form, such as, for example, in the form of a powder, gel, liquid, foam, lotion, cream, mousse, and emulsion. In various exemplary embodiments, the bleach composition is anhydrous. Optionally, water may be added as an activator, by mixing it with the bleach composition.

Optionally, the bleach compositions may also contain acid and alkali pH adjusters. Such pH adjusters include, but are not limited to, sodium metasilicate, silicate compounds, citric acid, ascorbic acid, and carbonate compounds. In various embodiments, the bleach composition is alkaline, with the pH ranging from about 7, 8, 9, or 10 to about 8, 9, 10 or 11. According to preferred embodiments, the bleach composition has a pH higher than about 7, such as higher than about 8, or higher than about 9.

Developer Compositions

Typical developer compositions (also referred to as oxidizing compositions) can be used in compositions and methods for altering the color of the hair according to the disclosure. The developer compositions comprise at least one oxidizing agent, and typically a cosmetically suitable carrier.

As useful oxidizing agents, hydrogen peroxide, urea peroxide, alkali metal bromates, alkali metal ferricyanides, and persalts, such as perborates or persulphates, may be chosen. Use may also be made of one or more oxidation-reduction enzymes, such as laccases, peroxidases and 2-electron oxidoreductases (such as uricase), optionally in the presence of their respective donor or cofactor.

In certain preferred embodiments, the oxidizing agent is hydrogen peroxide. In various embodiments the hydrogen peroxide may be present in an aqueous solution whose titer may range from 1 to 40 volumes, such as from 5 to 40 volumes, from 5 to 30 volumes, or from 5 to 20 volumes. In certain embodiments, the oxidizing component is a 10V, 20V, 30V, or 40V hydrogen peroxide developer composition.

The oxidizing agent may, in various embodiments, be present in the developer composition in an amount ranging from about 0.05% to about 50% by weight, such as from about 0.1% to about 30% by weight, from about 0.1% to about 20% by weight, about 1% to about 20%, about 1% to about 15%, about 1% to about 12%, about 3% to about 20%, about 3% to about 15%, about 3% to about 12%, about 5% to about 20%, about 5% to about 15%, about 5% to about 12%, about 7% to about 20%, about 7% to about 15%, about 7% to about 12%, about 9% to about 20%, about 9% to about 15%, or about 9% to about 12% by weight, based on the total weight of the developer composition.

The developer composition may contain at least one solvent, for example water, organic solvents, or mixtures thereof. Suitable organic solvents for use in the developer composition, alone or in mixture with water, include but are not limited to ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, or mixtures thereof.

The organic solvents for use in the developer compositions can be volatile or non-volatile compounds. The organic solvent may, for example, be present in an amount ranging from about 0.5% to about 70% by weight, such as from about 2% to about 60% by weight, such as from about 5 to about 50% by weight, relative to the total weight of the developer composition.

The developer compositions may optionally include other components typically used in developer compositions, such as, for example, rheology-modifying agents, chelants, fatty substances, ceramides, pH adjusting agents, preservatives, fragrances, surfactants, etc.

The developer composition may be in the form of a powder, gel, liquid, foam, lotion, cream, mousse, or emulsion. In certain embodiments the developer composition is aqueous and is in the form of a liquid, cream, or emulsion. In other embodiments, the developer composition is anhydrous or substantially anhydrous.

Hair Color Altering Compositions

In various embodiments, the permanent hair color altering compositions according to the disclosure are hair dye compositions that may be prepared by mixing, at or near the time of use, a hair (color) base composition, a developer composition, and optionally a combination of citric acid and urea compounds, which may, for example, be in the form of a pre-phase mixture as described above. Alternatively, it is possible to mix a pre-phase mixture with a hair (color) base composition in advance, which is then mixed with the developer composition at or near the time of use. In a further alternate embodiment, it is possible to mix a pre-phase mixture developer composition which is then mixed with a hair (color) base composition at or near the time of use. In yet a further alternate embodiment, the citric acid and urea compounds may already be present in the hair (color) base composition, which is mixed with the developer composition at or near the time of use. In a still further alternate embodiment, the citric acid and urea compounds may already be present in the developer composition which is then mixed with a hair (color) base composition at or near the time of use.

According to various embodiments, the hair (color) base composition may be mixed with a developer composition at a ratio (hair (color) base or hair bleach to developer) ranging from about 1:5 to about 5:1, such as from about 1:4 to about 4:1, about 1:3 to about 3:1, or about 1:2 to about 2:1, or is, for example, about 5:1, about 4:1, about 3:1, about 2:1, about 1.5:1, about 1:1, about 1:1.5, about 1:2, about 1:3, about 1:4, or about 1:5. The citric acid and urea compounds may be included in such mixtures in amounts and ratios as described above.

By way of example only, a pre-mix of the combination of citric acid and at least one urea compound can be produced by combining and mixing particular amounts of citric acid and urea compounds with specific mole and/or weight ratios as described above to form a pre-phase mixture. The pre-phase mixture can then be added to the mixture of hair (color) base composition+developer composition in an amount ranging from about 0.5% to about 20%, including all ranges and subranges therebetween, such as from about 0.75% to about 15%, from about 1% to about 10%, from about 1.25% to about 9%, from about 1.5% to about 8%, from about 1.75% to about 7%, from about 2% to about 6%, from about 2.25% to about 5.5%, or from about 2.5% to about 5% by weight, relative to the total weight of the permanent hair color altering composition according to the disclosure, i.e. the mixture of hair (color) base composition+developer composition+pre-phase mixture.

In other embodiments, the permanent hair color altering compositions according to the disclosure are hair bleach compositions that may be prepared by mixing, at or near the time of use, a bleach composition, a developer composition, and optionally a combination of citric acid and urea compounds, which may, for example, be in the form of a pre-phase mixture as described above. Alternatively, it is possible to mix a pre-phase mixture with a bleach composition in advance, which is then mixed with the developer composition at or near the time of use. In a further alternate embodiment, it is possible to mix a pre-phase mixture developer composition which is then mixed with a bleach composition at or near the time of use. In yet a further alternate embodiment, the citric acid and urea compounds may already be present in the bleach composition, which is mixed with the developer composition at or near the time of use. In a still further alternate embodiment, the citric acid and urea compounds may already be present in the developer composition which is then mixed with a bleach composition at or near the time of use.

The bleach composition is typically mixed with a developer composition, and may be mixed in a ratio of bleach composition to developer composition ranging from about 1:1 to about 1:5, such as from about 1:1 to about 1:2, or about 1:2 to about 1:4, for example about 1:1, about 1:1.5, about 1:2, about 1:2.5, or about 1:3.

II. Methods

Compositions described herein surprisingly provide strength as well as a variety of other benefits such as better discipline, frizz control, shine, curl definition, smoothness, and/or softness, as well as other sensory benefits, to bleached and/or colored hair. Therefore, the disclosure also relates to methods for conditioning, treating, and/or caring for hair before and/or after the hair has been bleached and/or colored, or during the process of altering the color of the hair.

In some embodiments, the methods comprise applying an effective amount of a hair care or hair treatment composition according to the disclosure having a combination of citric acid and urea compounds to hair substantially immediately before the hair is bleached and/or colored, or substantially immediately after the hair is bleached and/or colored, e.g. as a "pre-treatment" and/or a "post-treatment" to a hair color altering process. As used herein, the term "effective amount" refers to an amount sufficient to provide a sensory property to the hair, depending on the length, the volume, and the texture of the hair. In general, from about 0.1 grams to about 50 grams of product is applied to the hair, depending on the specific product formulation, hair length, hair volume, and hair style type. In some embodiments, about 0.1 grams of the composition per gram of hair is applied to the hair. In some embodiments, about 5 grams of the composition per gram of hair is applied to the hair. As used herein, the term "substantially immediately" before or after hair is bleached and/or colored contemplates that a hair care/hair treatment composition is applied as a part of a hair bleaching or coloring process. For example, the hair care/hair treatment composition comprising a combination of citric acid and urea compounds may be applied within 6 hours or less, such as 3 hours or less, 2 hours or less, 1 hour or less, 45 minutes or less, 30 minutes or less, 20 minutes or less, 15 minutes or less, 10 minutes or less, or 5 minutes or less before and/or after the hair is bleached and/or colored.

As a non-limiting example, hair may be treated with a pre-treatment conditioning or care composition comprising a synergistic combination of citric acid and urea compounds, the composition rinsed from the hair, and then a color or bleaching process may be performed. As a further non-limiting example, a color or bleaching process may be performed, the color or bleaching composition rinsed from the hair, and then a post-treatment conditioning or care composition comprising a synergistic combination of citric acid and urea compounds may be applied to the hair. As yet a further non-limiting example, hair may be treated with a pre-treatment conditioning or care composition comprising a synergistic combination of citric acid and urea compounds, the composition rinsed from the hair, a color or bleaching process may be performed, and then a post-treatment conditioning or care composition comprising a synergistic combination of citric acid and urea compounds may be applied to the hair.

In further embodiments, the hair care/treatment compositions can be used to care for or treat previously bleached and/or color-treated hair. For example, the hair may have been bleached and/or colored more than 6 hours, more than 12 hours, more than 24 hours, more than 36 hours, more than 48 hours, more than 72 hours, more than 7 days, or more than 2 weeks before the hair care/treatment compositions are applied thereto. Surprisingly, even hair that has been previously bleached and/or color-treated demonstrates improved strength and/or other sensorial improvements once it is treated with hair care/treatment compositions as described herein.

In some embodiments, the hair care/treatment composition may be applied to hair that is shampooed and rinsed, and is still wet, but may also be applied to the hair that is dry, damp, or moist. The hair care/treatment composition applied to the hair may be distributed through the hair as desired, for example substantially evenly or uniformly massaged throughout the hair by combing through with fingers or a means such as a comb or the like. Typically, the hair care/treatment composition may be allowed to remain on the hair for a period of time ("leave-in" or "leave-on"), such as up to 2 hours, up to 1 hour, up to 45 minutes, up to 30 minutes, up to 20 minutes, up to 15 minutes, up to 10 minutes, up to 5 minutes, up to 2 minutes, or up to 1 minutes before it is rinsed from the hair. For example, the conditioning or care composition may be left on the hair for a period of time ranging from about 30 seconds to about 2 hours, such as from about 1 minute to about 1 hour, from about 2 minutes to about 45 minutes, from about 3 minutes to about 30 minutes, from about 4 minutes to about 15 minutes, or from about 5 minutes to about 10 minutes, including all ranges and subranges thereof.

In various embodiments, methods according to the disclosure relate to methods for conditioning, caring for, and/or treating hair comprising applying to the hair a conditioning, care, or treatment composition described herein. In other embodiments, the methods comprise imparting one of more of curl definition and/or curl retention, discipline, alignment, shine, frizz reduction, smoothness, softness, ease of detangling, and/or healthy look and feel to hair, for example hair that was previously damaged by a process for altering the color of hair such as coloring and/or bleaching by applying to the hair a conditioning, care, or treatment composition comprising a synergistic combination of citric acid and urea compounds as described herein. In still further embodiments, the methods comprise imparting one or more of long-lasting curl definition and/or curl retention, long-lasting discipline, long-lasting alignment, long-lasting shine, long-lasting frizz reduction, long-lasting smoothness, long-lasting softness, long-lasting ease of detangling, and/or long-lasting healthy look and feel to hair, which may, for example, last through at least 1 shampoo cycle, such as at least 2 shampoo cycles, at least 3 shampoo cycles, at least 4 shampoo cycles, or at least 5 shampoo cycles, by applying to the hair a conditioning, care, or treatment composition comprising a synergistic combination of citric acid and urea compounds as described herein, for example hair that was previously damaged by a process for altering the color of hair such as coloring and/or bleaching.

In other embodiments, the compositions comprise a temporary hair color altering composition comprising a combination of citric acid and urea compounds as described herein, and the methods comprise applying the temporary hair color altering composition to the hair and allowing it to remain on the hair for a period of time as needed to achieve a desired alteration in the color of the hair. The temporary hair color altering compositions are typically rinsed from the hair and the hair may then be dried and/or styled, as desired.

In further embodiments, the compositions comprise a temporary hair color altering composition that does not include a combination of citric acid and urea compounds. Thus, the methods comprise mixing a temporary hair color altering composition with a pre-phase mixture of citric acid and urea compounds as described herein, and applying the mixture to the hair and allowing it to remain on the hair for a period of time as needed to achieve a desired alteration in the color of the hair. The temporary hair color altering composition/pre-phase mixture is then typically rinsed from the hair and the hair may then be dried and/or styled, as desired.

In various embodiments, methods according to the disclosure relate to methods for temporarily altering the color of hair by applying to the hair a temporary hair color altering composition comprising a synergistic combination of citric acid and urea compounds as described herein. In other embodiments, the methods comprise imparting one of more of curl definition and/or curl retention, discipline, alignment, shine, frizz reduction, smoothness, softness, ease of detangling, and/or healthy look and feel to hair, while simultaneously temporarily altering the color of the hair by applying to the hair a temporary hair color altering composition comprising a synergistic combination of citric acid and urea compounds as described herein. In still further embodiments, the methods comprise imparting one or more of long-lasting curl definition and/or curl retention, long-lasting discipline, long-lasting alignment, long-lasting shine, long-lasting frizz reduction, long-lasting smoothness, long-lasting softness, long-lasting ease of detangling, and/or long-lasting healthy look and feel to hair, which may, for example, last through at least 1 shampoo cycle, such as at least 2 shampoo cycles, at least 3 shampoo cycles, at least 4 shampoo cycles, or at least 5 shampoo cycles, while simultaneously temporarily altering the color of the hair by applying to the hair a temporary hair color altering composition comprising a synergistic combination of citric acid and urea compounds as described herein. In further embodiments still, the methods comprise imparting long-lasting color to hair, which may, for example, last through at least one shampoo cycle, such as at least two shampoo cycles, at least 3 shampoo cycles, at least 5 shampoo cycles, at least 10 shampoo cycles, at least 15 shampoo cycles, or at least 20 shampoo cycles, while simultaneously altering the color of the hair by applying to the hair a semi- or demi-permanent hair color altering composition comprising a synergistic combination of citric acid and urea compounds as described herein.

In still further embodiments, the compositions comprise permanent hair color altering compositions and the methods comprise mixing a hair (color) base composition with a developer composition and adding a pre-phase mixture of citric acid and urea compounds as described herein to the mixture, and applying the mixture of hair (color) base composition+developer composition+pre-phase mixture to the hair. The mixture is typically allowed to remain on the hair for a period of time as needed to achieve a desired alteration in the color of the hair. The mixture is rinsed from the hair and the hair may then be dried and/or styled, as desired; alternatively, after the hair is rinsed, a hair care/treatment composition according to the disclosure may be applied to the hair as described herein.

In further embodiments still, the compositions comprise permanent hair color altering compositions and the methods comprise mixing a hair (color) base composition with a developer composition, which comprises citric acid and urea compounds as described herein, and applying the mixture to the hair. The mixture is allowed to remain on the hair for a period of time as needed to achieve a desired alteration in the color of the hair. The mixture is rinsed from the hair and the hair may then be dried and/or styled, as desired; alternatively, after the hair is rinsed, a hair care/treatment composition according to the disclosure may be applied to the hair as described herein.

In further embodiments still, the compositions comprise permanent hair color altering compositions and the methods comprise mixing a hair (color) base composition, which comprises citric acid and urea compounds as described herein, with a developer composition and applying the mixture to the hair. The mixture is allowed to remain on the hair for a period of time as needed to achieve a desired alteration in the color of the hair. The mixture is rinsed from the hair and the hair may then be dried and/or styled, as desired; alternatively, after the hair is rinsed, a hair care/treatment composition according to the disclosure may be applied to the hair as described herein.

In yet further embodiments, the compositions comprise permanent hair color altering compositions and the methods comprise mixing a bleach composition with a developer composition and adding a pre-phase mixture of citric acid and urea compounds as described herein to the mixture, and applying the mixture of bleach composition+developer composition+pre-phase mixture to the hair. The mixture is typically allowed to remain on the hair for a period of time as needed to achieve a desired alteration in the color of the hair. The mixture is rinsed from the hair and the hair may then be dried and/or styled, as desired; alternatively, after the hair is rinsed, a hair care/treatment composition according to the disclosure may be applied to the hair as described herein.

In further embodiments still, the compositions comprise permanent hair color altering compositions and the methods comprise mixing a bleach composition with a developer composition, which comprises citric acid and urea compounds as described herein, and applying the mixture to the hair. The mixture is allowed to remain on the hair for a period of time as needed to achieve a desired alteration in the color of the hair. The mixture is rinsed from the hair and the hair may then be dried and/or styled, as desired; alternatively, after the hair is rinsed, a hair care/treatment composition according to the disclosure may be applied to the hair as described herein.

In further embodiments still, the compositions comprise permanent hair color altering compositions and the methods comprise mixing a bleach composition, which comprises citric acid and urea compounds as described herein, with a developer composition and applying the mixture to the hair. The mixture is allowed to remain on the hair for a period of time as needed to achieve a desired alteration in the color of the hair. The mixture is rinsed from the hair and the hair may then be dried and/or styled, as desired; alternatively, after the hair is rinsed, a hair care/treatment composition according to the disclosure may be applied to the hair as described herein.

In various embodiments, methods according to the disclosure relate to methods for permanently altering the color of hair by applying to the hair a permanent hair color altering composition comprising a synergistic combination of citric acid and urea compounds as described herein. In further embodiments, the methods comprise imparting one of more of curl definition and/or curl retention, discipline, alignment, shine, frizz reduction, smoothness, softness, ease of detangling, and/or healthy look and feel to hair, while simultaneously permanently altering the color of the hair by applying to the hair a permanent hair color altering composition comprising a synergistic combination of citric acid and urea compounds as described herein. In still further embodiments, the methods comprise imparting one of more of long-lasting curl definition and/or curl retention, long-lasting discipline, long-lasting alignment, long-lasting shine, long-lasting frizz reduction, long-lasting smoothness, long-lasting softness, long-lasting ease of detangling, and/or long-lasting healthy look and feel to hair, which may, for example, last through at least 1 shampoo cycle, such as at least 2 shampoo cycles, at least 3 shampoo cycles, at least 4 shampoo cycles, or at least 5 shampoo cycles, while simultaneously permanently altering the color of the hair by applying to the hair a permanent hair color altering composition comprising a synergistic combination of citric acid and urea compounds as described herein.

According to some embodiments, when a coloring composition is applied on the hair, after an optional resting time ("leave-on time" or "processing" time), for example, ranging from about 1 to about 60 minutes, such as from about 5 to about 45 minutes, from about 10 to about 35 minutes, from about 15 to about 30 minutes, or from about 20 to about 30 minutes, including all ranges and subranges thereof, the hair is rinsed. In other embodiments, the processing time may range from about 5 minutes to about 80 minutes, from about 10 minutes to about 60 minutes, or from about 15 minutes to about 45 minutes, including all ranges and subranges thereof, before the hair is rinsed. The hair may further be optionally washed with shampoo, rinsed again, optionally washed with a hair conditioning composition, and/or rinsed again, then dried. The shampoo and hair conditioning composition can be any conventional hair shampoo and conditioner products.

The methods include, in various embodiments, methods of treating hair before, during, and/or after a process for altering the color of hair, methods of caring for hair before, during, and/or after a process for altering the color of hair, methods of coloring hair, methods of imparting strength to hair, and/or methods of imparting one or more benefits such as smoothness, shine, curl definition, reduced frizziness, softness, manageability, or the like to hair.

In some embodiments, for example, the methods may include application of more than one composition according to the disclosure to the hair. For example, in some embodiments, the methods may comprise a step of applying to the hair a temporary, semi- or demi-permanent, or permanent hair color altering composition comprising a synergistic combination of citric acid and urea compounds as described herein to the hair, and further comprise applying a hair conditioning, care, or treatment composition comprising a synergistic combination of citric acid and urea compounds as described herein to the hair before and/or after the step of applying the temporary, semi- or demi-permanent, or permanent hair color altering composition to the hair.

III. Kits

The disclosure also relates to kits. In certain embodiments, the kits include a first compartment or container containing a pre-phase mixture of citric acid and urea compounds as described herein, and at least one additional compartment or container containing a hair care/treatment composition, a temporary hair color altering composition, a hair (color) base composition, a bleach composition, or a developer composition. The kit may optionally further comprise instructions instructing a user regarding appropriate mixing steps, ratios, timing, etc.

In further embodiments, the kits may contain a first compartment or container containing a combination of citric acid and hydroxyethyl urea in a particular mole ratio or weight ratio as disclosed herein, a second compartment or container containing a base coloring composition comprising at least one component for coloring hair after the hair is bleached or colored, and a third compartment or container comprising a developing composition, or developer, comprising an oxidizing agent, as described herein. Furthermore, the kits may include an additional compartment or container containing pH adjusters, a tool for taking and dispensing the pH adjusters, and/or an indicator that show the pH value of a tested sample. In addition, the kits may contain an instruction for using the compositions comprised therein, such as instruction for mixing the combination of citric acid and hydroxyethyl urea, the base composition, and the developer at the time of use to obtain a coloring composition for treating hair after the hair is bleached and/or colored.

The disclosure also relates to kits comprising the compositions described herein. The kits in various embodiments may comprise at least one compartment or container suitable for containing and/or dispensing the compositions described herein for applying to the hair. In some other embodiments, a kit may comprise a first compartment or container containing a composition according to the disclosure, and at least one additional compartment or container comprising a composition according to the disclosure or a composition not according to the disclosure, such as, for example, a shampoo, a conditioner, a hair mask, or a hair styling composition.

In yet further exemplary embodiments, the disclosure relates to kits comprising at least two compartments or containers, where a first compartment or container comprises a pre-mix of a synergistic combination of citric acid and urea compounds as described herein, and at least a second compartment or container comprising a hair conditioning, care, or treatment composition comprising a synergistic combination of citric acid and urea compounds as described herein, a hair (color) base comprising a synergistic combination of citric acid and urea compounds as described herein, a bleach composition comprising a synergistic combination of citric acid and urea compounds as described herein, or a developer composition comprising a synergistic combination of citric acid and urea compounds as described herein. In further exemplary embodiments, the disclosure relates to kits comprising at least two compartments or containers, where a first compartment or container comprises a hair conditioning, care, or treatment composition comprising a synergistic combination of citric acid and urea compounds as described herein, a hair (color) base comprising a synergistic combination of citric acid and urea compounds as described herein, a bleach composition comprising a synergistic combination of citric acid and urea compounds as described herein, or a developer composition comprising a synergistic combination of citric acid and urea compounds as described herein, and at least a second compartment or container comprises a hair conditioning, care, or treatment composition comprising a synergistic combination of citric acid and urea compounds as described herein, a hair (color) base comprising a synergistic combination of citric acid and urea compounds as described herein, a bleach composition comprising a synergistic combination of citric acid and urea compounds as described herein, or a developer composition comprising a synergistic combination of citric acid and urea compounds as described herein different from the composition comprised in the first compartment or container. Thus, it should be understood that the disclosure also relates to various permutations of the aforementioned kits.

Having described the many embodiments of the present invention in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated. It is to be understood that all definitions herein are provided for the present disclosure only.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the compositions.

In this application, the use of the singular includes the plural unless specifically stated otherwise. The singular forms "a," "an," "the," and "at least one" are understood to encompass the plural as well as the singular unless the context clearly dictates otherwise. The expression "one or more" means "at least one" and thus includes individual components as well as mixtures/combinations. Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

As used herein, the phrases "and mixtures thereof," "and a mixture thereof," "and combinations thereof," "and a combination thereof," "or mixtures thereof," "or a mixture thereof," "or combinations thereof," and "or a combination thereof," are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. All ranges and amounts given herein are intended to include sub-ranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

As used herein, if a component is described as being present "in an amount up to" a certain amount, it is intended that such component is, in fact, present in the composition, i.e. is present in an amount greater than 0%.

"Active material" as used herein with respect to the percent amount of an ingredient or raw material, refers to 100% activity of the ingredient or raw material.

As used herein, a "leave-in" composition or product refers to a composition such as a hair-treatment that is not rinsed and/or washed away with water or acceptable solvent after the application of the composition onto the hair; instead, the composition is allowed to remain on the hair for a period of time as desired, such from 1 hour, 2 hours, 3 hours, 4 hours, up to 8 hours, overnight, or as long as needed, until next time of washing or rinsing the hair.

All amounts given herein are relative to the amount of active material, unless otherwise indicated.

All percentages, parts and ratios herein are based upon the total weight of the compositions of the present disclosure, unless otherwise indicated.

As used herein, hair with improved or enhanced curl definition may have curls with a shape that has a clean ringlet appearance rather than being frizzy, curls that appear more individualized, curls that are more closed in appearance, and/or curls that have an improved visual appearance of the hair color and/or highlights.

As used herein, the terms "applying a composition onto keratin fibers" and "applying a composition onto hair" and variations of these phrases are intended to mean contacting the keratin fibers including hair, with at least one of the compositions of the disclosure, in any manner. It may also mean contacting the keratin fibers in an effective amount of the composition.

As used herein, the term "conditioning" means imparting to hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work, and consumer perception.

As used herein, "cosmetic composition" encompasses many types of compositions for application to keratin materials such as skin or hair, for example, hair lotions, hair creams, hair gel creams, hair conditioners, hair masques (masks), etc., which can be used either as leave-on or rinse-off treatments or products.

As used herein, the term "inorganic" means a material that does not comprise carbon.

As used herein, the term "organic" means a material that is produced substantially without or essentially without the use of synthetic materials.

As used herein, the term "salts" refers to throughout the disclosure may include salts having a counter-ion such as an alkali metal, alkaline earth metal, or ammonium counterion. This list of counterions, however, is non-limiting. Salts also include a dissociated form of a compound, e.g. in an aqueous solution.

As used herein, the terms "substantially free" or "essentially free" mean the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in a raw material that is included in the composition.

As used herein, the terms "substantially without" or "essentially without" mean the specific material may be used in a manufacturing process in small amounts that do not materially affect the basic and novel characteristics of the compositions according to the disclosure. The terms may also mean that the specific material is not used in a manufacturing process but may still be present in a raw material that is included in the composition.

As used herein, the term "surfactants," as well as any specifically identified surfactants, includes salts of the surfactants even if not explicitly stated.

As used herein, the term "synthetic" means a material that is not of natural origin. The term "natural" and "naturally-sourced" means a material of natural origin, such as derived from plants, which also cannot be subsequently chemically or physically modified. "Plant-based" means that the material came from a plant.

As used herein, a "temporary" hair color altering composition is a composition that is not considered a permanent hair color altering composition by those skilled in the art. Typically, such compositions do not require the use of a developer composition.

As used herein, the term "treat" (and its grammatical variations) refers to the application of the compositions of the present disclosure onto the surface of keratin materials, such as hair.

As used herein, the terms "non-sulfate-based" or "non-sulfate" anionic surfactants mean that the surfactant does not comprise a sulfate group.

Unless otherwise expressly stated, it is in no way intended that any method set forth herein be construed as requiring that its steps be performed in a specific order. Accordingly, where a method claim does not expressly recite an order to be followed by its steps or it is not specifically stated in the claims or descriptions that the steps are to be limited to a specific order, it is no way intended that any particular order be inferred.

EXAMPLES

The following examples are intended to be non-limiting and explanatory in nature only. In the Examples, amounts in each composition are expressed in percentage by weight (wt %) of active materials, unless otherwise defined, relative to the total weight of the composition.

Example 1—Compositions for Treating Hair

Inventive compositions 1A and 1B and comparative compositions $C_1$ and $C_2$ having the formulations set forth in Table 1 were prepared.

TABLE 1

|  | Inventive Compositions | | Comparative Compositions | |
| --- | --- | --- | --- | --- |
|  | 1A | 1B | C1 | C2 |
| CITRIC ACID | 1.9 | 1.9 |  |  |
| HYDROXYETHYL UREA | 1.4 | 1.4 |  |  |
| CETYL ALCOHOL | 1.33 | 1 | 1.33 | 1 |
| CETEARYL ALCOHOL | 5 | 3.75 | 5 | 3.75 |
| AMODIMETHICONE (and) TRIDECETH-6 (and) CETRIMONIUM CHLORIDE | 2.67 | 2 | 2.67 | 2 |
| GUAR HYDROXYPROPYL-TRIMONIUM CHLORIDE | 0.13 | 0.1 | 0.13 | 0.1 |
| HYDROXYETHYL CELLULOSE | 0.27 | 0.2 | 0.27 | 0.2 |
| BEHENTRIMONIUM CHLORIDE | 3.47 | 2.6 | 3.47 | 2.6 |
| C12-15 ALKYL BENZOATE | 0.67 | 0.5 | 0.67 | 0.5 |
| CHLORHEXIDINE DIGLUCONATE | 0.27 | 0.2 | 0.27 | 0.2 |
| BASIC RED 51 |  | 0.08 |  | 0.08 |
| HC BLUE NO. 15 |  | 0.015 |  | 0.015 |
| pH Adjusters | <0.05 | <0.05 | <0.05 | <0.05 |
| WATER/AQUA | QS | QS | QS | QS |

First, a pre-mix of citric acid and hydroxyethyl urea (CA-HEU combination) that has a mole ratio of citric acid and/or salts thereof to hydroxyethyl urea of about 1:1.4 (corresponding to a weight ratio of citric acid and/or salts thereof to hydroxyethyl urea of about 1:0.75), was prepared by mixing 38% of citric and 62% of hydroxyethyl urea (45% active in water) at room temperature. Compositions C1 and C2 were used as base compositions for preparing composition 1A and composition 1B. Inventive composition 1A was prepared by mixing 95% of composition C1 and 5% of the CA-HEU pre-mix. Inventive composition 1B was prepared by mixing 95% of composition C2 and 5% of the CA-HEU pre-mix. All compositions 1A, 1B, C1, and C2 were acidic, with pH of about 3.5 to 4 at 25° C.

Example 1A—Treatment of Hair after Bleaching

The attributes imparted to hair by a post-bleaching treatment of inventive composition 1A were evaluated in comparison with comparative composition C1.

In a first set of testing, i.e., set (1), a pair or swatches of hair having loose curls were bleached, shampooed, and rinsed. Inventive composition 1A and comparative composition C1 were then separately applied to one of the two swatches that had been bleached, shampooed, and rinsed, at a rate of about 5 gram of composition per gram of hair, and were evenly distributed on the hair by combing with fingers and/or a combing device such as a comb. After a leave-on time of about 5 minutes, the swatches were rinsed with water and dried. Once dry, the swatches were evaluated.

In a second set of testing, i.e., set (2), a pair or swatches of hair without curls were platinum bleached, shampooed, and rinsed. Inventive composition 1A and comparative composition C1 were then separately applied to one of the two swatches that had been bleached, shampooed, and rinsed, at a rate of about 5 grams per gram of hair, and were evenly distributed on the hair by combing with fingers and/or a comb. After a leave-on time of about 5 minutes, the swatches were rinsed with water and dried. Once dry, these treated hair swatches were evaluated to assess the effects of composition 1A in comparison with composition C1. Images were taken for these hair swatches during evaluation and shown in FIG. 1A.

As seen in FIG. 1A, in set (1) and set (2), the bleached or platinum bleached hair swatches that were subsequently treated with inventive composition 1A have visually improved discipline, smoothness, curl definition, frizz control, alignment, and shine, compared to the hair swatches that were similarly bleached or platinum bleached but were treated with comparative composition C1. In addition, the hair treated with composition 1A felt smoother and softer and was less dry, compared to the hair treated with comparative composition C1.

A subsequent series of tests was performed on swatches of very curly hair that had been that had been bleached, shampooed, and rinsed, by applying equal amounts of inventive composition 1A, an inventive composition 1A-1 that is the same as 1A but included 1% citric acid and 0.7% hydroxyethyl urea, or comparative composition C1. After a leave-on time of about 5 minutes, the swatches were rinsed with water and dried.

Figure 1B:
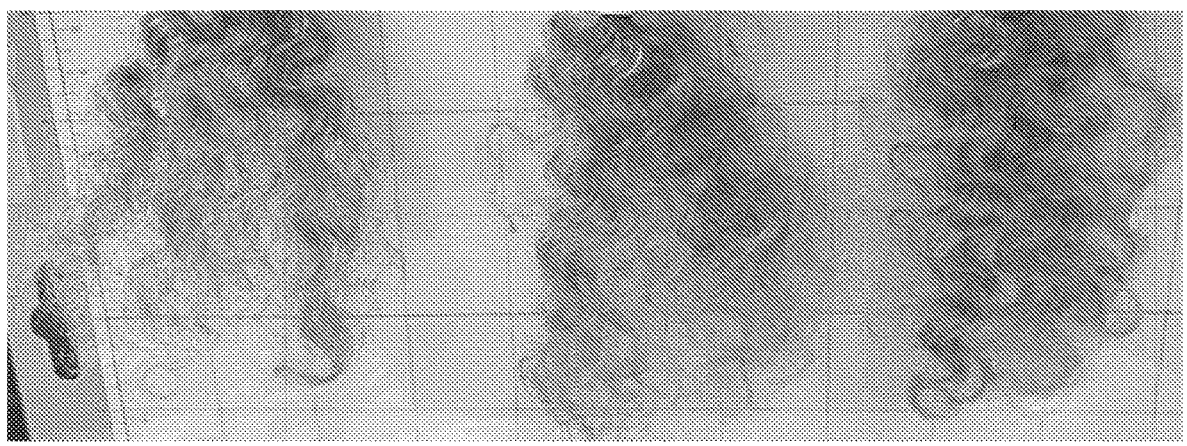

As shown in FIG. 1B, the bleached hair treated with inventive compositions 1A and 1A-1 demonstrate improved frizz control and curl definition than the hair treated with composition C1. In addition, the hair treated with inventive compositions 1A and 1A-1 was noticeably softer and smoother than the hair treated with composition C1.

This example demonstrates that, surprisingly and unexpectedly, including a synergistic combination of citric acid and a urea compound in a hair treatment composition provides improvement in attributes such as smoothness, frizz control, curl definition, discipline, shiness, and overall healthy look and feel to hair that was previously bleached, even at extreme platinum levels, compared to a hair treatment composition having the same components other than the synergistic combination of citric acid and urea compounds.

Example 1B—Treatment of Hair after Coloring

The attributes imparted to hair by a post-coloring treatment of inventive composition 1A were evaluated on a mannequin head with damaged hair due to previous coloring in comparison with comparative composition C1.

Inventive composition 1A was applied on wet hair of one half of the head of a mannequin head and evenly distributed on the hair, and the same amount of comparative composition C1 was applied on wet hair of the other half of the head and evenly distributed on the hair. Each composition was applied in an amount of about 5 grams per gram of hair. Both inventive composition 1A and comparative composition C1 were allowed to remain on the hair for about 5 minutes, followed by thorough rinsing and drying. The hair was evaluated while the hair was still wet and after the hair were dried.

Figure 2:
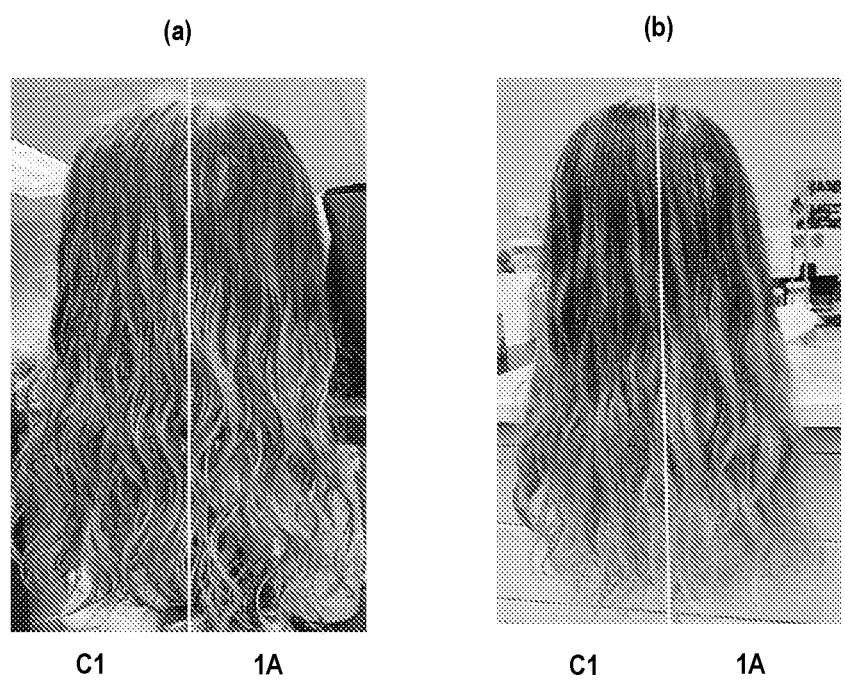
FIG. 2 is a set of images showing pre-colored hair of a mannequin head that was treated with an exemplary hair care/treatment composition according to the disclosure in comparison with a comparative composition outside the disclosure.

FIG. 2 shows the images of the head when the treated hair was still wet and after the hair was dried. Image (a) shows the half-head treated with composition 1A or C1, compared side by side, when the hair was still wet. Image (b) shows the half-head treated with composition 1A or C1, compared side by side, when the hair was dried. As seen in FIG. 2, for both the wet or dry evaluations the hair treated with inventive composition 1A looks less frizzy, has better discipline and smoothness, as well as better curl definition, compared to the hair treated with comparative composition C1.

This example demonstrates that, surprisingly and unexpectedly, including a synergistic combination of citric acid and a urea compound in a hair treatment composition provides attributes such as improved smoothness, frizz control, discipline, softness, and overall healthy look and feel to hair that was previously damaged by coloring, compared to a composition having the same components other than the synergistic combination of citric acid and urea compounds.

Example 1C—Treatment of Hair During Coloring

The attributes imparted to hair during coloring by inventive composition 1B were evaluated in comparison with comparative composition C2.

Inventive composition 1B and comparative composition C2 were applied to separate swatches of platinum bleached hair with or without loose curls, at a rate of about 5 grams per gram of hair, to determine the efficacy of color deposit and the attributes imparted on the hair by the compositions. Both inventive composition 1B and comparative composition C2 were allowed to remain on the hair for about 20-30 minutes, followed by thorough rinsing and drying the hair swatches. After the swatches were dried, coloring properties were evaluated. Images were taken for these hair swatches during evaluation and shown in FIG. 3.

Figure 3:
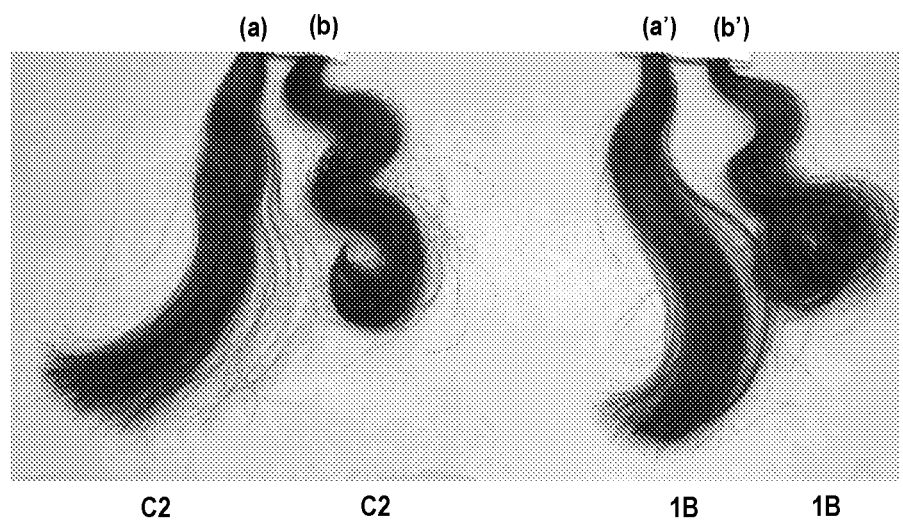
FIG. 3 is a set of images showing pre-bleached hair swatches treated with an exemplary temporary hair color altering composition according to the disclosure during coloring, in comparison with a comparative temporary hair color altering composition outside the disclosure.

In FIG. 3, swatches (a) (platinum bleached) and (b) (loose curls, bleached) were treated with comparative composition C2; swatches (a') (platinum bleached) and (b') (loose curls, bleached) were treated with inventive composition 1B. As seen in FIG. 3, similar color results on all swatches were obtained with either inventive composition 1B or comparative composition C2. However, swatches (a') and (b'), which were treated with inventive composition 1B, show visibly improved discipline, curl definition, and frizz control, compared to swatches (a) and (b) treated with comparative composition C2. In addition, the swatches treated with composition 1B had improved softness compared to the swatches treated with composition C2.

This example demonstrates that, surprisingly and unexpectedly, including a synergistic combination of citric acid and a urea compound in a semi-permanent hair color composition provides attributes such as improved smoothness, frizz control, curl/wave definition, discipline, softness, and overall healthy look and feel to hair compared to a composition having the same components other than the synergistic combination of citric acid and urea compounds, while at the same time similarly altering the color of the hair.

Example 2—Compositions for Treating Previously-Bleached Hair

Exemplary hair color toning/shine compositions were prepared using developer composition D1 or D2 set forth in Table 2A, hair coloring base composition CB1 or CB2 set forth in Table 2B, and a CA-HEU pre-mix as described above in Example 1.

TABLE 2A

| | Developer Composition | |
|---|---|---|
| | D1 | D2 |
| TRIDECETH-2 CARBOXAMIDE MEA | 0.9 | 0.9 |
| TETRASODIUM ETIDRONATE | 0.06 | 0.2 |
| SODIUM SALICYLATE | 0.04 | 0.04 |
| GLYCERIN | 0.5 | 0.5 |
| CETEARYL ALCOHOL | 2.3 | 2.3 |
| CETEARETH-25 | 0.6 | 0.6 |
| HYDROGEN PEROXIDE | 3 | 6 |
| TETRASODIUM PYROPHOSPHATE | 0.04 | 0.04 |
| WATER | QS | QS |

TABLE 2B

| | Hair Color Base | |
|---|---|---|
| | CB1 | CB2 |
| CETYL HYDROXYETHYLCELLULOSE | 0.4 | 0.4 |
| POLYQUATERNIUM-6 | 0.8 | 2 |
| 2-OLEAMIDO-1,3-OCTADECANEDIOL | 0.01 | 0.01 |
| GLYCERIN | 3 | 3 |
| EDTA | 0.2 | 0.2 |
| TETRASODIUM EDTA | 0.001 | |
| LAURETH-2 | 8 | 8 |
| LAURETH-12 | 3 | 3 |
| OLETH-30 | 2 | 2 |
| SODIUM CETEARYL SULFATE | 1.5 | 1.5 |
| SODIUM SULFITE | 0.1 | 0.1 |
| PEG-4 RAPESEEDAMIDE | 7.4 | 8 |
| CITRIC ACID | 0.1 | 0.1 |
| PRUNUS PERSICA (PEACH) KERNEL OIL | 0.1 | 0.1 |
| ERYTHORBIC ACID | 0.4 | 0.4 |
| TAURINE | 0.001 | 0.001 |
| ETHANOLAMINE | 0.2 | 0.2 |
| PLANT EXTRACTS | | 0.3 |
| WATER | QS to 100 | QS to 100 |

Composition D1 is a 10V aqueous hydrogen peroxide oxidizing composition. Composition D1 had a viscosity at 25° C. of about 30 UD (M2) to about 50 UD (M2), and a pH of 2.2±0.2.

The viscosity of composition CB1 at 25° C. was about 10 UD (M4) to about 30 UD (M4).

As shown in Table 2C, coloring compositions 2A-2D according to the disclosure were prepared by mixing equal amounts of hair color base CB1 and developer D1, and adding the CA-HEU pre-mix as described in Example 1 as indicated. Comparative composition C3 was prepared by combining equal amounts of base composition CB1 and developer D1, without adding the CA-HEU pre-mix. All of compositions 2A-2D and C3 were prepared at the time of use, i.e., right before application to the hair.

TABLE 2C

|  | Inventive Compositions | | | | Comparative Composition |
| --- | --- | --- | --- | --- | --- |
|  | 2A | 2B | 2C | 2D | C3 |
| Pre-mix: Citric Acid + Hydroxyethyl Urea* | 2.5 | 2.5 | 5 | 5 |  |
| Hair Color Base CB1 | 48.75 | 48.75 | 47.5 | 47.5 | 50% |
| Developer D1 | 48.75 | 48.75 | 47.5 | 47.5 | 50% |
| Ethanolamine (MEA) |  | QS |  | QS |  |
| pH** | 6.44 | 3.14 | 6.3 | 2.75 | 6.4 |

*mole ratio of CA:HEU = 1:1.4
**pH was adjusted using an appropriate amount of ethanolamine (MEA)

Sensory benefits, color, and shade coverage imparted to previously processed hair by compositions 2A-2D were evaluated in comparison with composition C3.

Example 2A: Color Toning

Equal amounts of one of compositions 2A-2D were separately applied to two swatches of double bleached hair (level 6), and evenly distributed by combing and/or massaging with fingers or a comb. The composition was left on the swatch of hair for about 20 to 30 minutes, followed by shampooing, rinsing, and drying the hair. After the swatches were completely dried, the swatches were evaluated for toning properties and other attributes, such as color evenness and shine. Images of the swatches were taken and shown in FIG. 4.

Figure 4:
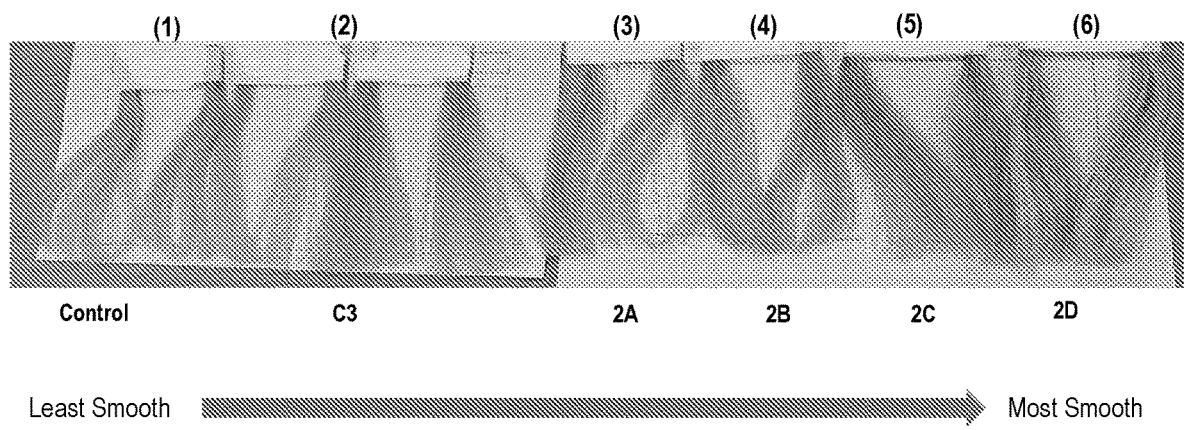
FIG. 4 is a set of images showing hair swatches treated with exemplary color toning compositions according to the disclosure in comparison with a control swatch and a swatch treated with a comparative color toning composition outside the disclosure.

In FIG. 4, the pair of swatches in group (1) corresponds to untreated control swatches, two pairs of swatches in group (2) correspond to swatches treated with comparative composition C3, and the pairs of swatches in groups (3), (4), (5), and (6) correspond to swatches respectively treated with inventive compositions 2A-2D. As shown, the swatches exhibit increased smoothness from group (1) to group (6), with the least smooth in group (1) and most smooth in group (6). Further, it was reported that the hair in group (1) had a dull and powdery feeling; the hair in group (4) had smoother ends; the hair in group (5) was silky with explosive "plump" mass; and the hair in group (6) was silky with a cleaner appearance. Overall, the bleached hair treated with compositions 2A-2D according to the disclosure show visibly improved color evenness, as well as smoothness, frizz control, manageability, discipline (e.g., no "fly-aways"), softness, and shaping, compared to untreated bleached hair (control) or bleached hair treated with the comparative composition not including the synergistic combination of citric acid and urea compounds.

Example 2B: Shine Service

Inventive composition 2E (pH 2.8) was prepared by mixing equal amounts of base composition CB2 and developer D2, and adding 5% of the CA-HEU pre-mix described in Example 1. Comparative composition C4 (pH 6.4) was prepared by combining equal amounts of base composition CB2 and developer D2, but without adding the CA-HEU pre-mix.

Inventive composition 2E and comparative composition C4 were applied to dry hair on opposite sides of the head of six volunteers with bleached hair and allowed to remain on the hair for 20 minutes. The hair was then rinsed, shampooed, rinsed again, and dried.

Figure 5:
FIG. 5 shows images of hair of a volunteer (half-head study) immediately after treatment with a composition according to the disclosure compared to a composition not according to the disclosure, and again one week after treatment.
Figure 5:

FIG. 5 shows photographs of the hair of one volunteer immediately after treatment (a) and again one week after treatment (b). The hair treated with inventive composition 2E of all six volunteers had noticeably better smoothness, discipline, alignment, and shine than the hair treated with comparative composition C4. In addition, the expert reported that inventive composition 2E was easier to apply than composition C4, and that the hair treated with inventive composition 2E was easier to detangle than the hair treated with composition C4, for all six volunteers.

The volunteers were instructed to continue their standard hair care routine and return for re-evaluation after one week. As can be seen in FIG. 5, these results remained even after one week, which was surprising. The results similarly lasted for the remaining volunteers.

This protocol was repeated on swatches of bleached hair, with the same surprising and lasting results.

These examples demonstrate that including a synergistic combination of citric acid and urea compounds in a hair color altering or shine composition surprisingly and unexpectedly improves overall properties of the coloration and tone of bleached hair while providing an improved healthy look and feel, less frizz, improved softness and shine, better discipline, and ease of detangling, which results surprisingly last through several typical shampoo/rinse/dry and hair styling cycles.

Example 3—Permanent Hair Dye Compositions

Exemplary permanent hair dye compositions were prepared to evaluate the impact of including a synergistic combination of citric acid and urea compounds on the color efficacy and hair properties using compositions and processes for permanently altering the color of hair.

Example 3A

A permanent hair dye composition was prepared using developer composition D3 (20V) set forth in Table 3A, hair coloring base composition CB3 set forth in Table 3B, and a CA-HEU pre-mix as described above in Example 1.

TABLE 3A

|  | Developer Composition D3 |
| --- | --- |
| TRIDECETH-2 CARBOXAMIDE MEA | 0.85 |
| TETRASODIUM ETIDRONATE | 0.06 |
| SODIUM SALICYLATE | 0.035 |
| GLYCERIN | 0.5 |
| CETEARYL ALCOHOL | 2.28 |
| CETEARETH-25 | 0.57 |
| HYDROGEN PEROXIDE | 12 |
| TETRASODIUM PYROPHOSPHATE | 0.04 |
| WATER | QS |

TABLE 3B

| | Hair Color Base CB3 |
|---|---|
| TOLUENE-2,5-DIAMINE (and) THIOGLYCERIN | 1.4 |
| HYDROXYBENZOMORPHOLINE | 1 |
| 2,4-DIAMINOPHENOXYETHANOL HCl | 0.1 |
| DECETH-3 | 7.7 |
| PRUNUS ARMENIACA (APRICOT) KERNEL OIL | 2 |
| ERYTHORBIC ACID | 0.3 |
| 6-HYDROXYINDOLE | 0.1 |
| N,N-BIS(2-HYDROXYETHYL)-p-PHENYLENEDIAMINE SULFATE | 0.1 |
| 2-AMINO-3-HYDROXYPYRIDINE | 0.04 |
| SODIUM METABISULFITE | 0.5 |
| OLEYL ALCOHOL | 1.1 |
| m-AMINOPHENOL | 0.5 |
| ETHANOLAMINE | 9.8 |
| PEG-4 RAPESEEDAMIDE | 13 |
| LAURETH-5 CARBOXYLIC ACID | 5 |
| TETRASODIUM GLUTAMATE DIACETATE | 0.5 |
| POLOXAMER 338 | 2 |
| SOLVENT (water and non-aqueous solvents) | QS to 100 |

Inventive composition 3A (pH 9.7) was prepared by mixing equal amounts of base composition CB3 and developer D3, and adding 2.5% of the CA-HEU pre-mix described in Example 1. Comparative composition $C_4$ (pH 10.1) was prepared by combining equal amounts of base composition CB3 and developer D3, but without adding the CA-HEU pre-mix. Both compositions were prepared just prior to application to the hair.

Inventive composition 3A and comparative composition C4 were applied to opposite sides of the head of volunteers having very curly hair. Both inventive composition 3A and comparative composition C4 were allowed to remain on the hair for about 20-30 minutes, followed by thorough rinsing and drying the hair. Professional colorists then evaluated the efficacy of color deposit and the attributes imparted to the hair by the inventive and comparative compositions.

Figure 6A:
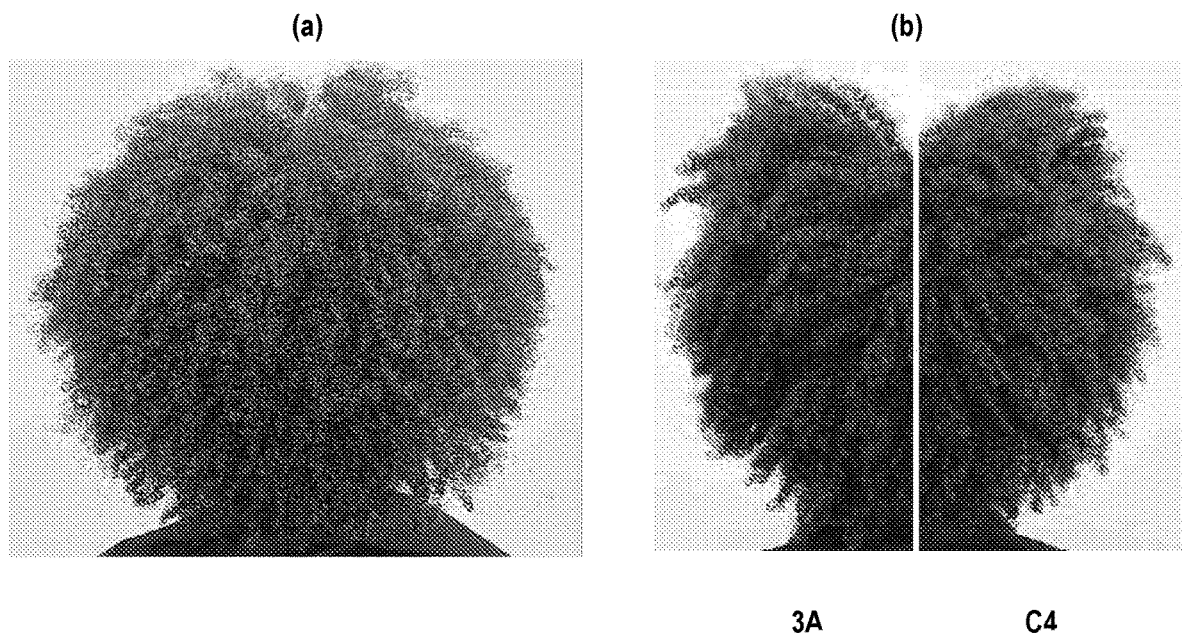
FIGS. 6A-6B show before and after images of the hair of two volunteers whose hair was dyed with an exemplary permanent hair dye according to the disclosure compared to a permanent dye not according to the disclosure.
Figure 6B:
Figure 6B:

FIGS. 6A-6B show before (a) and after (b) photographs of the hair of two volunteers. The professional reported that hair treated with inventive composition 3A had noticeably deeper color with better color uniformity, and appeared healthier with better curl definition compared to hair treated with comparative composition C4 in both studies.

Example 3B

A permanent hair dye composition was prepared using developer composition D3 (Table 3A) (20V) and hair coloring base composition CB4 (Table 3C).

TABLE 3C

| | Hair Color Base CB4 |
|---|---|
| GLYCERIN | 3 |
| PEG-2 OLEAMINE | 3 |
| COCAMIDE MEA | 18 |
| CETEARYL ALCOHOL (and) BEHENTRIMONIUM METHOSULFATE | 2.5 |
| CETYL ESTERS (and) CETYL ESTERS | 1 |
| STEARAMIDE MEA (and) ETHANOLAMINE | 6 |

TABLE 3C-continued

| | Hair Color Base CB4 |
|---|---|
| DILINOLEIC ACID | 5 |
| ETHANOLAMINE | 1.2 |
| 2-OLEAMIDO-1,3-OCTADECANEDIOL | 0.01 |
| ASCORBIC ACID | 0.5 |
| SODIUM SULFITE | 0.5 |
| N,N-BIS(2-HYDROXYETHYL)-p-PHENYLENEDIAMINE SULFATE | 0.04 |
| m-AMINOPHENOL | 0.02 |
| RESORCINOL | 0.3 |
| p-PHENYLENEDIAMINE | 0.2 |
| p-AMINOPHENOL (and) SODIUM METABISULFITE | 0.04 |
| DISODIUM WHEATGERMAMPHODIACETATE | 3 |
| POLYQUATERNIUM-22 | 3 |
| AMMONIUM HYDROXIDE | 10 |
| HEXADIMETHRINE CHLORIDE | 0.5 |
| SIMMONDSIA CHINENSIS (JOJOBA) SEED OIL OIL | 0.2 |
| ADDITIVES (preservatives, fragrance, amino acids) | <1 |
| SOLVENTS (water and non-aqueous solvents) | QS to 100 |

Inventive composition 3B (pH 9.6) was prepared by mixing equal amounts of base composition CB4 and developer D3, and adding 2.5% of the CA-HEU pre-mix described in Example 1 just prior to application to hair.

Inventive composition 3B was applied to dry hair of a human volunteer and allowed to remain on the hair for 35 minutes, the hair was then rinsed, washed with a standard shampoo, and dried. The hair treated with inventive composition 3B showed excellent smoothness, shine, and discipline, and it was noted that the hair had excellent uniformity of color.

These examples demonstrate that including a synergistic combination of citric acid and urea compounds in a permanent hair dye composition surprisingly and unexpectedly improves the color depth and uniformity of the treated hair, as well as providing an improved healthy look and feel to hair.

Example 4—Hair Treatment Compositions

Compositions for improving the condition of hair that has been damaged (e.g. previously colored and/or bleached) having the following components were evaluated. Comparative composition C5 has the components shown in Table 4. Inventive composition 4A was prepared by adding 5% of CA-HEU premix prepared as in Example 1 to composition C5.

TABLE 4

Hair Treatment Composition C5

WATER, CETEARYL ALCOHOL, DIMETHICONE, GLYCERIN, BEHENTRIMONIUM CHLORIDE, FRAGRANCE, AMODIMETHICONE, CETRIMONIUM CHLORIDE, PHENOXYETHANOL, ISOPROPYL ALCOHOL, SODIUM LAURETH SULFATE, LACTIC ACID, LINALOOL, HEXYL CINNAMAL, BENZYL SALICYLATE, BENZYL ALCOHOL, LIMONENE, HYDROXYPROPYLTRIMONIUM HYDROLYZED WHEAT PROTEIN, AMYL CINNAMAL, COUMARIN, CITRONELLOL, ALPHA-ISOMETHYL IONONE, 2-OLEAMIDO-1,3-OCTADECANEDIOL, GERANIOL, ISOEUGENOL

Figure 7:
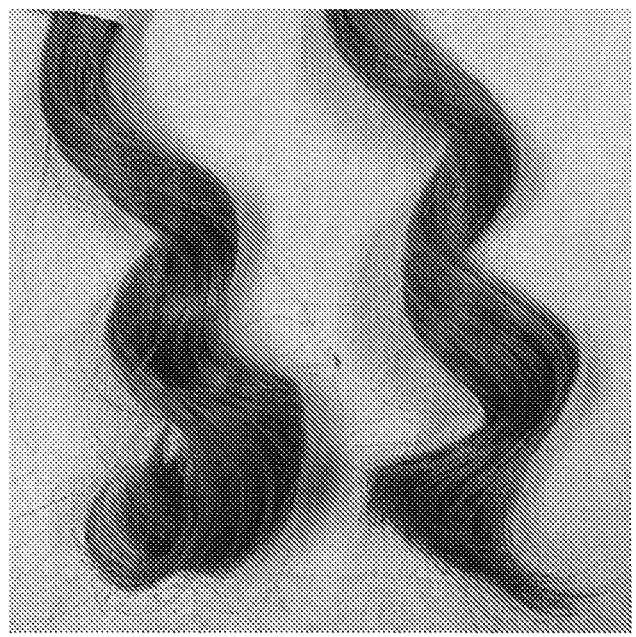
FIG. 7 is an image of two swatches of bleached hair that were treated with an exemplary conditioning composition according to the disclosure compared to a swatch treated with a conditioning composition not according to the disclosure.

Equal amounts of compositions 4A and C5 were applied to separate swatches of loose curl pattern bleached hair (level 4), and evenly distributed by combing and/or massaging with fingers or a comb. The composition was left on the swatch of hair for about 5 minutes, after which the hair was rinsed and dried. After the swatches were completely dried, the swatches were evaluated. Images of the swatches are shown in FIG. 7.

The swatch treated with inventive composition 4A demonstrated noticeably improved curl definition, discipline, shine, and more compact ends than the swatch treated with comparative composition C5. In addition, the swatch treated with composition 4A had a much smoother feel than the swatch treated with composition C5.

Both inventive composition 4A and comparative composition C5 had a pH in the range of 3-4. Notably, inventive composition 4A was stable.

This example demonstrates that a hair conditioning composition that includes a synergistic combination of citric acid and urea compounds surprisingly and unexpectedly improves the look and feel of the hair, and imparts better curl definition, compared to an identical hair conditioning composition not including the combination.

Example 5—Color Retention Studies

The following studies were performed to evaluate the impact on lastingness of color when synergistic combinations of citric acid and urea compounds were included in hair coloring compositions.

Example 5A—One-Week Study

A study was performed to determine the lastingness of color after a period of one week of an ordinary shampoo/rinse/dry/style routine. Exemplary demi-permanent hair dye compositions were prepared using developer composition D2 (Table 2A) (10V), hair coloring base composition CB5 set forth in Table 5A, and a CA-HEU pre-mix as described above in Example 1.

TABLE 5A

| | Hair Color Base CB5 |
|---|---|
| RESORCINOL | 1 |
| m-AMINOPHENOL | 0.1 |
| SODIUM METABISULFITE | 0.7 |
| ETHANOLAMINE | 4.6 |
| OLETH-30 | 4 |
| GLYCOL DISTEARATE | 2 |
| LAURIC ACID | 3 |
| LAURETH-12 | 7 |
| CETEARYL ALCOHOL | 11.5 |
| HYDROXYBENZOMORPHOLINE | 0.01 |
| SILICA DIMETHYL SILYLATE | 1.2 |

TABLE 5A-continued

| | Hair Color Base CB5 |
|---|---|
| 2,4-DIAMINOPHENOXYETHANOL HCL | 0.02 |
| DECETH-3 | 10 |
| HEXADIMETHRINE CHLORIDE | 2 |
| POLYQUATERNIUM-6 | 4 |
| POLYQUATERNIUM-22 | 1 |
| PRUNUS ARMENIACA (APRICOT) KERNEL OIL | 0.1 |
| CARBOMER | 0.4 |
| ERYTHORBIC ACID | 0.3 |
| MICA (and) TITANIUM DIOXIDE/MICA (and) CI 77891 | 0.5 |
| 2-OLEAMIDO-1,3-OCTADECANEDIOL | 0.01 |
| PRUNUS PERSICA (PEACH) KERNEL OIL | 0.1 |
| TOLUENE-2,5-DIAMINE (and) THIOGLYCERIN | 1 |
| ADDITIVES (preservatives, fragrance, amino acids) | <1 |
| SOLVENTS (water and non-aqueous solvents) | QS to 100 |

Inventive composition 5A (pH 7.4) was prepared by mixing equal amounts of base composition CB5 and developer D2, and adding 2.5% of CA-HEU pre-mix described in Example 1. Comparative composition C6 (pH 9.5) was prepared by combining equal amounts of base composition CB5 and developer D2, but without adding the CA-HEU pre-mix. Both compositions were prepared just prior to application to the hair.

Figure 8:
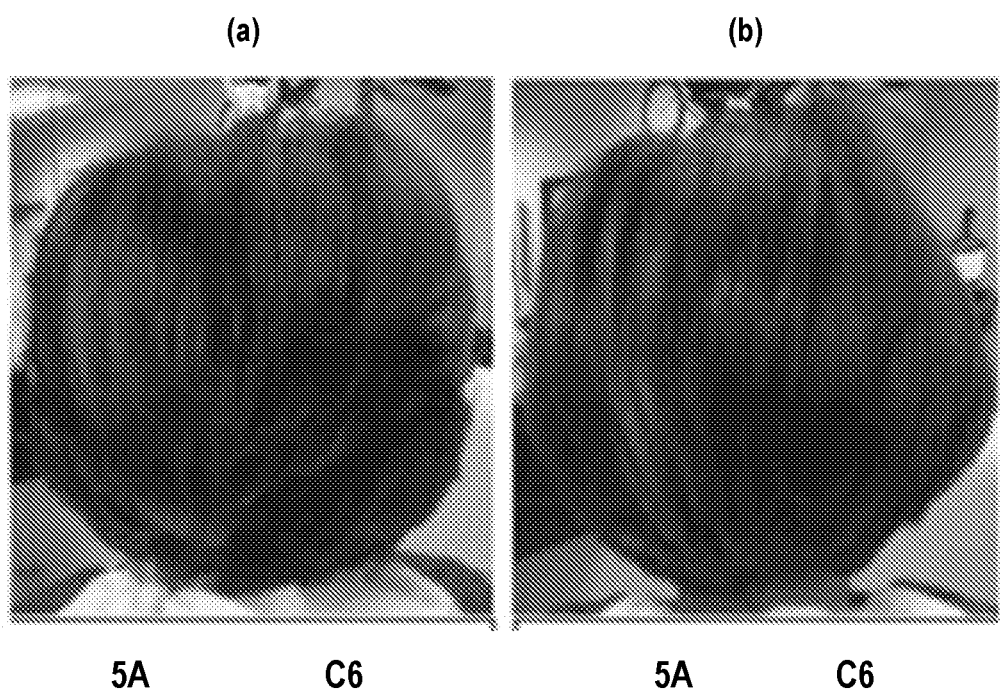
FIG. 8 shows images of hair of a volunteer (half-head study) immediately after treatment with a dye composition according to the disclosure compared to a dye composition not according to the disclosure, and again one week after treatment.

Inventive composition 5A and comparative composition C6 were applied to dry hair on opposite sides of the head of six volunteers. Both inventive composition 5A and comparative composition C6 were allowed to remain on the hair for 20 minutes, followed by thorough rinsing, shampooing, and drying the hair. The efficacy of color deposit and the attributes imparted to the hair by the inventive and comparative compositions were evaluated both immediately after treatment and again after one week of the volunteer's normal hair care routine. Images of the hair of one volunteer are shown in FIG. 8, where (a) is the hair immediately after treatment and (b) is the hair after one week.

Inventive composition 5A was easier to apply and imparted noticeably better color deposition and ease of detangling, as well as improved smoothness, discipline, shine, and alignment of hairs compared to the hair treated with comparative composition C6, for all volunteers. In addition, the hair of all volunteers treated with composition 5A had better uniformity of color. These results surprisingly persisted after one week. Also surprisingly, the color of the hair treated with composition 5A was more consistent with the color of the hair immediately after treatment compared to the hair treated with composition C6, which had noticeable color fade after one week, as seen in FIG. 8.

Example 5B—Additional Studies

Additional studies were performed to determine the lastingness of color through twenty (20) shampoo/rinse cycles.

Exemplary demi-permanent hair dye compositions were prepared using developer and hair color base compositions as follows.

Inventive composition 5B (pH 7.4) was prepared by mixing equal amounts of developer D2 (Table 2A) (10V) and base composition CB6 (Table 5B), and adding 2.5% of CA-HEU pre-mix described in Example 1. Comparative composition C7 (pH 9.5) was prepared by combining equal amounts of base composition CB6 and developer D2, but with additional water in place of the CA-HEU pre-mix.

TABLE 5B

| | Hair Color Base CB6 |
|---|---|
| SODIUM METABISULFITE | 0.7 |
| ETHANOLAMINE | 5.1 |
| p-AMINOPHENOL (and) SODIUM METABISULFITE | 0.4 |
| OLETH-30 | 4 |
| GLYCOL DISTEARATE | 2 |
| LAURIC ACID | 3 |
| LAURETH-12 | 7 |
| CETEARYL ALCOHOL | 11.5 |
| SILICA DIMETHYL SILYLATE | 1.2 |
| 2-METHYL-5-HYDROXYETHYLAMINOPHENOL | 0.13 |
| DECETH-3 | 10 |
| HEXADIMETHRINE CHLORIDE | 2 |
| POLYQUATERNIUM-6 | 4 |
| POLYQUATERNIUM-22 | 1 |
| PRUNUS ARMENIACA (APRICOT) KERNEL OIL | 0.1 |
| CARBOMER | 0.6 |
| ERYTHORBIC ACID | 0.3 |
| MICA (and) TITANIUM DIOXIDE/MICA (and) CI 77891 | 0.5 |
| 4-AMINO-2-HYDROXYTOLUENE | 0.6 |
| 2-OLEAMIDO-1,3-OCTADECANEDIOL | 0.01 |
| PRUNUS PERSICA (PEACH) KERNEL OIL | 0.1 |
| TOLUENE-2,5-DIAMINE (and) THIOGLYCERIN | 0.14 |
| 2,3-DIAMINODIHYDROPYRAZOLO PYRAZOLONE DIMETHOSULFONATE | 0.28 |
| ADDITIVES (preservatives, fragrance, amino acids) | <1 |
| SOLVENTS (water and non-aqueous solvents) | QS to 100 |

Inventive composition 5C (pH 7.4) was prepared by mixing equal amounts of developer D2 (Table 2A) (10V) and base composition CB7 (Table 5C), and adding 2.5% of CA-HEU pre-mix described in Example 1. Comparative composition C8 (pH 9.5) was prepared by combining equal amounts of base composition CB7 and developer D2, but with additional water in place of the CA-HEU pre-mix.

TABLE 5C

| | Hair Color Base CB7 |
|---|---|
| SODIUM METABISULFITE | 0.7 |
| ETHANOLAMINE | 5.3 |
| p-AMINOPHENOL (and) SODIUM METABISULFITE | 0.2 |
| OLETH-30 | 4 |
| GLYCOL DISTEARATE | 2 |
| LAURIC ACID | 3 |
| LAURETH-12 | 7 |
| CETEARYL ALCOHOL | 11.5 |
| SILICA DIMETHYL SILYLATE | 1.2 |
| DECETH-3 | 10 |
| HEXADIMETHRINE CHLORIDE | 2 |
| POLYQUATERNIUM-6 | 4 |
| POLYQUATERNIUM-22 | 1 |
| PRUNUS ARMENIACA (APRICOT) KERNEL OIL | 0.1 |
| CARBOMER | 0.4 |
| ERYTHORBIC ACID | 0.3 |
| MICA (and) TITANIUM DIOXIDE/MICA (and) CI 77891 | 0.5 |
| 4-AMINO-2-HYDROXYTOLUENE | 1.4 |

TABLE 5C-continued

| | Hair Color Base CB7 |
|---|---|
| 2-OLEAMIDO-1,3-OCTADECANEDIOL | 0.01 |
| PRUNUS PERSICA (PEACH) KERNEL OIL | 0.1 |
| TOLUENE-2,5-DIAMINE (and) THIOGLYCERIN | 0.5 |
| HYDROXYETHOXY AMINOPYRAZOLOPYRIDINE HCL | 1 |
| ADDITIVES (preservatives, fragrance, amino acids) | <1 |
| SOLVENTS (water and non-aqueous solvents) | QS to 100 |

Prior to the study, the color of swatches of permed, 90% grey hair was evaluated using the L*a*b* system (time=−1). Compositions 5B-5C and C7-C8 were applied to separate swatches. The compositions were allowed to remain on the hair for 20 minutes, after which time the hair was rinsed and dried. The color of the swatches was then evaluated again (time=0).

Figure 9A:
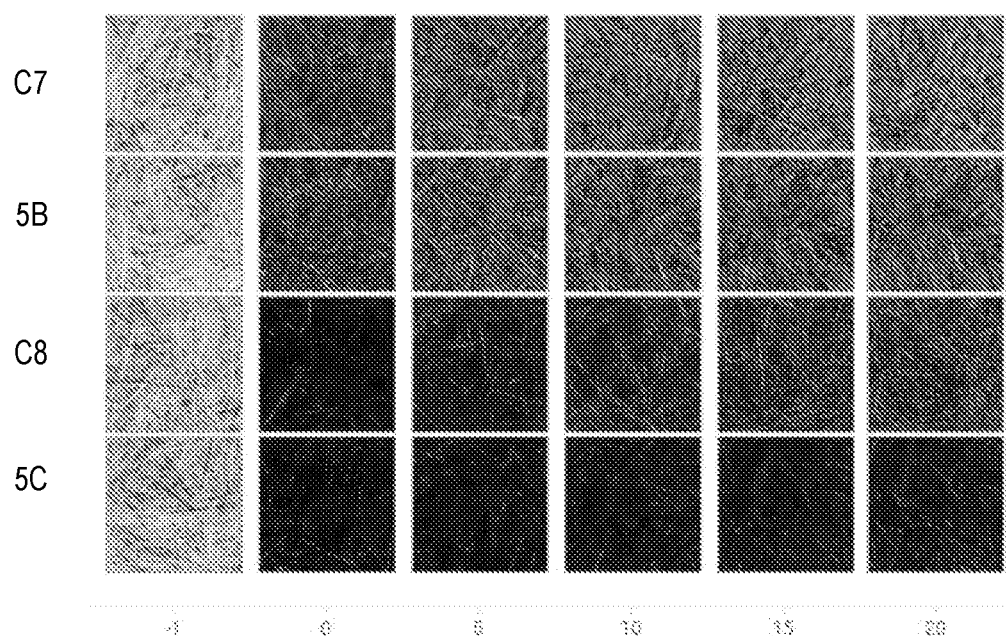
FIGS. 9A-9B show images (9A) and a graph (9B) of a study of color retention of hair treated with dye compositions according to the disclosure compared to dye compositions not according to the disclosure, over several wash cycles.

Next, the swatches were shampooed with a commercial shampoo by massaging equal amounts of shampoo onto each swatch for about 30 seconds, followed by rinsing the swatch for about 30 seconds, and then drying at elevated temperature for about 45 minutes. This cycle was repeated for a total of 20 wash/rinse cycles. After each fifth cycle, the swatches were allowed to air dry at room temperature for 16 hours, after which the color of the swatches was evaluated (times=5, 10, 15, 20) before the next cycle. FIG. 9A shows images of the swatches at each of times-1, 0, 5, 10, 15, and 20. As can be seen, hair treated with inventive composition 5B maintains color over successive shampoo cycles better than hair treated with comparative composition C7, which is identical to composition 5B other than the absence of citric acid and urea compounds. Similarly, hair treated with inventive composition 5C maintains color over successive shampoo cycles better than hair treated with comparative composition C8, which is identical to composition 5C other than the absence of citric acid and urea compounds.

Figure 9B:
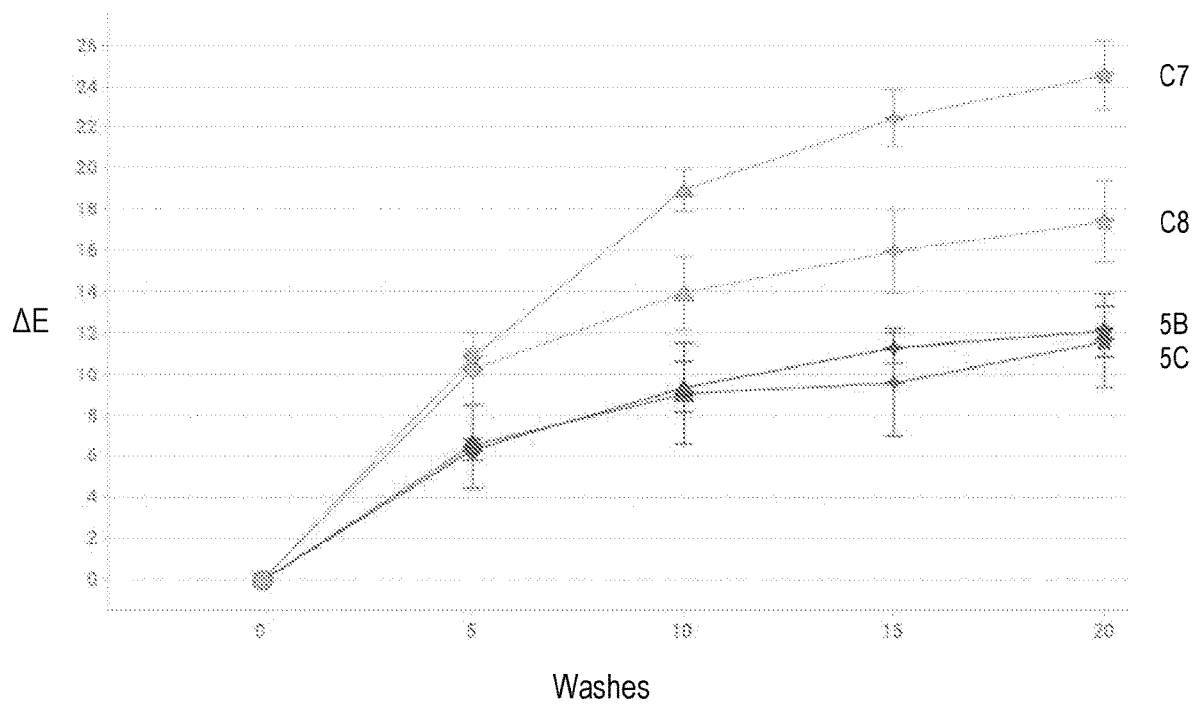

FIG. 9B is a graph of this data, showing the change in color (ΔE) of each swatch which was calculated after each washing according to the following equation:

$$\Delta E = \sqrt{(L^* - L_0^*)^2 + (a^* - a_0^*)^2 + (b^* - b_0^*)^2}$$

where L*, a*, and b* represent the values measured at times 5, 10, 15, and 20, and $L_0^*$, $a_0^*$, and $b_0^*$ represent the values measured at time 0. These data are considered to be both surprising and statistically significant.

In addition, the hair dyed with inventive composition 3B (Example 3B) was evaluated again after six weeks to determine the lastingness of color, and it was observed that the color and enhanced discipline, smoothness, and shine all remained excellent after six weeks.

Examples 5A-5B demonstrate, therefore, that the synergistic combination of citric acid and urea compounds not only surprisingly provides improved benefits such as shine, curl definition and retention, reduced frizz, improved discipline and alignment, better uniformity of color, and ease of detangling when included in a hair dye composition, but also unexpectedly provides significantly improved persistence of color to shampooing and other hair care and styling routines.

Example 6—Bleaching Compositions

Two hair bleaching compositions were prepared using developer composition D4 or D5 (30V) set forth in Table 6A, bleaching composition B1 or B2 set forth in Table 6B, lightening composition L1 or L2 set forth in Table 6C, and a CA-HEU pre-mix as described above in Example 1.

TABLE 6A

|  | Developer Compositions | |
|---|---|---|
|  | D4 | D5 |
| MINERAL OIL |  | 17 |
| HYDROGEN PEROXIDE | 18 | 18 |
| SODIUM CETEARYL SULFATE |  | 0.5 |
| CETEARYL ALCOHOL | 2.28 | 3.2 |
| CETEARETH-25 | 0.57 |  |
| PEG-40 HYDROGENATED CASTOR OIL |  | 0.9 |
| TETRASODIUM ETIDRONATE | 0.2 | 0.4 |
| SODIUM SALICYLATE | 0.04 | 0.05 |
| TETRASODIUM PYROPHOSPHATE | 0.04 | 0.05 |
| GLYCERIN | 0.5 |  |
| TRIDECETH-2 CARBOXAMIDE MEA | 0.85 |  |
| WATER | QS to 100 | QS to 100 |

TABLE 6B

|  | Bleach Compositions | |
|---|---|---|
|  | B1 | B2 |
| MINERAL OIL | 1.6 |  |
| HYDROGENATED POLYDECENE |  | 2 |
| SODIUM SILICATE | 8.8 | 26 |
| SODIUM STEARATE | 4.5 |  |
| SODIUM METASILICATE | 10.4 |  |
| DISODIUM EDTA or EDTA | 0.95 | 1 |
| GLYCINE | 0.6 |  |
| ULTRAMARINES (and) KAOLIN | 0.05 |  |
| TITANIUM DIOXIDE |  | 2 |
| SILICA |  | 2 |
| KAOLIN |  | 7 |
| AMMONIUM PERSULFATE | 9.7 | 11 |
| POTASSIUM PERSULFATE | 48 | 42 |
| SODIUM PERSULFATE |  | 4.9 |
| SODIUM LAURYL SULFATE | 0.8 | 2 |
| MAGNESIUM CARBONATE HYDROXIDE | 9 |  |
| CYAMOPSIS TETRAGONOLOBA (GUAR) GUM | 1.8 |  |
| CITRIC ACID | 3.6 |  |

TABLE 6C

|  | Lightening Compositions | |
|---|---|---|
|  | L1 | L2 |
| GLYCOL DISTEARATE |  | 2 |
| LAURIC ACID |  | 3 |
| LAURETH-12 |  | 7 |
| COCO-BETAINE | 2.5 |  |
| CETEARYL ALCOHOL |  | 11.5 |
| OLEYL ALCOHOL | 6 |  |
| LAURYL ALCOHOL | 2.5 |  |
| SILICA DIMETHYL SILYLATE |  | 1.2 |
| AMMONIUM HYDROXIDE |  | 14 |
| DECETH-3 | 9 | 10 |
| POLYQUATERNIUM-22 |  | 3.7 |
| PEG/PPG-4/12 DIMETHICONE | 1.5 |  |
| CARBOMER |  | 0.4 |
| ETHANOLAMINE | 0.2 | 9.8 |
| PLANT OILS |  | 0.2 |
| OLETH-30 |  | 4 |
| PPG-5-CETETH-10 PHOSPHATE | 0.9 |  |
| SODIUM SULFITE | 0.5 |  |
| PPG-2 BUTYL ETHER | 5 |  |
| COCAMIDE MIPA | 6.5 |  |
| SODIUM C14-16 OLEFIN SULFONATE | 22.5 |  |
| ADDITIVES (preservatives, amino acids, fragrance) | <1 | <1 |
| SOLVENTS (water and non-aqueous solvents) | QS to 100 | QS to 100 |

Inventive composition 6A was prepared by mixing developer D4, bleach composition B1, and lightening composition L1 at a ratio of D4:B1:L1 of 3:2:1, and adding 2.5% of the CA-HEU pre-mix described in Example 1. Comparative composition C9 was prepared in the same manner as 6A, but without adding the CA-HEU pre-mix. Both compositions were prepared just prior to application to the hair.

Inventive composition 6B was prepared by mixing developer D5, bleach composition B2, and lightening composition L2 at a ratio of D5:B2:L2 of about 3.4:1:1.1, and adding 5% of the CA-HEU pre-mix described in Example 1. Comparative composition C10 was prepared in the same manner as 6B, but without adding the CA-HEU pre-mix. Both compositions were prepared just prior to application to the hair.

Swatches of very curly hair were treated with one of compositions 6A-6B or C9-C10 by applying the composition and leaving on the hair for a one-hour processing time. The hair was then thoroughly rinsed and dried.

Although the lift of the color with inventive compositions 6A-6B was slightly less than with comparative compositions C9-C10, the hair color was still lightened. In addition, it was observed that the hair treated with compositions 6A-6B had excellent smoothness, reduced frizz, and better curl retention compared to the hair treated with compositions C9-C10. This example demonstrates that the synergistic benefits achieved with citric acid and urea compounds is therefore also surprisingly seen when used during a bleaching process.

Example 7—Additional Treatment Compositions

The following compositions, which are expected to provide the same surprising shine, curl definition, curl retention, reduced frizz, and improved discipline, alignment, and/or ease of detangling benefits as in the previous examples, can be prepared using the components as shown in Table 7.

TABLE 7

|  | Additional Compositions | | | |
|---|---|---|---|---|
|  | 7A | 7B | 7C | 7D |
| CITRIC ACID |  | 1 | 0.5 | 0.8 |
| SODIUM CITRATE | 2.5 | 1 | 1 |  |
| UREA |  |  |  | 0.5 |
| DIMETHYL UREA |  | 1.4 | 1.1 |  |
| HYDROXYETHYL UREA | 2.5 |  |  |  |
| STEARYL ALCOHOL | 5 | 3 | 2.5 | 1.5 |
| AMODIMETHICONE | 5 | 2.5 | 1.5 | 2.5 |
| GUAR GUM | 0.3 | 0.2 | 0.1 | 0.2 |
| HYALURONIC ACID | 0.2 | 0.1 | 0.1 | 0.3 |

TABLE 7-continued

| | Additional Compositions | | | |
|---|---|---|---|---|
| | 7A | 7B | 7C | 7D |
| HYDROXYETHYL CELLULOSE | 0.5 | 0.2 | 0.4 | 0.2 |
| CETRIMONIUM CHLORIDE | 5 | 2 | 3.5 | 2 |
| CETYL MYRISTATE | 1 | 0.5 | 0.5 | 1.5 |
| ADDITIVES (preservatives, fragrance, pH adjusters, vitamins, and/or colorants) | <5 | <5 | <5 | <5 |
| SOLVENT (water and optionally non-aqueous solvents) | QS | QS | QS | QS |

The above examples demonstrate the surprising and unexpected benefits provided by the synergistic combination of citric acid and urea compounds when used before, during, and after processes for altering the color of the hair, such as improved shine, curl definition and retention, reduced frizz, improved discipline and alignment, better uniformity of color, and ease of detangling, as well as significantly improved persistence of these benefits and lastingness of color to shampooing and other hair care and styling routines.

It will be apparent to those skilled in the art that various modifications and variations can be made in the compositions and methods according to the disclosure without departing from the spirit or scope of the disclosure. Thus, it is intended that the disclosure cover such modifications and variations.

The invention claimed is:

1. A composition for altering the color or tone of hair comprising:
    (a) (i) citric acid, and
        (ii) at least one urea compound chosen from urea and/or derivatives thereof;
    (b) at least one solvent; and
    (c) at least one hair color altering agent chosen from direct dyes, pigments, oxidation dyes, or combinations thereof;
    wherein the mole ratio of citric acid to urea compounds ranges from about 0.4:1 to about 3:1.

2. The composition of claim 1, further comprising at least one compound chosen from silicone compounds, non-silicone fatty compounds, thickening agents, cationic surfactants, or combinations thereof.

3. The composition of claim 1, wherein the weight ratio of the total amount of citric acid to the total amount of urea ranges from about 1:1 to about 1:0.05.

4. The composition of claim 1, wherein the composition comprises a total amount of citric acid ranging from about 0.1% to about 50% by weight, relative to the total weight of the composition.

5. The composition of claim 1, comprising at least one urea compound chosen from urea, dimethyl urea, hydroxyethyl urea, or combinations of two or more thereof.

6. The composition of claim 1, wherein the composition comprises a total amount of urea compounds ranging from about 0.1% to about 20% by weight, relative to the total weight of the composition.

7. The composition of claim 1, further comprising at least one oxidizing agent.

8. The composition of claim 1, wherein the pH of the composition is less than about 10.

9. A composition for treating hair, comprising:
    a) (i) citric acid, and
        (ii) at least one urea compound chosen from urea and/or derivatives thereof;
    (b) at least one solvent; and
    (c) at least one component chosen from silicone compounds, non-silicone fatty compounds, thickening agents, cationic surfactants, or combinations thereof;
    wherein the mole ratio of citric acid to urea compounds ranges from about 0.4:1 to about 3:1; and
    wherein the pH of the composition is less than 7.

10. The composition of claim 9, wherein the weight ratio of the total amount of citric acid to the total amount of urea ranges from about 1:1 to about 1:0.05.

11. The composition of claim 9, wherein the composition comprises a total amount of citric acid ranging from about 0.1% to about 50% by weight, relative to the total weight of the composition.

12. The composition of claim 9, comprising at least one urea compound chosen from urea, dimethyl urea, hydroxylethyl urea, or combinations of two or more thereof.

13. The composition of claim 9, wherein the composition comprises a total amount of urea compounds ranging from about 0.1% to about 20% by weight, relative to the total weight of the composition.

14. The composition of claim 9, wherein the composition comprises at least one cationic surfactant, and the total amount of cationic surfactants ranges from about 0.1% to about 10% by weight, relative to the total weight of the composition.

15. A method for treating hair comprising applying to the hair a composition comprising:
    (a) a combination of:
        (i) citric acid, and
        (ii) at least one urea compound chosen from urea and/or derivatives thereof;
    (b) at least one solvent; and
    (c) at least one additional component chosen from hair coloring agents, silicone compounds, non-silicone fatty compounds, thickening agents, cationic surfactants, or combinations thereof;
    wherein the mole ratio of citric acid to urea compounds ranges from about 0.4:1 to about 3:1.

16. The method of claim 15, wherein the composition has a weight ratio of the total amount of citric acid to the total amount of urea ranging from about 1:1 to about 1:0.05.

17. The method of claim 15, wherein the composition comprises at least one cationic surfactant, and the composition is applied to hair that has been bleached and/or colored.

18. The method of claim 17, wherein the composition is rinsed from the hair after a leave-on period ranging from about 1 minutes to about 60 minutes.

19. The method of claim 15, wherein the method is a method for altering the color or tone of hair, and the composition comprises at least one hair color altering agent chosen from direct dyes, pigments, oxidation dyes, or combinations thereof.

20. The method of claim 19, wherein the composition is rinsed from the hair after a leave-on period ranging from about 5 minutes to about 45 minutes.

* * * * *